United States Patent
Chen et al.

(10) Patent No.: US 11,686,790 B2
(45) Date of Patent: Jun. 27, 2023

(54) SYSTEMS, DEVICES, AND METHODS FOR MAGNETIC RESONANCE IMAGING OF INFANTS

(71) Applicant: Hyperfine Operations, Inc., Guilford, CT (US)

(72) Inventors: Gang Chen, Guilford, CT (US); Anne Michele Nelson, Guilford, CT (US); Jacob Coumans, Old Lyme, CT (US); Eddy B. Boskamp, Shelton, CT (US)

(73) Assignee: Hyperfine Operations, Inc., Guilford, CT (US)

( * ) Notice: Subject to any disclaimer, the term of this patent is extended or adjusted under 35 U.S.C. 154(b) by 85 days.

(21) Appl. No.: 16/864,848

(22) Filed: May 1, 2020

(65) Prior Publication Data

US 2020/0355765 A1 Nov. 12, 2020

Related U.S. Application Data

(60) Provisional application No. 62/970,459, filed on Feb. 5, 2020, provisional application No. 62/883,329, filed (Continued)

(51) Int. Cl.
    *G01R 33/34* (2006.01)
    *A61B 5/055* (2006.01)
    *A61B 5/00* (2006.01)

(52) U.S. Cl.
    CPC ........ *G01R 33/34084* (2013.01); *A61B 5/055* (2013.01); *A61B 5/70* (2013.01); *A61B 2503/04* (2013.01); *A61B 2560/04* (2013.01)

(58) Field of Classification Search
    CPC .............. G01R 33/34084; A61B 5/055; A61B 2503/04; A61B 2560/04
    See application file for complete search history.

(56) References Cited

U.S. PATENT DOCUMENTS

| 4,774,468 A | * | 9/1988 | Bydder | ............ | G01R 33/34061 |
|  |  |  |  |  | 324/318 |
| 5,490,508 A | * | 2/1996 | Kato | .................... | G01R 33/341 |
|  |  |  |  |  | 324/318 |

(Continued)

FOREIGN PATENT DOCUMENTS

| JP | S64-86961 A | 3/1989 |
| WO | WO 2017/183024 A1 | 10/2017 |

OTHER PUBLICATIONS

PCT/US2020/030935, Aug. 24, 2020, Invitation to Pay Additional Fees.

(Continued)

*Primary Examiner* — Dixomara Vargas
(74) *Attorney, Agent, or Firm* — Wolf, Greenfield & Sacks, P.C.

(57) ABSTRACT

Provided herein are systems, devices, and methods to facilitate imaging an infant using a magnetic resonance imaging (MRI) device. A system for facilitating imaging an infant using an MRI device is provided herein, the system comprising a radio frequency (RF) coil assembly configured to be coupled to the MRI device and comprising a first RF coil configured to transmit RF signals during MRI and/or be responsive to MR signals generated during MRI and a helmet for supporting at least a portion of the infant's head, and an infant support to support at least a portion of the infant's body and configured to be coupled to the RF coil assembly. Further provided is an apparatus for coupling an infant support to an MRI device.

19 Claims, 54 Drawing Sheets

Related U.S. Application Data on Aug. 6, 2019, provisional application No. 62/844,702, filed on May 7, 2019.

(56) References Cited

U.S. PATENT DOCUMENTS

| | | | |
|---|---|---|---|
| 7,315,168 B2 | 1/2008 | Rapoport et al. | |
| 7,400,147 B2 | 7/2008 | Rapoport | |
| 9,541,616 B2 | 1/2017 | Rothberg et al. | |
| 9,547,057 B2 | 1/2017 | Rearick et al. | |
| 9,625,544 B2 | 4/2017 | Poole et al. | |
| 9,645,210 B2 | 5/2017 | McNulty et al. | |
| 9,817,093 B2 | 11/2017 | Rothberg et al. | |
| 10,145,913 B2 | 12/2018 | Hugon et al. | |
| 10,145,922 B2 | 12/2018 | Rothberg et al. | |
| 10,222,434 B2 | 3/2019 | Poole et al. | |
| 10,274,561 B2 | 4/2019 | Poole et al. | |
| 10,281,540 B2 | 5/2019 | Mileski et al. | |
| 10,281,541 B2 | 5/2019 | Poole et al. | |
| 10,310,037 B2 | 6/2019 | McNulty et al. | |
| 10,416,264 B2 | 9/2019 | Sofka et al. | |
| 10,551,452 B2 | 2/2020 | Rearick et al. | |
| 10,591,561 B2 | 3/2020 | Sacolick et al. | |
| 10,709,387 B2 | 7/2020 | Poole et al. | |
| 11,553,853 B2 | 1/2023 | Coumans et al. | |
| 2002/0173717 A1* | 11/2002 | Rohling | A61B 5/055 600/415 |
| 2004/0015074 A1* | 1/2004 | Srinivasan | G01R 33/34046 324/318 |
| 2004/0075437 A1* | 4/2004 | Srinivasan | G01R 33/34046 324/318 |
| 2005/0113668 A1* | 5/2005 | Srinivasan | A61B 5/416 600/422 |
| 2008/0231278 A1* | 9/2008 | Ishihara | G01R 33/3415 324/318 |
| 2009/0179643 A1* | 7/2009 | Lin | G01R 33/4824 324/312 |
| 2012/0126814 A1 | 5/2012 | Fischer et al. | |
| 2014/0159727 A1* | 6/2014 | Lee | G01R 33/34092 324/322 |
| 2016/0069975 A1 | 3/2016 | Rothberg et al. | |
| 2016/0089055 A1* | 3/2016 | Rapoport | A61F 7/00 600/415 |
| 2016/0128592 A1 | 5/2016 | Rosen et al. | |
| 2016/0131727 A1 | 5/2016 | Sacolick et al. | |
| 2016/0334479 A1* | 11/2016 | Poole | A61B 5/7203 |
| 2018/0070852 A1 | 3/2018 | Azulay et al. | |
| 2018/0153435 A1* | 6/2018 | Rapoport | A61G 11/005 |
| 2019/0038233 A1 | 2/2019 | Poole et al. | |
| 2019/0324098 A1 | 10/2019 | McNulty et al. | |
| 2019/0328271 A1* | 10/2019 | Rabinovitz | G01R 33/28 |
| 2019/0328596 A1* | 10/2019 | Rapoport | A61G 11/007 |
| 2019/0353723 A1 | 11/2019 | Dyvorne et al. | |
| 2019/0353726 A1 | 11/2019 | Poole et al. | |
| 2020/0022611 A1 | 1/2020 | Nelson et al. | |
| 2020/0022612 A1 | 1/2020 | McNulty et al. | |
| 2020/0034998 A1 | 1/2020 | Schlemper et al. | |
| 2020/0041588 A1 | 2/2020 | O'Halloran et al. | |
| 2020/0045112 A1 | 2/2020 | Sacolick et al. | |
| 2020/0058106 A1 | 2/2020 | Lazarus et al. | |
| 2020/0150202 A1 | 5/2020 | Hugon et al. | |
| 2020/0200844 A1 | 6/2020 | Boskamp et al. | |
| 2020/0209334 A1 | 7/2020 | O'Halloran et al. | |
| 2020/0289019 A1 | 9/2020 | Schlemper et al. | |
| 2020/0289022 A1* | 9/2020 | Coumans | G01R 33/287 |
| 2020/0294229 A1 | 9/2020 | Schlemper et al. | |
| 2020/0294282 A1 | 9/2020 | Schlemper et al. | |
| 2020/0294287 A1 | 9/2020 | Schlemper et al. | |
| 2020/0337587 A1 | 10/2020 | Sacolick et al. | |
| 2020/0352473 A1* | 11/2020 | Chen | G01R 33/34084 |
| 2021/0048498 A1 | 2/2021 | Dyvorne et al. | |
| 2021/0121066 A1* | 4/2021 | Rheineck | A61B 5/0035 |

OTHER PUBLICATIONS

Invitation to Pay Additional Fees for International Application No. PCT/US2020/030935 dated Aug. 24, 2020.
PCT/US2020/030935, Oct. 15, 2020, International Search Report and Written Opinion.
U.S. Appl. No. 16/815,534, filed Mar. 11, 2020, Coumans et al.
U.S. Appl. No. 16/864,859, filed May 1, 2020, Chen et al.
PCT/US2020/021969, May 15, 2020, International Search Report and Written Opinion.
International Search Report and Written Opinion for International Application No. PCT/US2020/030935 dated Oct. 15, 2020.
International Search Report and Written Opinion for International Application No. PCT/US2020/021969 dated May 15, 2020.
International Preliminary Report on Patentability for International Application No. PCT/US2020/021969 dated Sep. 23, 2021.
International Preliminary Report on Patentability for International Application No. PCT/US2020/030935 dated Nov. 18, 2021.
U.S. Appl. No. 18/096,856, filed Jan. 13, 2023, Coumans et al.

* cited by examiner

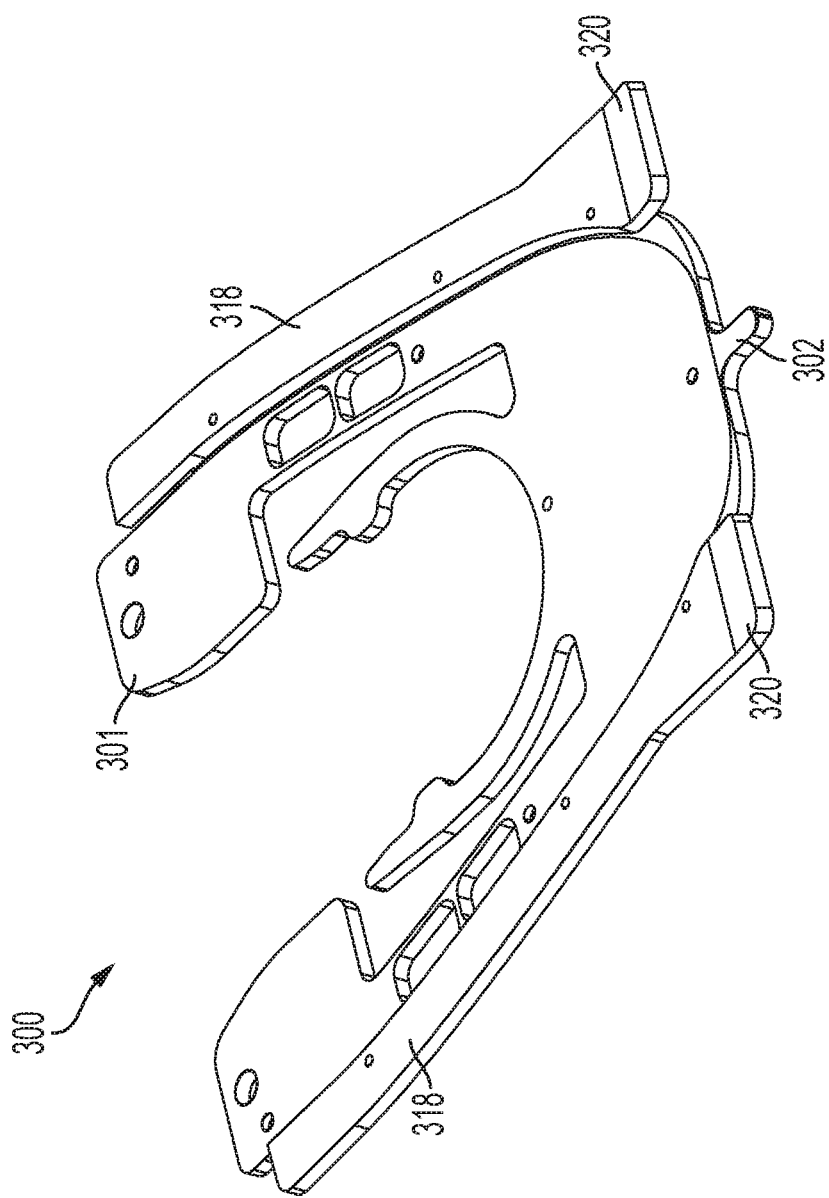

SYSTEMS, DEVICES, AND METHODS FOR MAGNETIC RESONANCE IMAGING OF INFANTS

CROSS-REFERENCE TO RELATED APPLICATIONS

This application claims the benefit under 35 U.S.C. § 119(e) of U.S. Provisional Application Ser. No. 62/844,702 titled "RADIO-FREQUENCY HEAD COIL FOR NEONATAL MAGNETIC RESONANCE IMAGING" and filed on May 7, 2019, U.S. Provisional Application Ser. No. 62/883,329 titled "RADIO-FREQUENCY HEAD COIL FOR NEONATAL MAGNETIC RESONANCE IMAGING" and filed on Aug. 6, 2019, and U.S. Provisional Application Ser. No. 62/970,459 titled "INFANT SUPPORT STRUCTURE FOR MAGNETIC RESONANCE IMAGING" and filed on Feb. 5, 2020, each of which is incorporated by reference in its entirety herein.

FIELD

The present disclosure relates generally to magnetic resonance imaging (MRI) devices and, more specifically, systems and methods for positioning an infant relative to an MRI device.

BACKGROUND

Magnetic resonance imaging provides an important imaging modality for numerous applications and is widely utilized in clinical and research settings to produce images of the inside of the human body. MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive imaging modality for biological imaging due to the ability to produce non-invasive images having relatively high resolution and contrast without the safety concerns of other modalities (e.g., without needing to expose the subject to ionizing radiation, e.g., x-rays, or introducing radioactive material to the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring.

SUMMARY

Some embodiments provide for a system to facilitate imaging an infant using a magnetic resonance imaging (MRI) device, the system comprising: a radio frequency (RF) coil assembly configured to be coupled to the MRI device, the RF coil assembly comprising: a first RF coil configured to transmit RF signals during MRI and/or be responsive to MR signals generated during MRI; and a helmet for supporting at least a portion of the infant's head; and an infant support to support at least a portion of the infant's body and configured to be coupled to the RF coil assembly.

In some embodiments the helmet supports the first RF coil. In some embodiments, the first RF coil is housed inside the helmet. In some embodiments, the first RF coil is disposed on or proximate to an exterior surface of the helmet. In some embodiments, the RF coil assembly further comprises a second RF coil configured to receive MR signals during MRI, the second RF coil being removably coupled to the helmet.

In some embodiments, the infant support is configured to be coupled to the helmet. In some embodiments, the first RF coil is removably coupled to the helmet.

In some embodiments, the infant support comprises: a tray for positioning the infant thereon along a longitudinal axis extending along a length of the tray, the tray having a surface and sides coupled to and extending upwards from the surface; and a base coupled to the tray, the base comprising arms extending outward from the base in a direction along the longitudinal axis and configured to be received by a coupling mechanism of the MRI device.

In some embodiments, the system further comprises the coupling mechanism, the coupling mechanism comprising: first and second receiving portions for receiving the arms of the infant support, wherein the coupling mechanism is coupled to the MRI device and the RF coil assembly. In some embodiments, the coupling mechanism further comprises: guides on opposing sides of the coupling mechanism; and wings disposed at least partially above the guides; wherein the wings and guides together form the first and second receiving portions for receiving the arms of the infant support, the first and second receiving portions being configured such that the arms of the infant support are inserted into the first and second receiving portions below the wings and along the guides. In some embodiments, distal ends of the guides are configured to receive a respective snap disposed at distal ends of the arms of the infant support.

In some embodiments, the RF coil assembly is electrically coupled to the MRI device. In some embodiments, the RF coil assembly is mechanically coupled to the MRI device. In some embodiments, the helmet is dimensioned to accommodate the infant's head. In some embodiments, a maximum dimension of an interior of the helmet is less than 20 centimeters.

Some embodiments provide for an infant support for supporting an infant during imaging by a magnetic resonance imaging (MRI) device, the apparatus comprising: a tray for positioning the infant thereon along a longitudinal axis extending along a length of the tray, the tray having a surface and sides coupled to and extending upwards from the surface; and a base coupled to the tray, the base comprising arms extending outward from the base in a direction along the longitudinal axis.

In some embodiments, the arms slope upward in the direction along the longitudinal axis. In some embodiments, the arms are configured to be received by respective receiving portions of a coupling mechanism coupled to the MRI device. In some embodiments, each of the arms comprise a respective snap at a distal end of the arm, the snap configured to be received by the coupling mechanism.

In some embodiments, the infant support further comprises a bridge supporting the tray on the base and providing a gap between the base and the tray. In some embodiments, the base further comprises a notch disposed between the arms, the notch complementary to a protrusion of a coupling mechanism coupled to the MRI device. In some embodiments, the base further comprises a protrusion disposed between the arms, the protrusion complementary to a notch of a coupling mechanism coupled to the MRI device. In some embodiments, each of the sides comprises one or more slots for receiving one or more straps.

In some embodiments, the surface is tapered such that a proximal end of the surface has a width that is greater than a width of a distal end of the surface. In some embodiments, the infant support comprises one or more tabs coupled to the distal end of the surface to support the infant's head. In some embodiments, the infant support comprises a brace disposed above and coupled to the distal end of the surface. In some embodiments, the tray further comprises padding.

Some embodiments provide for a method for positioning an infant in a field of view of a magnetic resonance imaging (MRI) device using an infant support configured to support the infant during imaging, the infant support comprising a base, a tray supported by the base, and arms coupled to the base, the method comprising: placing the infant on the tray along a longitudinal axis of the infant support; moving the infant support towards an RF coil assembly of the MRI device in a direction along the longitudinal axis so that the arms are inserted into a coupling mechanism coupled to the RF coil assembly and at least a portion of the infant's head is disposed within an opening of the RF coil assembly; and imaging the infant using the MRI device.

In some embodiments, the moving comprises moving the infant support until either a notch of the infant support receives a protrusion of the coupling mechanism or a protrusion of the infant support is received by a notch of the coupling mechanism. In some embodiments, the moving comprises moving the infant support until snaps disposed at distal ends of the arms are received by respective distal ends of guides of the coupling mechanism. In some embodiments, the method further comprises, after placing the infant on the tray, extending one or more straps over the infant.

Some embodiments provide for an apparatus for coupling an infant support to a magnetic resonance imaging (MRI) device, the infant support comprising a base and arms coupled to the base, the apparatus comprising: a body; outer arms coupled to the body and configured to receive arms of the infant support; and inner arms coupled to the body and configured to couple the apparatus to the MRI device.

In some embodiments, the body comprises a notch, the notch complementary to a protrusion of the infant support. In some embodiments, the body comprises a protrusion, the protrusion complementary to a notch of the infant support. In some embodiments, the outer arms comprise guides for receiving the arms of the infant support.

In some embodiments, the apparatus further comprises wings coupled to the body and disposed at least partially above the guides; and wherein the wings and guides together form first and second receiving portions for receiving the arms of the infant support, the first and second receiving portions being configured such that the arms of the infant support are inserted into the first and second receiving portions below the wings and along the guides. In some embodiments, distal ends of the guides are configured to receive a respective snap disposed at distal ends of the arms of the infant support. In some embodiments, the wings slope upwards along a longitudinal axis extending substantially along a length of the wings.

In some embodiments, each of the inner arms comprise a contact configured to be received by a groove of the MRI device. In some embodiments, the MRI device comprises a helmet base, the helmet base comprising the groove, and the contacts of the inner arms are configured be received by the groove of the helmet base to couple the apparatus to the helmet base.

Some embodiments provide for a system configured to facilitate imaging of an infant using a magnetic resonance (MRI) device, the system comprising: an infant support for supporting the infant during imaging by the MRI device, the infant support comprising: a tray for positioning the infant thereon along a longitudinal axis extending along a length of the tray; and a base coupled to the tray, the base comprising arms extending outward from the base in a direction along the longitudinal axis distal to the base; and an apparatus for coupling the infant support to the MRI device comprising: a body; outer arms coupled to the body and configured to receive the arms of the infant support; and inner arms coupled to the body and configured to couple to the apparatus to the MRI device.

In some embodiments, the apparatus comprises a notch and the infant support comprises a protrusion configured to be received by the notch. In some embodiments, the infant support comprises a notch and the apparatus comprises a protrusion configured to be received by the notch.

In some embodiments, the outer arms comprise guides for receiving the arms of the infant support. In some embodiments, the apparatus further comprises: wings coupled to the body and disposed at least partially above the guides; and wherein the wings and guides together form first and second receiving portions for receiving the arms of the infant support, the first and second receiving portions being configured such that the arms of the infant support are inserted into the first and second receiving portions below the wings and along the guides. In some embodiments, distal ends of the arms comprise snaps; and distal ends of the guides are configured to receive a respective one of the snaps.

Some embodiments provide for an apparatus for coupling an infant support to a magnetic resonance imaging (MRI) device, the infant support comprising a base and arms coupled to the base, the apparatus comprising: a body; guides coupled to the body; and wings coupled to the body and disposed at least partially above the guides, wherein the wings and guides together form first and second receiving portions for receiving the arms of the infant support, the first and second receiving portions being configured such that the arms of the infant support are inserted into the first and second receiving portions below the wings and along the guides.

In some embodiments, the body comprises a notch, the notch complementary to a protrusion of the infant support. In some embodiments, the body comprises a protrusion, the protrusion complementary to a notch of the infant support.

In some embodiments, distal ends of the guides are configured to receive a respective snap disposed at distal ends of the arms of the infant support. In some embodiments, the wings slope upwards along a longitudinal axis extending substantially along a length of the wings.

In some embodiments, the apparatus further comprises inner arms coupled to the body and configured to couple the apparatus to the MRI device. In some embodiments, each of the inner arms comprise a contact configured to be received by a groove of the MRI device. In some embodiments, the MRI device comprises a helmet base, the helmet base comprising the groove, and the contacts of the inner arms are configured be received by the groove of the helmet base to couple the apparatus to the helmet base.

BRIEF DESCRIPTION OF THE DRAWINGS

Various non-limiting embodiments of the technology are described herein with reference to the following figures. It should be appreciated that the figures are not necessarily drawn to scale. Items appearing in multiple figures are indicated by the same reference numeral in all figures in which they appear. For purposes of clarity, not every component may be labeled in every drawing.

FIG. 27 is a perspective view of the example coupling mechanism of FIG. 26 having wings for facilitating coupling to an infant support, in accordance with some embodiments of the technology described herein.

DETAILED DESCRIPTION

Figure 1:
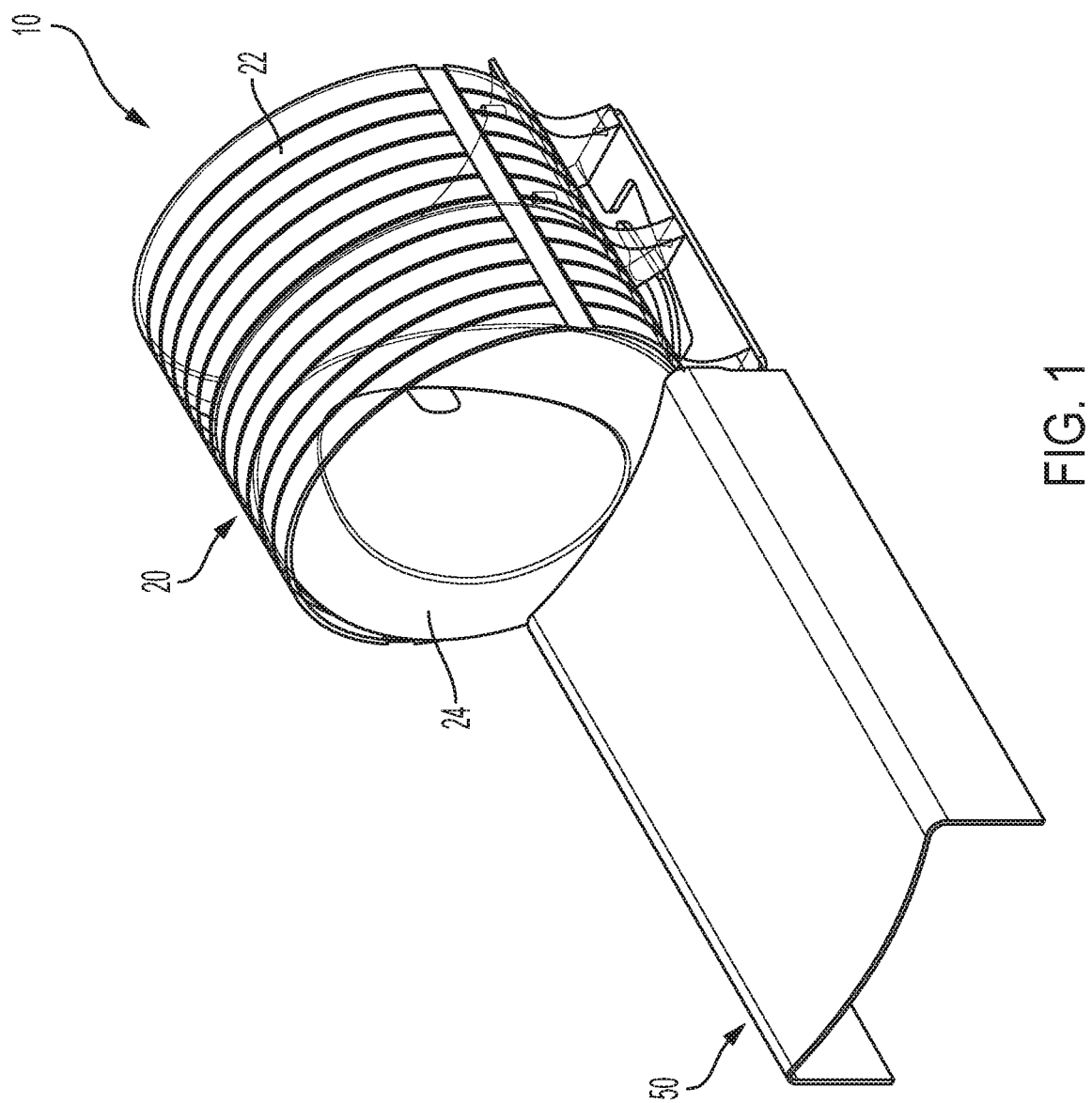
FIG. 1 is a perspective view of an example system to facilitate imaging an infant using an MRI device, in accordance with some embodiments of the technology described herein.

Aspects of the present application relate to a system configured to facilitate imaging infants (e.g., neonates and older infants) using a magnetic resonance imaging device. Some aspects relate to an infant support for securing and precisely positioning an infant relative to an MRI device. The infant support may be used alone or in combination with a radio frequency (RF) coil assembly configured to facilitate MR imaging of at least a portion of the infant's head. In addition, the inventors have developed a coupling mechanism for positioning and securely coupling the infant support relative to the MRI device. In some embodiments, the coupling mechanism facilitates coupling the RF coil assembly to the MRI device.

The inventors have recognized that, despite providing an important diagnostic tool, use of MRI is complicated by the lack of availability and accessibility of current MRI systems. The inventors have further recognized that infant care is one area in which MR imaging would be beneficial, but which is often inaccessible. In particular, for neonates (e.g., infants within the first 28 days after birth) alone, there are on the order of 1,000 Neonatal Intensive Care Units (NICUs) in the United States. The average number of beds (or NICU stations) is 21 per NICU for a total of 21,000 beds. Despite providing a potent diagnostic modality for investigating infant complications (e.g., abnormal infant brain function), MRI is often unavailable to infants in need of this technology.

Patient positioning is an important aspect of MR imaging, which impacts the quality of obtained. In particular, it is often desired to obtain an image of a particular portion of a patient's body, such as the brain or spinal cord. As such, it is important to precisely position a patient relative to the MRI device such that images of the appropriate part of the patient's body can be obtained. Another aspect of patient positioning includes minimizing movement of the patient and/or other components of the MRI system during imaging to prevent artefacts from appearing in the acquired images. This is especially problematic when imaging infants given the relative difference in size between infants and adults and/or older children. Indeed, conventional MRI machines developed for adult patients cannot be suitably used for infants as the machine is not able to accurately position a patient of a smaller size. In addition, infants may be relatively more prone to movement during imaging, which necessitates using movement restriction mechanisms to obtain useful images. Thus, in many cases, MR imaging of infants cannot be performed by conventional machines for imaging adults and can only be performed by specialized machines specifically adapted for imaging smaller patients.

The inventors have recognized that the above described issues and others can be overcome with use of a structure configured to position infants relative to an MRI device during MR imaging and which may be used to adapt a conventional MRI device configured for imaging adults into an MRI device that is capable of imaging infants, thus increasing the availability of MR imaging for infants. The infant support may securely couple to one or more components of an existing MRI device such that an infant can be precisely positioned relative to the MRI device for imaging with minimal movement of the infant support and infant. In some embodiments, the infant support may be coupled to an RF coil assembly configured for imaging at least a portion of the infant's head. The RF coil assembly may include components (e.g., a helmet) for positioning and restraining the infant during MR imaging.

Thus, aspects of the present disclosure relate to systems, devices, and methods for facilitating MR imaging of an infant. According to some aspects of the technology described herein, there is provided a system to facilitate imaging an infant using an MRI device, the system comprising: (1) an RF coil assembly configured to be coupled to the MRI device (e.g., mechanically coupled, electronically coupled), the RF coil assembly comprising: (a) a first RF coil configured to transmit RF signals during MRI and/or be responsive to MR signals generated during MRI, and (b) a helmet for supporting at least a portion of the infant's head; and (2) an infant support to support at least a portion of the infant's body and configured to be coupled to the RF coil assembly (to the helmet, for example).

In some embodiments, the helmet supports the first RF coil (e.g., where the RF coil is housed inside the helmet). In some embodiments, the first RF coil is disposed on or proximate to an exterior surface of the helmet. In some embodiments, the first RF coil is removably coupled to the helmet. In some embodiments, the RF coil assembly further comprises a second RF coil configured to receive MR signals during MR and the second RF coil is removably coupled to the helmet. In some embodiments, the helmet is dimensioned to accommodate the infant's head (for example, the helmet may have a maximum interior dimension of less than 20 centimeters).

According to some aspects of the technology described herein, there is provided an infant support for supporting an infant during imaging by an MRI device, the apparatus comprising a tray for positioning the infant thereon along a longitudinal axis extending along a length of the tray, the tray having a surface and sides coupled to and extending upwards from the surface, and a base coupled to the tray, the base comprising arms extending outward from the base in a direction along the longitudinal axis.

In some embodiments, the arms slope upward in the direction along the longitudinal axis. In some embodiments, the arms are configured to be received by respective receiving portions of a coupling mechanism coupled to the MRI device. In some embodiments, each of the arms comprises a respective snap at a distal end of the arm configured to be received by the coupling mechanism. In some embodiments, the infant support further comprises a bridge supporting the tray on the base and providing a gap between the base and the tray. In some embodiments, the base of the infant support further comprises a notch and/or a protrusion disposed between the arms and being complementary to a respective protrusion and/or notch of the coupling mechanism. In some embodiments, each of the sides comprises one or more slots for receiving one or more straps. In some embodiments, the surface of the infant support is tapered such that a proximal end of the surface has a width that is greater than a width of a distal end of the surface. In some embodiments, the infant support comprises one or more tabs coupled to the distal end 113B of the surface to support the infant's head. In some embodiments, the infant support comprises a brace disposed above (or below) and coupled to the distal end 113B of the surface. In some embodiments, the tray of the infant support further comprises padding.

According to some aspects of the technology described herein, there is provided a method for positioning an infant in a field of view of an MRI device using an infant support configured to support the infant during imaging, the infant support comprising a base, a tray supported by the base, and arms coupled to the base, the method comprising: placing the infant on the tray along a longitudinal axis of the infant support; moving the infant support towards an RF coil assembly of the MRI device in a direction along the longitudinal axis so that the arms of the infant support are inserted into a coupling mechanism coupled to the RF coil assembly and at least a portion of the infant's head is disposed within an opening of the RF coil assembly, and imaging the infant using the MRI device.

In some embodiments, moving the infant support comprises moving the infant support until either a notch of the infant support receives a protrusion of the coupling mechanism or a protrusion of the infant support is receive by a notch of the coupling mechanism. In some embodiments, moving the infant support comprises moving the infant support until at distal ends of the arms are received by respective distal ends of guides of the coupling mechanism. In some embodiments, the method further comprises extending one or more straps over the infant after placing the infant on the tray.

According to some aspects of the technology described herein, there is provided an apparatus for coupling an infant support to an MRI device, the infant support comprising a base and arms coupled to the base, the apparatus comprising a body, outer arms coupled to the body and configured to receive arms of the infant support, and inner arms coupled to the body and configured to couple the apparatus to the MRI device.

In some embodiments, the body comprises a notch and/or a protrusion complementary to a respective protrusion and/or notch of the infant support. In some embodiments, the outer arms comprise guides for receiving the arms of the infant support. In some embodiments, the apparatus further comprises wings coupled to the body and disposed at least partially above the guides, wherein the wings and guides together form first and second receiving portions for receiving the arms of the infant support and being configured such that the arms of the infant support are inserted into the first and second receiving portions below the wings and along (e.g., adjacent to) to the guides. In some embodiments, distal ends of the guides are configured to receive a respective snap disposed at distal ends of the arms of the infant support (e.g., by snap fitting the snaps to the distal ends of the guides). In some embodiments, the wings of the apparatus slope upwards along a longitudinal axis extending substantially along a length of the wings. In some embodiments, each of the inner arms of the apparatus comprises a contact configured to be received by a groove of the MRI device (for example, by a groove of a helmet base of the MRI device such that the helmet base is coupled to the apparatus by contacts of the inner arms being received by the groove of the helmet base).

According to some aspects of the technology described herein, there is provided a system configured to facilitate imaging of an infant using an MRI device, the system comprising an infant support for supporting the infant during imaging by the MRI device, the infant support comprising a tray for positioning the infant thereon along a longitudinal axis extending along a length of the tray, and a base coupled to the tray, the base comprising arms extending outward from the base in a direction along the longitudinal axis distal to the base. The system may further comprise an apparatus for coupling the infant support to the MRI device, the apparatus comprising a body, outer arms coupled to the body and configured to receive the arms of the infant support, and inner arms coupled to the body and configured to couple the apparatus to the MRI device.

In some embodiments, the apparatus comprises a notch and the infant support comprises a protrusion configured to be received by the notch. In some embodiments, the infant support comprises a notch and the apparatus comprises a protrusion configured to be received by the notch. In some embodiments, the outer arms of the apparatus comprise guides for receiving the arms of the infant support. In some embodiments, the apparatus further comprises wings coupled to the body and disposed at least partially above the guides, and the wings and guides together form first and second receiving portions for receiving the arms of the infant support and being configured such that the arms of the infant support are inserted into the first and second receiving portions below the wings and along (e.g., adjacent to) to the guides. In some embodiments, distal ends of the arms comprise snaps and distal ends of the guides are configured to receive a respective one of the snaps.

The aspects and embodiments described above, as well as additional aspects and embodiments, are described further below. These aspects and/or embodiments may be used individually, all together, or in any combination, as the technology is not limited in this respect.

Aspects of the technology described herein relate to systems, devices, and methods configured to facilitate imaging of infants. Some embodiments relate to facilitating MR imaging of at least a portion of the infant's head. FIG. 1 is a perspective view of an example system to facilitate imaging an infant using an MRI device, in accordance with some embodiments of the technology described herein. As shown in FIG. 1, the system 10 comprises an RF coil assembly 20 and an infant support 50.

RF coil assembly 20 comprises at least one RF coil configured to transmit RF signals and/or receive MR signals during MR imaging, also referred to herein as transmit and receive coils. In some embodiments, the at least one RF coil may consist of a single RF coil, which may be a transmit (Tx) RF coil, a receive (Rx) RF coil, or both a transmit RF coil and a receive RF (Tx/Rx) coil. In some embodiments, the at least one RF coil may include multiple coils, each of which may be a transmit (Tx) coil, a receive (Rx) coil, or both a transmit coil and a receive (Tx/Rx) coil.

In the illustrated in embodiment, the RF coil assembly 20 includes a first RF coil 22. In some embodiments, the RF coil assembly 20 further includes one or more additional RF coils. In the illustrated embodiment, the first RF coil 22 is a Tx coil configured to transmit RF signals during MR imaging. In other embodiments, RF coil assembly 20 additionally or alternatively includes one or more other RF coils. For example, the RF coil assembly may include one or more Rx coils and/or one or more Tx/Rx coils. The Tx/Rx coils of the RF coil assembly 20 may, in some embodiments, be used in combination with an MRI device to perform magnetic resonance imaging of an infant.

The system 10 further includes an infant support 50 configured to support an infant during MR imaging. In particular, the infant support 50 may be dimensioned for supporting the infant, for example, having a length and width suitable for (e.g., approximately being equal to the dimensions of the infant) placing the infant thereon during MR imaging.

In some embodiments, the infant support 50 may be coupled to the RF coil assembly 20. For example, the infant support 50 may be coupled to a helmet 24 of the RF coil assembly 20, as described herein. In some embodiments, the infant support 50 may include components allowing the infant support 50 to be coupled to a coupling mechanism coupled to the RF coil assembly 20 and/or an MRI device.

Figure 2:
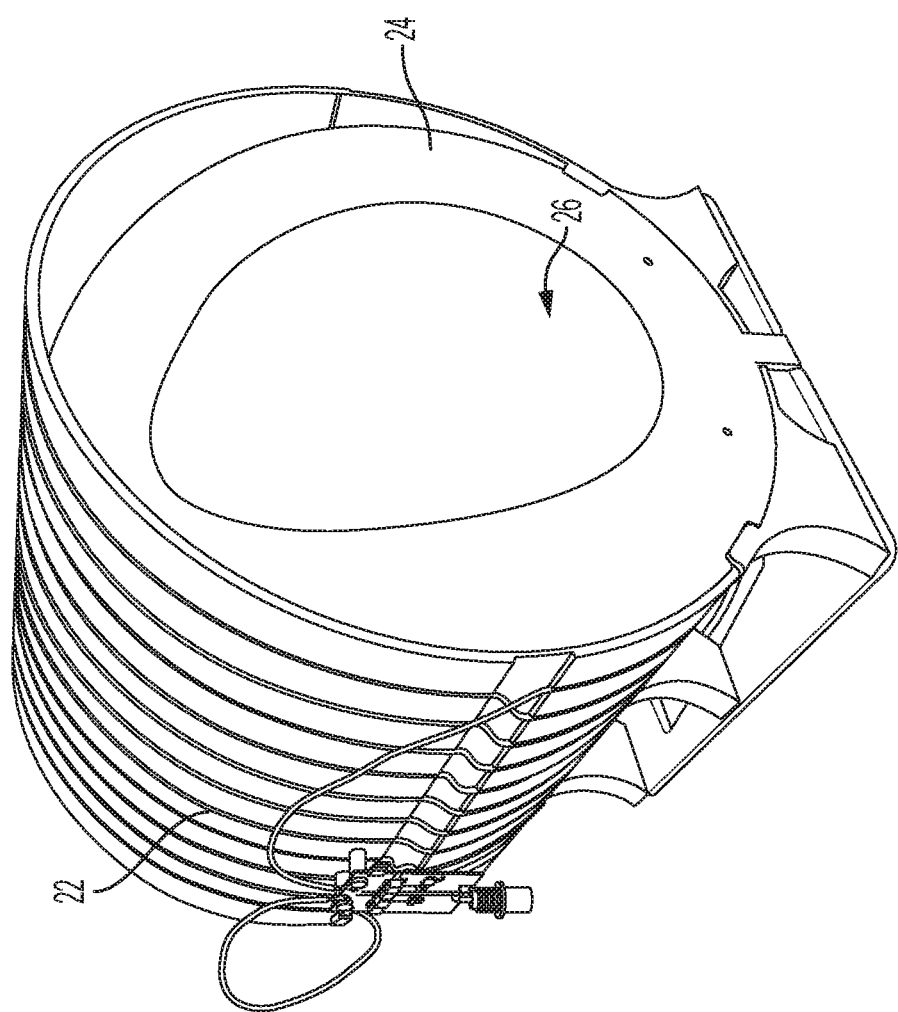
FIG. 2 is perspective view of an example RF coil assembly of the example system of FIG. 1, in accordance with some embodiments of the technology described herein.

FIG. 2 is perspective view of an example RF coil assembly of the example system of FIG. 1, in accordance with some embodiments of the technology described herein. FIG. 2 shows a helmet 24 of the RF coil assembly 20. Helmet 24 may be configured to support the head of an infant during MR imaging. For example, the helmet 24 may receive at least a portion of the infant's head in an opening 26 of the helmet 24. The helmet 24 may be formed of any suitable material, for example, a material which supports the infant's head but which is also comfortable for the infant. In some embodiments, the helmet 24 comprises foam. In some embodiments, the helmet comprises plastic.

The helmet 24 of the RF coil assembly 20 may have any suitable form. For example, in some embodiments, the helmet may have an opening for receiving the infant's head shaped such that the sides and top of the infant's head are enclosed during imaging. In some embodiments, the helmet may have an opening for receiving the infant's head shaped such that the sides of the infant's head are enclosed during imaging while the top of the infant's head is at least partially exposed by the helmet. In some embodiments, the helmet may support the infant's head during imaging while not fully surrounding the entire circumference of the infant's head.

In some embodiments, the helmet may be dimensioned for supporting the infant's head during imaging. For example, the opening 26 of the helmet 24 may be sized to securely receive the infant's head. In some embodiments, the opening of the helmet may be approximately 15 cm along the superior-inferior axis ("SI"), approximately 17 cm along the anterior-posterior axis ("AP"), and approximately 15 cm along the left-right axis ("LR"). A maximum interior dimension of the helmet (e.g., a maximum dimension of the opening) may be less than and/or equal to 15 cm, 16 cm, 17 cm, 18 cm, 19 cm, 20 cm, 21 cm, 22 cm, and/or any suitable dimension in the range of 15-22 cm.

In some embodiments, the RF coil assembly may be configured for imaging an adult's head (e.g., having interior dimensions in the range of 20-30 cm), but the helmet may adapted to support an infant's head. For example, the helmet 24 may be removably coupled to the RF coil assembly 20 such that the helmet 24 may be interchanged with another helmet having an opening suitably sized for the patient being imaged. In some embodiments, both the RF coil assembly including the one or more RF coils and helmet are sized for an infant. In some embodiments, the RF coil assembly including the helmet is sized for an adult and the infant support includes components which facilitate imaging an infant using the adult RF coil assembly and helmet, as described herein.

Figure 3:
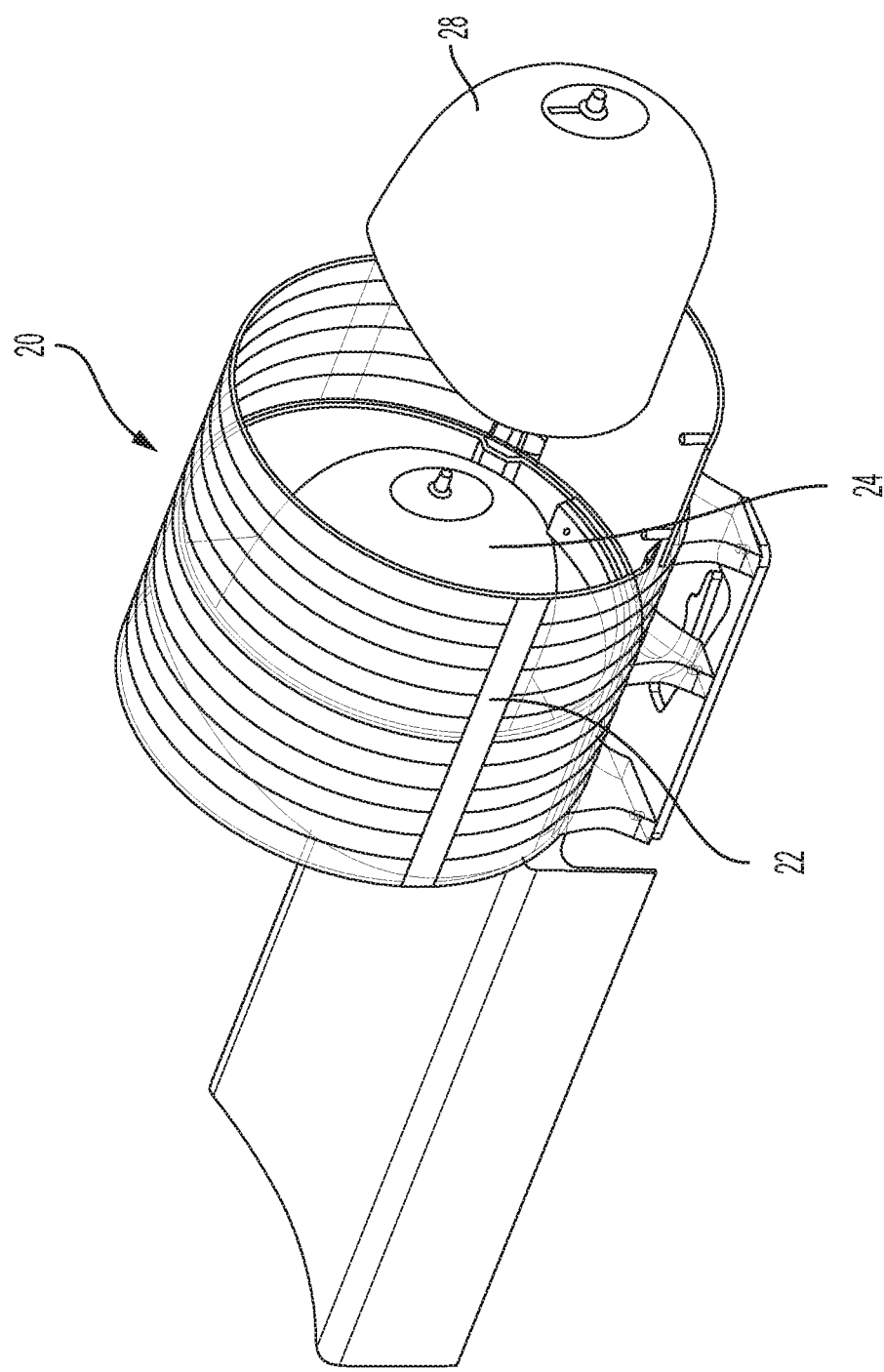
FIG. 3 is a perspective view of the example system of FIG. 1 having a second RF coil removably coupled to the system, in accordance with some embodiments of the technology described herein.

FIG. 3 is a perspective view of the example system of FIG. 1 having a second RF coil removably coupled to the system, in accordance with some embodiments of the technology described herein. As shown in FIG. 3, the RF coil assembly 20 further comprises a second RF coil 28. Second RF coil 28 is removably coupled to the RF coil assembly 20, for example to the helmet 24 such that the second RF coil 28 may be detached from the RF coil assembly 20 when desired. In other embodiments, the second RF coil 28 may be fixedly coupled to the RF coil assembly 20.

In some embodiments, the second RF coil 28 may comprise one or more Tx coils, one or more Rx coils and/or one or more Tx/Rx coils removably coupled to the RF coil assembly 20. In the illustrated embodiment, the second RF coil 28 is an Rx coil configured to receive MR signals during imaging. The inventors have recognized that the use of a second RF coil that can be removably coupled to the RF coil assembly 20 when desired is advantageous as it allows for the RF coil assembly 20 to be reconfigured as necessary.

Figure 4:
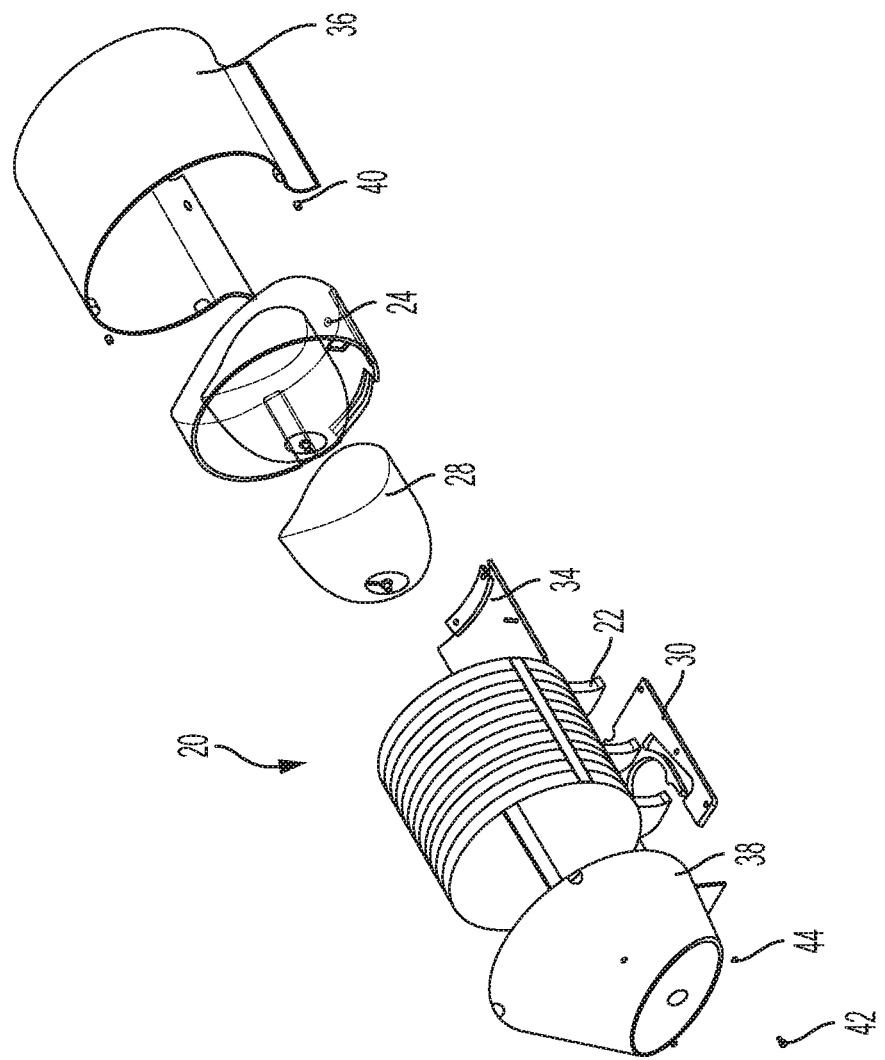
FIG. 4 is an exploded view of the components of the example RF coil assembly of the example system of FIG. 1, in accordance with some embodiments of the technology described herein.

FIG. 4 is an exploded view of the components of the example RF coil assembly of the example system of FIG. 1, in accordance with some embodiments of the technology described herein. As shown in FIG. 4, the RF coil assembly 20 includes first RF coil 22, second RF coil 28, and helmet 24.

The RF coil assembly 20 may further comprise additional structural components for packaging and protecting components of the RF coil assembly 20 such as cover 34, enclosure 36, and outer shell 38. Cover 34 may be coupled to helmet 24 and may serve as a stoppage point for the helmet 24 when the helmet 24 is inserted into the RF coil assembly 20, as described further herein. The enclosure 36 and outer shell 38 may serve to enclose and protect the components of the RF coil assembly 20, including, for example, electronic components such as the first and second RF coils 22, 28. The components of the RF coil assembly 20 may be coupled together by one or more fasteners, in some embodiments. In the illustrated embodiment, press fits 40, screws 42, and washers 44 couple components of the RF coil assembly 20.

As described further herein, the RF coil assembly 20 may be coupled to one or more other components (e.g., an MRI device, an infant support, etc.) via a coupling mechanism 30. The RF coil assembly 20 may be coupled to the coupling mechanism via any suitable fastener (e.g., one or more screws in the illustrated embodiment).

Figure 5B:
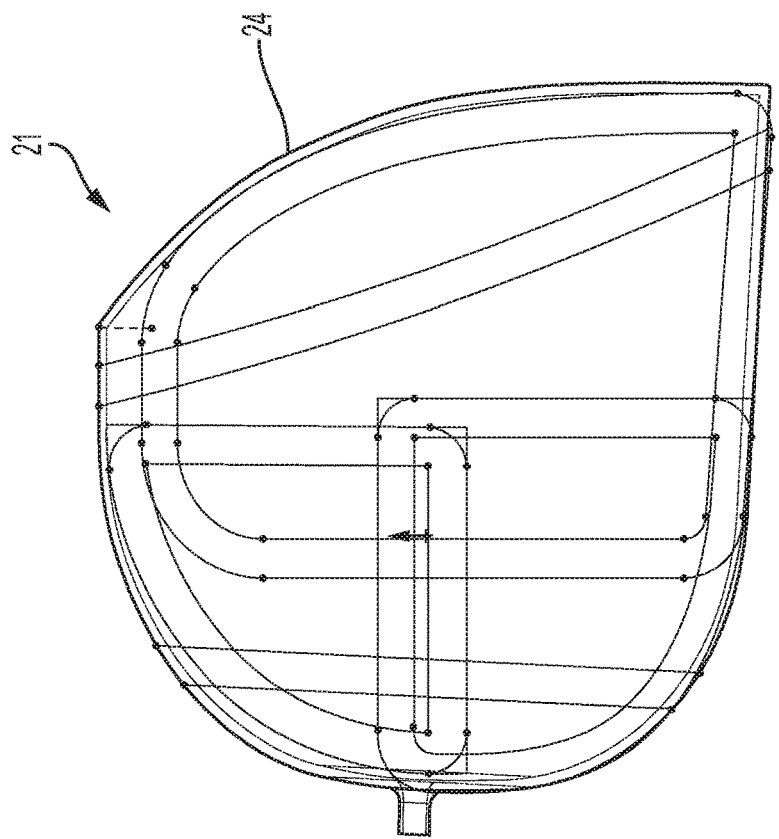
FIGS. 5A-5B are side views of example RF coil assemblies, in accordance with some embodiments of the technology described herein.
Figure 5A:
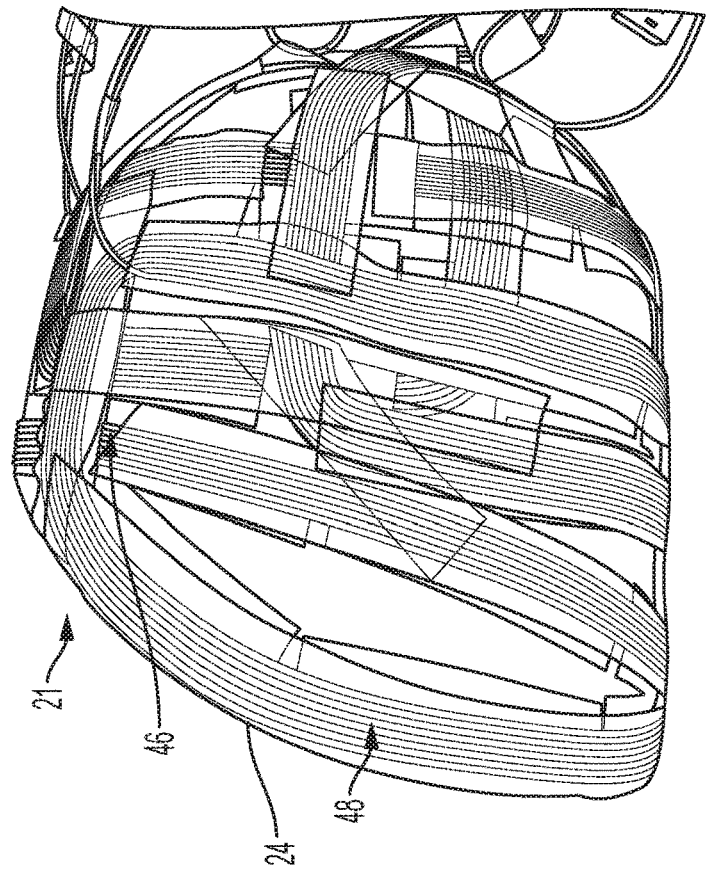

FIGS. 5A-5B are side views of example RF coil assemblies, in accordance with some embodiments of the technology described herein. FIGS. 5A-5B illustrate an alternative embodiment of the RF coil assembly shown in FIG. 1. The RF coil assembly 21 comprises at least one RF coil supported by a helmet 24. As shown in the illustrated embodiment, coil 46 is housed by the helmet 24. The coil 46 may be configured as one or more Tx coils, one or more Rx coils, and/or one or more Tx/Rx coils. Tape 48 is provided to keep the coil windings of the coil 46 positioned precisely.

Figure 6:
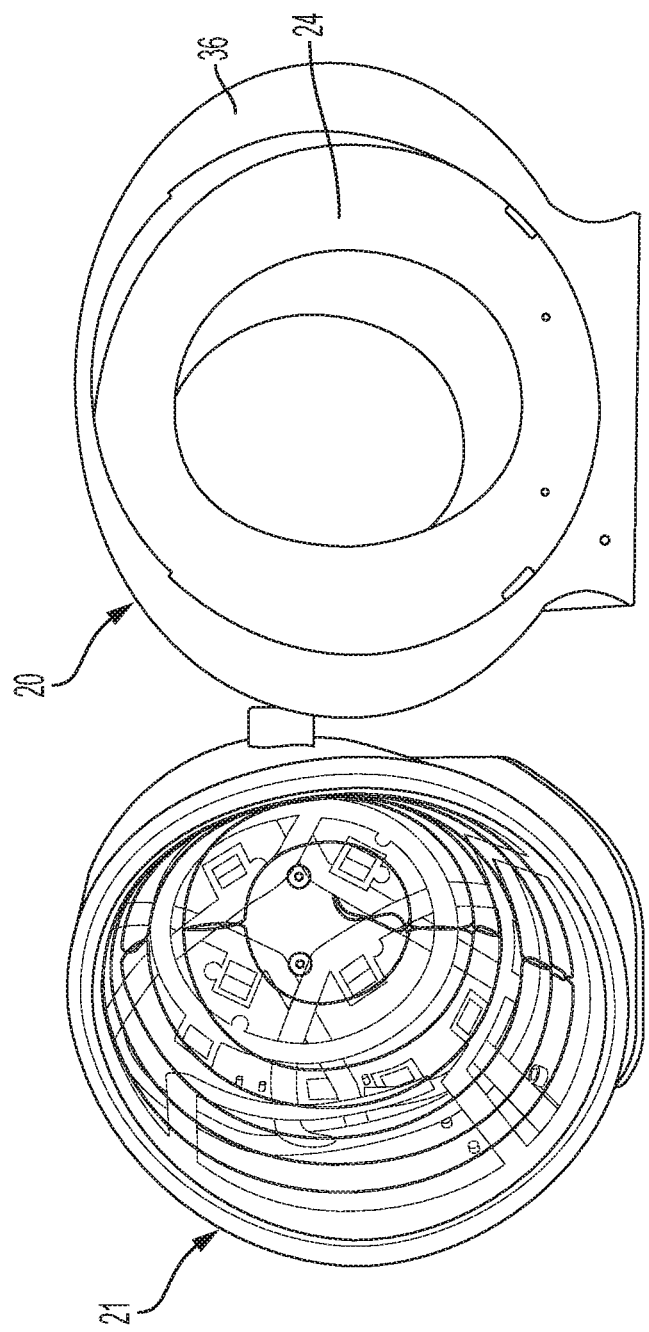
FIG. 6 illustrates front views of example RF coil assemblies in accordance with some embodiments of the technology described herein.

FIG. 6 illustrates front views of example RF coil assemblies in accordance with some embodiments of the technology described herein. As shown in FIG. 6, the RF coil assembly 21 comprises at least one RF coil housed inside a helmet whereas the RF coil assembly 20 comprises at least one RF coil disposed on or proximate to an exterior of the helmet 22. The RF coil assembly 20 comprises an enclosure 36 for supporting the components of the RF coil assembly 20.

In some embodiments, the RF coil assembly 20 may be configured for imaging infants (e.g., having a helmet 24 dimensioned to receive an infant's head) while the RF coil assembly 21 is configured for imaging adults. In particular, the RF coil assembly 21 may be dimensioned having an opening for receiving a patient's head therein that is large enough to accommodate an adult patient's head. Such dimensions may be too large to securely receive an infant's head without a significant amount of movement of the infant's head during imaging. As described herein, the inventors have developed an infant support having components which enable adaptation of an adult MRI device (e.g., an adult RF coil assembly) for use with infants, thus increasing the availability of MRI as an imaging modality for infants.

Figure 7A:
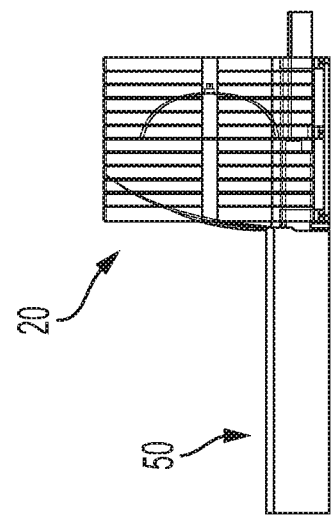
FIG. 7A is a side view of the example system of FIG. 1, in accordance with some embodiments of the technology described herein.
Figure 7B:
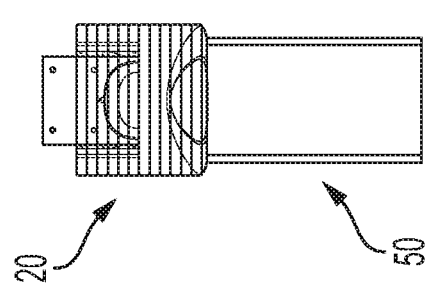
FIG. 7B is a top view of the example system of FIG. 1, in accordance with some embodiments of the technology described herein.

FIGS. 7A-7B illustrate additional views of the system 10. In particular, FIG. 7A is a side view of the example system of FIG. 1 and FIG. 7B is a top view of the example system of FIG. 1, in accordance with some embodiments of the technology described herein.

Figure 8:
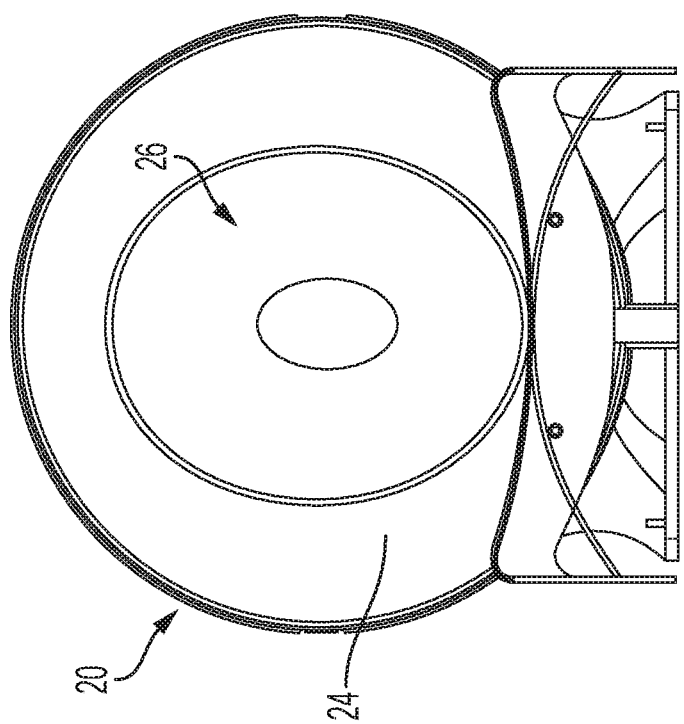
FIG. 8 is a front view of the example system of FIG. 1, in accordance with some embodiments of the technology described herein.

FIG. 8 further illustrates a front view of the example system of FIG. 1, in accordance with some embodiments of the technology described herein. FIG. 8 illustrates the opening 26 in the helmet 24 for receiving the infant's head therein. As described herein, the opening 26 may be suitably dimensioned for receiving an infant's head therein.

Figure 9:
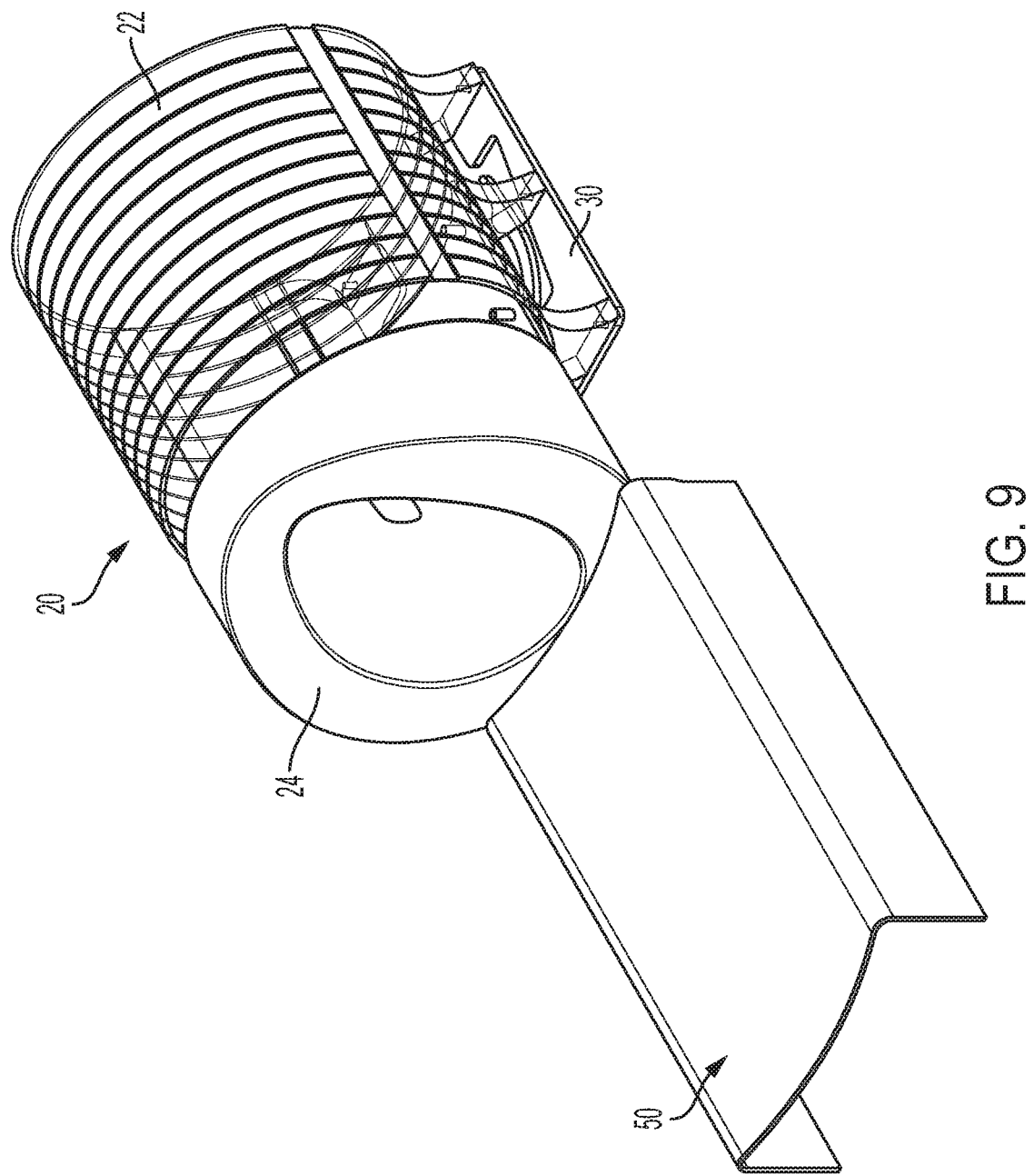
FIG. 9 is a perspective view of the example system of FIG. 1, with the helmet being removed from the RF coil assembly, in accordance with some embodiments of the technology described herein.

FIG. 9 is a perspective view of the example system of FIG. 1, with the helmet being removed from the RF coil assembly, in accordance with some embodiments of the technology described herein. As shown in the illustrated embodiment, the helmet 24 is removably coupled to the RF coil assembly 20. The infant support 50 is coupled to the helmet 24 such that the helmet 24 and infant support 50 move together at a same time. In an example method for positioning an infant relative to the RF coil assembly 20, the infant support 50 and the helmet 24 may be removed from an interior of the first RF coil 22 such that the infant can be positioned on the infant support 50 with at least a portion of the infant's head being disposed in the helmet 24. The helmet 24 and infant support 50 may be reinserted (e.g., by sliding the infant support 50 and helmet 24) into the interior of the first RF coil 22 when it is desired to perform imaging such that at least a portion of the first RF coil surrounds at least a portion of the infant's head.

The RF coil assembly 20 may comprise one or more components which provide a stopping point for the helmet 24 when it is inserted into the interior of the first RF coil 22. For example, the cover 34 of the RF coil assembly 20 may abut the helmet 24 when the helmet has been inserted into the interior of the first RF coil 22 to a maximum depth.

Figure 10A:
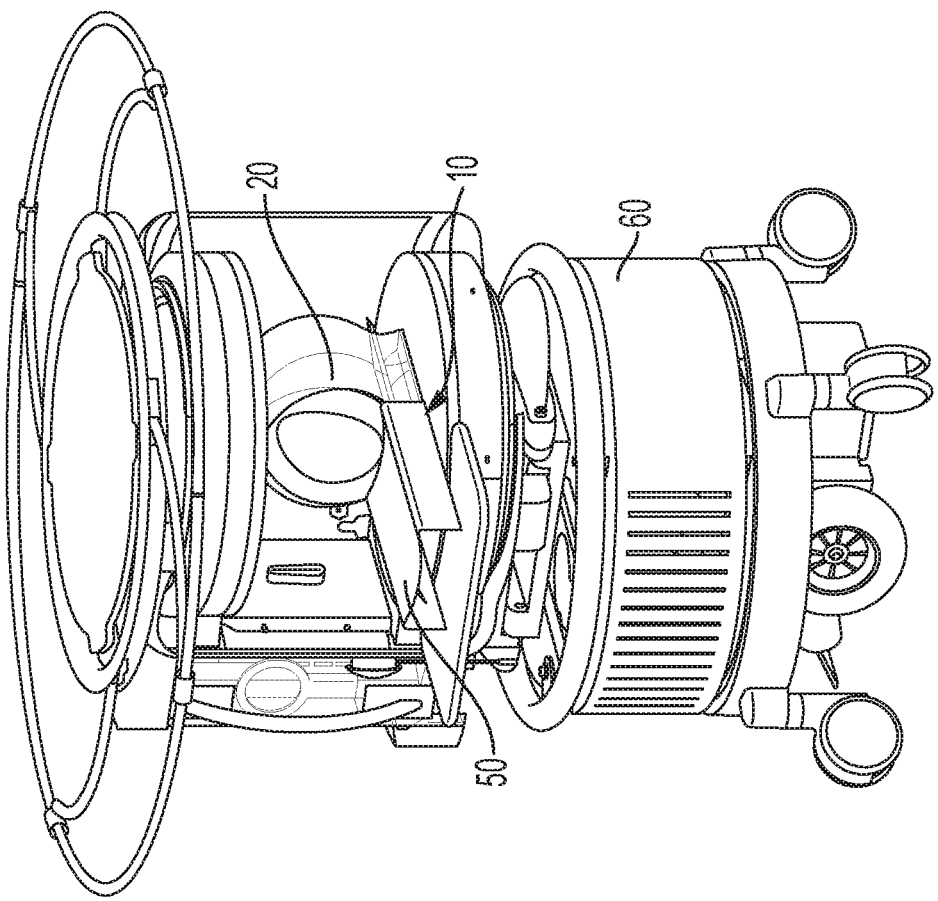
FIG. 10A a perspective view of the example system of FIG. 1 being coupled to an example MRI device, in accordance with some embodiments of the technology described herein.

In some embodiments, the system 10 may be used in combination with an MRI device to facilitate imaging of the infant. For example, FIG. 10A a perspective view of the example system 10 of FIG. 1 being coupled to an example MRI device 60, in accordance with some embodiments of the technology described herein. The MRI device may be any suitable device configured to facilitate magnetic resonance imaging of a patient, such as, for example, a portable low-field MRI system including any of the low-field MRI systems described in U.S. Pat. No. 10,222,434 ('434), titled "PORTABLE MAGNETIC RESONANCE IMAGING METHODS AND APPARATUS," filed Jan. 24, 2019 which is hereby incorporated by reference in its entirety herein.

Figure 10B:
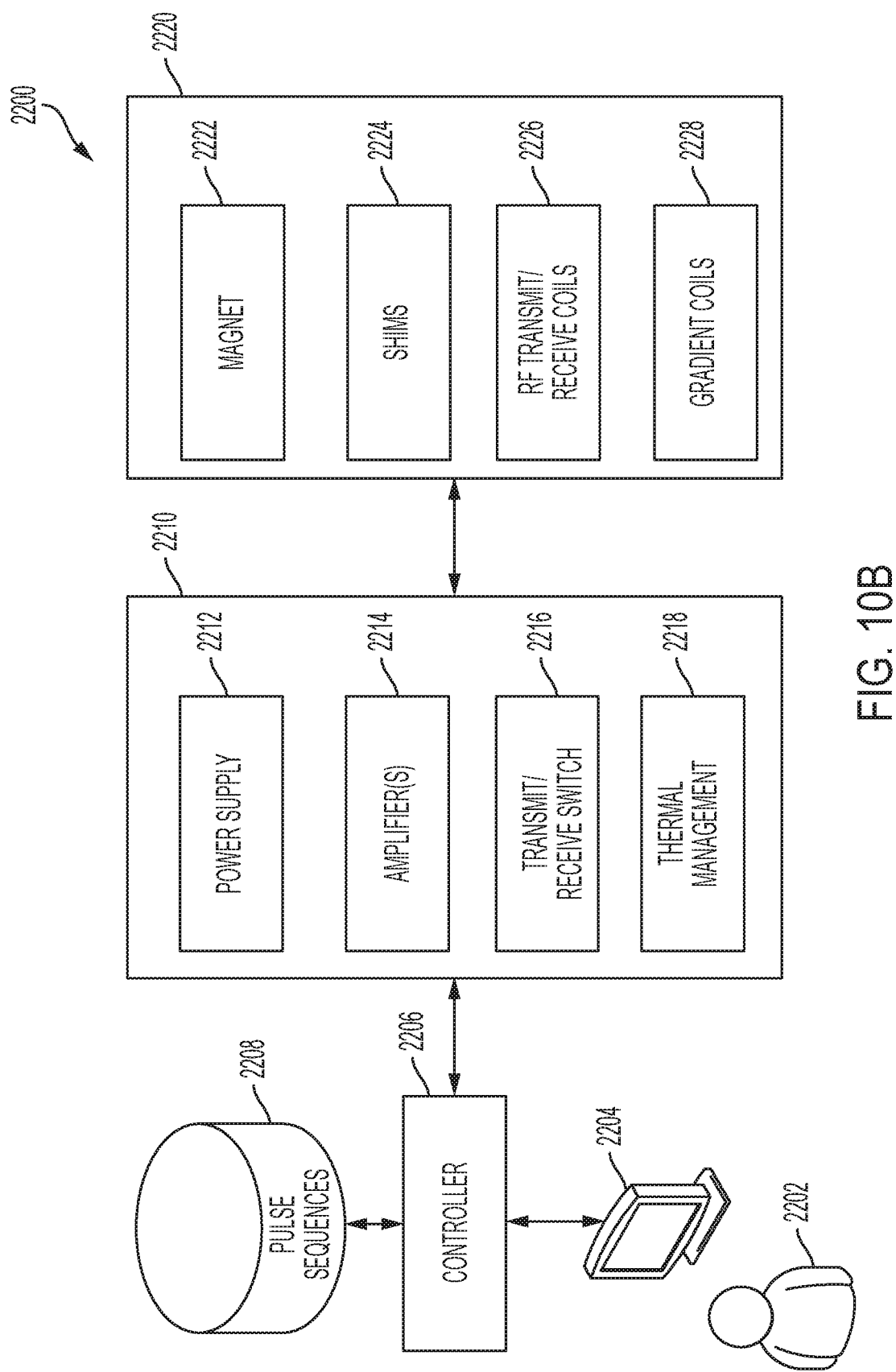
FIG. 10B is a block diagram of example components of an example MRI system, in accordance with some embodiments of the technology described herein.

In particular, MRI device 60 may form a part of all of an MRI system. FIG. 10B is a block diagram of example components of an example MRI system, in accordance with some embodiments of the technology described herein. In the illustrative example of FIG. 10B, MRI system 2200 comprises workstation 2204, controller 2206, pulse sequences store 2208, power management system 2210, and magnetic components 2220. It should be appreciated that system 2200 is illustrative and that an MRI system may have one or more other components of any suitable type in addition to or instead of the components illustrated in FIG. 10B.

As illustrated in FIG. 10B, magnetic components 2220 comprise $B_0$ magnet 2222, shims 2224, RF transmit and receive coils 2226, and gradient coils 2228. $B_0$ magnet 2222 may be used to generate, at least in part, the main magnetic field $B_0$. $B_0$ magnet 2222 may be any suitable type of magnet that can generate a main magnetic field, and may include one or more $B_0$ coils, correction coils, pole pieces, etc. In some embodiments, $B_0$ magnet 2222 may be a permanent magnet. For example, in some embodiments, $B_0$ magnet 2222 may comprise multiple permanent magnet pieces organized in a bi-planar arrangement of concentric permanent magnet rings. In some embodiments, $B_0$ magnet 2222 may be an electromagnet. In some embodiments, $B_0$ magnet 2222 may be a hybrid magnet comprising one or more permanent magnets and one or more electromagnets.

In some embodiments, shims 2224 may be used to contribute magnetic field(s) to improve the homogeneity of the $B_0$ field generated by magnet 2222. In some embodiments, shims 2224 may be permanent magnet shims. In some embodiments, shims 2224 may be electromagnetic and may comprise one or more shim coils configured to generate a shimming magnetic field.

In some embodiments, gradient coils 2228 may be arranged to provide gradient fields and, for example, may be arranged to generate gradients in the magnetic field in three substantially orthogonal directions (X, Y, Z) to localize where MR signals are induced. In some embodiments, one or more magnetics components 2220 (e.g., shims 2224 and/or gradient coils 2228) may be fabricated using the laminate techniques.

In some embodiments, RF transmit and receive coils 2226 may comprise one or multiple transmit coils that may be used to generate RF pulses to induce a magnetic field B 1. The transmit/receive coil(s) may be configured to generate any suitable type of RF pulses configured to excite an MR response in a subject and detect the resulting MR signals emitted. RF transmit and receive coils 2226 may include one or multiple transmit coils and one or multiple receive coils. The configuration of the transmit/receive coils varies with implementation and may include a single coil for both transmitting and receiving, separate coils for transmitting and receiving, multiple coils for transmitting and/or receiving, or any combination to achieve single channel or parallel MRI systems. In some embodiments, RF transmit and receive coils 2226 include multiple RF coils, which allow the MRI system 2200 to concurrently receive MR signals on multiple channels. In some embodiments, the MR signals received by multiple RF coils may be processed and combined.

Power management system 2210 includes electronics to provide operating power to one or more components of the low-field MRI system 2200. For example, power management system 2210 may include one or more power supplies, gradient power amplifiers, transmit coil amplifiers, and/or any other suitable power electronics needed to provide suitable operating power to energize and operate components of the low-field MRI system 2200.

As illustrated in FIG. 10B, power management system 2210 comprises power supply 2212, amplifier(s) 2214, transmit/receive switch 2216, and thermal management components 2218. Power supply 2212 includes electronics to provide operating power to magnetic components 2220 of the low-field MRI system 2200. For example, in some embodiments, power supply 2212 may include electronics to provide operating power to one or more $B_0$ coils (e.g., $B_0$ magnet 2222 when it is an electromagnet) to produce the main magnetic field for the low-field MRI system, one or more shims 2224, and/or one or more gradient coils 1628. In some embodiments, power supply 2212 may be a unipolar, continuous wave (CW) power supply. Transmit/receive switch 2216 may be used to select whether RF transmit coils or RF receive coils are being operated.

In some embodiments, amplifier(s) 2214 may include one or more RF receive (Rx) pre-amplifiers that amplify MR signals detected by RF receive coil(s) (e.g., coils 2224), RF transmit (Tx) amplifier(s) configured to provide power to RF transmit coil(s) (e.g., coils 2226), gradient power amplifier(s) configured to provide power to gradient coil(s) (e.g., gradient coils 2228), and/or shim amplifier(s) configured to provide power to shim coil(s) (e.g., shims 2224 in embodiments where shims 2224 include one or more shim coils).

In some embodiments, thermal management components 2218 provide cooling for components of low-field MRI system 2200 and may be configured to do so by facilitating the transfer of thermal energy generated by one or more components of the low-field MRI system 2200 away from those components.

As illustrated in FIG. 10B, low-field MRI system 2200 includes controller 2206 (also referred to as a console) having control electronics to send instructions to and receive information from power management system 2210. Controller 2206 may be configured to implement one or more pulse sequences, which are used to determine the instructions sent to power management system 2210 to operate the magnetic components 2220 according to a desired sequence. In some embodiments, controller 2206 may be configured to implement a pulse sequence by obtaining information about the pulse sequence from pulse sequences repository 2208, which stores information for each of one or more pulse sequences. Information stored by pulse sequences repository 2208 for a particular pulse sequence may be any suitable information that allows controller 2206 to implement the particular pulse sequence. Information stored in pulse sequences repository 2208 may be stored on one or more non-transitory storage media.

As illustrated in FIG. 10B, in some embodiments, controller 2206 may interact with computing device 2204 programmed to process received MR data (which, in some embodiments, may be spatial frequency domain MR data). For example, computing device 2204 may process received MR data to generate one or more MR images using any suitable image reconstruction process(es).

In some embodiments, a user 2202 may interact with computing device 2204 to control aspects of the low-field MR system 2200 (e.g., program the system 2200 to operate in accordance with a particular pulse sequence, adjust one or more parameters of the system 2200, etc.) and/or view images obtained by the low-field MR system 2200.

In some embodiments, for example where the $B_0$ magnet of the MRI device comprises first and second $B_0$ magnets organized in a bi-planar arrangement, the MRI device 60 comprises a c-shaped ferromagnetic yoke configured to capture and channel magnetic flux to increase the magnetic flux density within an imaging region (field of view) of the MRI device.

$B_0$ magnets of the MRI devices described herein may be configured to produce a $B_0$ magnetic field in the very low field strength regime (e.g., less than or equal to approximately 0.2 T, 0.1 T, 50 mT, 20 mT, etc. or any field strength equal to or within the ranges listed herein). For example, a portable MRI device may be configured to operate at a magnetic field strength of approximately 64 mT, though any low-field strength may be used.

In some embodiments, the system 10 may be coupled to the MRI device 60. For example, the system 10 may be mechanically coupled to the MRI device 60 (e.g., using a coupling mechanism), as described herein. In some embodiments, the system 10 may be electrically coupled to the MRI device 60. For example, as described herein, the MRI device may comprise one or more power components configured to power a component of the system 10 (e.g., one or more components of the RF coil assembly 20, etc.). In some embodiments, the system 10 may be mechanically and electrically coupled to the MRI device 60.

Having thus described aspects of the system 10, further details of the infant support will now be provided. The infant support may be configured to support an infant during MR imaging. For example, the infant support may be dimensioned and/or shaped to support the body of an infant. In some embodiments, the infant support may include components for facilitating positioning and alignment of the infant relative to the RF coil assembly and/or the MRI device, for example, by coupling to components of the RF coil assembly and/or the MRI device. In some embodiments, the infant support may include components for increasing comfort and restricting and/or minimizing movement of the infant during imaging. In some embodiments, the infant support includes components that facilitate MR imaging of an infant with the use of an MRI device configured for adults.

Figure 11:
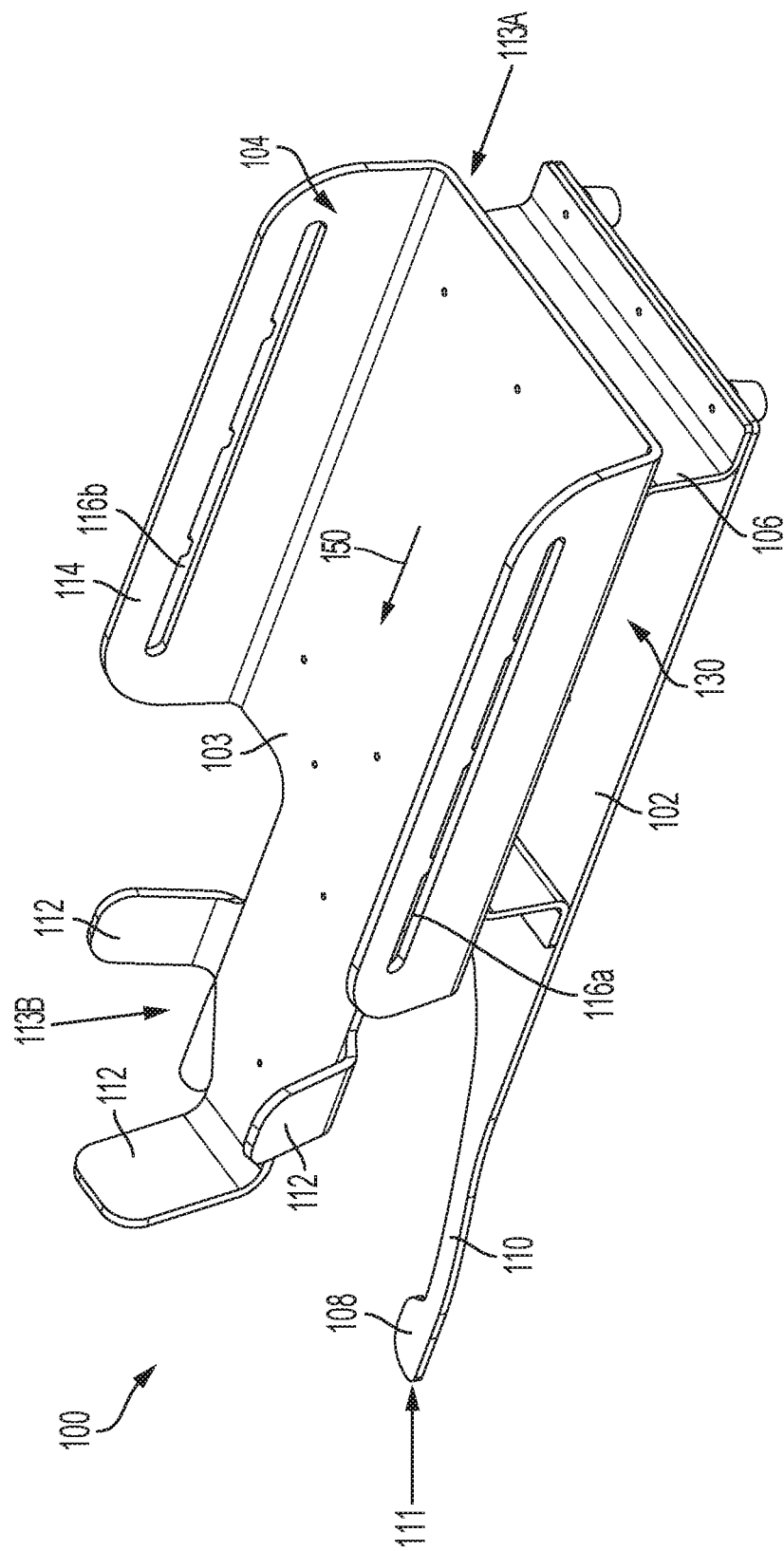
FIG. 11 is a perspective view of an example infant support, in accordance with some embodiments of the technology described herein.

FIG. 11 is a perspective view of an example infant support, in accordance with some embodiments of the technology described herein. As shown in FIG. 11, the infant support 100 comprises a base 102 and a tray 104 supported by the base 102. A bridge 106 of the infant support couples the base 102 to the tray and provides a gap 130 between the base 102 and the tray 104. As described herein, an infant may be positioned on the infant support 100 (e.g., on the tray 104), and the infant support 100 may facilitate positioning the infant relative to an RF coil assembly and/or an MRI device for imaging. For example, in some embodiments, the infant support facilitates positioning an infant relative to a helmet of the RF coil assembly. In some embodiments, the infant support 100 is configured to securely couple to a coupling mechanism to precisely position the infant relative to the RF coil assembly and/or the MRI device and prevent inadvertent movement of the infant support 100 during image acquisition.

An infant may be positioned on a surface 103 of the tray 104 in preparation for MR imaging. In particular, the infant may be placed on the surface 103 along a longitudinal axis 150 extending along a length of the tray 104. As shown in FIG. 11, the surface 103 is shaped so as to conform to the infant's body, for example, having a distal end 113B for supporting the infant's head, and a proximal end 113A for supporting the infant's body and feet. The distal end 113B of the surface 103 supporting the infant's head is tapered to better support the infant's head and minimize movement of the infant. In some embodiments, the infant may be placed on the surface 103 of the tray 104 prior to imaging when it is desired to perform image acquisition. In other embodiments, the tray 104 and infant support 100 may be configured as a portion of an infant's crib so that the infant need not be removed from the tray 104 for imaging.

As shown in FIG. 11, the tray 104 comprises sides 114 extending upwards from the surface 103 of the tray 104 for securely maintaining the infant on the tray 104 without risk of the infant falling out of the tray 104. The tray 104 further comprises tabs 112 coupled to the surface 103 at the distal end 113B, For example, the tabs 112 may support the infant's head to minimize movement of the infant's head during positioning and imaging. The tabs 112 may further contact interior sides of a helmet of the RF coil assembly when the infant support 100 is positioned for imaging. Contact between the tabs 112 and the helmet of the RF coil assembly may reduce movement of the infant support 100 relative to the RF coil assembly during imaging. Although in the illustrated embodiment, the tray 104 comprises three tabs 112, any suitable number of tabs 112 may be used to support the infant's head.

The sides 114 may prevent lateral movement of the infant during positioning and imaging. Although in the illustrated embodiment the sides 114 are shown extending the length of the tray 104, in some embodiments, sides 114 may not fully extend to the distal end 113B of the surface 103 of the tray 104.

The sides 114 and tabs 112 may be manufactured having any suitable height, for example, approximately two inches, approximately three inches, approximately four inches, approximately five inches, any height between approximately two inches and approximately five inches, etc., to prevent the infant from falling out of the tray 104. In some embodiments, the tabs 112 and sides 114 are manufactured having the same height, while in other embodiments, the tabs 112 and sides 114 have different heights.

In the illustrated embodiment, the sides 114 comprise slots 116. Slots 116 may receive a restraint (e.g., a strap) for wrapping around the top of the infant's body, to secure the infant to the tray and limit movement of the infant during positioning and imaging. For example, a restraint may pass through a first slot 116a on a left side of the tray 104, pass across the infant's body, and be received in a second slot 116b on a right side of the tray 104, opposite the first slot 116a. Any suitable number of slots 116 and restraints may be implemented with the infant support 100. In the illustrated embodiment, four slots 116 are shown in each side 114 of the tray 104 for receiving four restraints. In some embodiments, not all of the slots 116 receive restraints. For example, in some embodiments, it may be desirable to use less restraints depending on a size of the infant. In some embodiments, additional restraints may be implemented in addition or alternative to the restraints received by the slots 116. In some embodiments, the restraints are adjustable, for example, to account for patients of different sizes.

In some embodiments, the tray 104 includes one or more sensors (not shown). For example, the tray 104 may comprise at least one sensor for detecting movement of the infant and/or movement of the tray 104. In particular, one or more motion sensors may be used to detect motion of an infant supported by the tray 104 to determine whether the infant has become incorrectly positioned relative to the RF coil assembly and/or MRI device without having to visually check the infant's position. Further, in some embodiments, the tray 104 comprises imaging electronics for imaging at least a portion of the patient supported by the tray 104.

As shown in FIG. 11, the tray 104 is coupled to the base 102 by a bridge 106. In some embodiments, one or more fasteners (e.g., one or more screws) couple the tray 104 to the bridge 106, and one or more fasteners (e.g., one or more screws) couple the bridge 106 to the base 104. Threaded inserts may be used to facilitate coupling components of the infant support 100 via screws, and to cover sharp edges of the screws. Although in the illustrated embodiment one or more screws are used to couple components of the infant support 100 together, any suitable manner of coupling may be used, for example, welding, soldering, adhesives, etc. In some embodiments, part or all of the infant support 100 is shaped from a single piece of material.

The bridge 106 provides a gap 130 providing a vertical offset between the base 102 and the tray 104, such that the tray 104 is positioned at approximately the same height as a helmet of the RF coil assembly, and the base 102 is positioned at approximately the same height as a coupling mechanism coupled to the RF coil assembly. Thus, an infant placed on the tray 104 can be positioned within an opening of the RF coil assembly for imaging while the base 102 is coupled to the coupling mechanism.

As described herein, the infant support 100 may facilitate positioning an infant relative to a RF coil assembly while minimizing movement of the infant and infant support 100. In some embodiments, positioning of the infant support is facilitated by the base 102 and its components. For example, the base 102 comprises a pair of elongated arms 110 on each side of the base 102. The arms 110 extend outwards from the base 102 in a direction along the longitudinal axis. For example, the arms 110 extend outwards towards the RF coil assembly in the direction of insertion of the infant into the RF coil assembly. Each arm 110 comprises a snap 108 at a distal end 111 of the arm 110 for receiving by a coupling mechanism coupled to the RF coil assembly. The snaps 108 may facilitate secure positioning of the infant support 100 relative to the RF coil assembly, as further described herein. In addition, the snaps 108 may be configured such that the infant support 100 can be removed from the RF coil assembly by pulling on the infant support 100 in a direction opposite the insertion direction. The pulling force required to remove the infant support 100 from the RF coil assembly may be relatively small to enable removal of the infant support 100 from the RF coil assembly when desired, while still being large enough to prevent inadvertent movement of the infant support 100 during imaging, as described herein.

Figure 12:
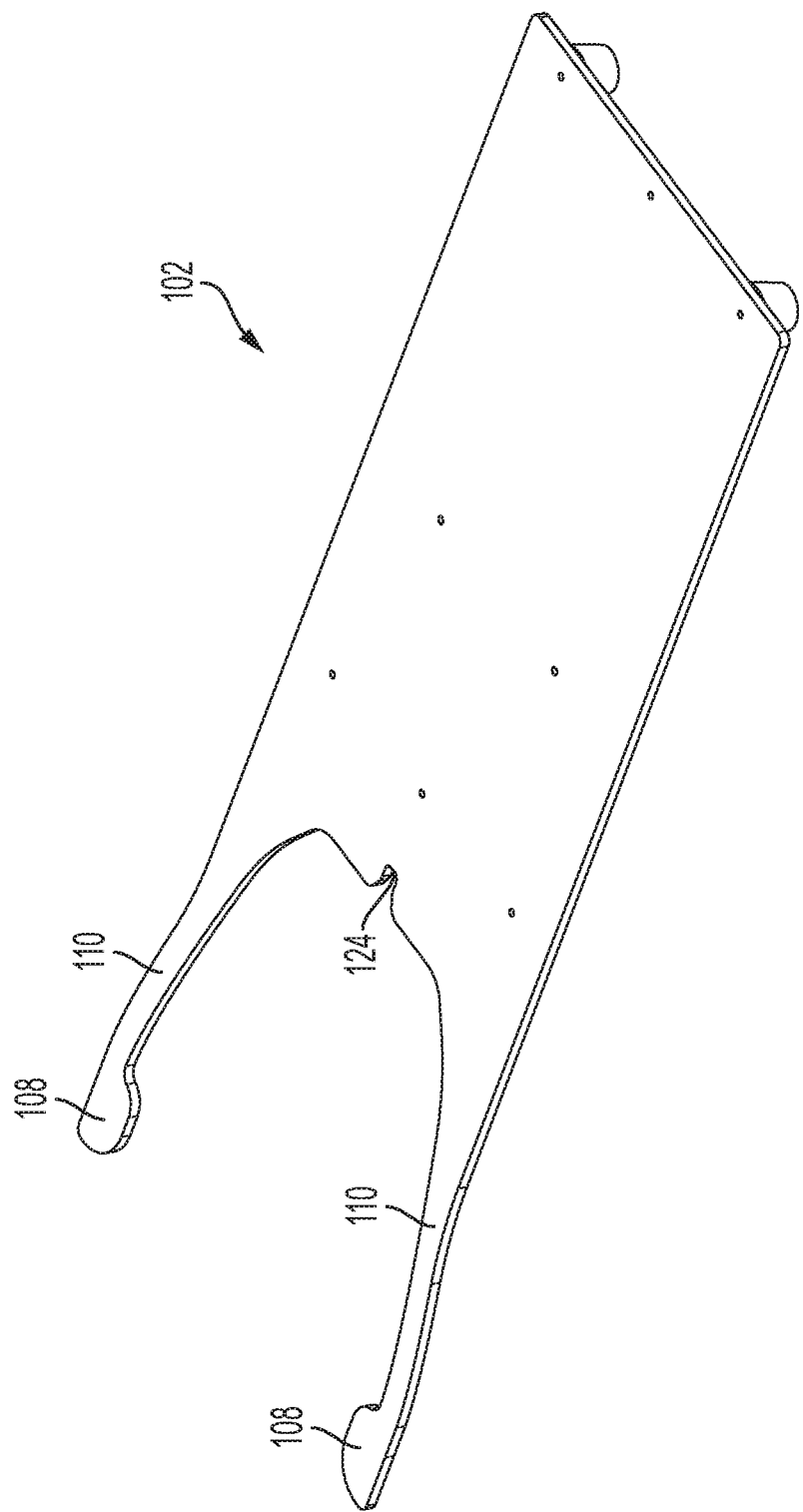
FIG. 12 is a perspective view of a base of the example infant support of FIG. 11, in accordance with some embodiments of the technology described herein.

FIG. 12 is a perspective view of a base of the example infant support of FIG. 11, in accordance with some embodiments of the technology described herein. As shown in FIG. 12 and further illustrated herein, the arms 110 slope upward in a direction along the longitudinal axis (e.g., along the direction of insertion of the infant into the RF coil assembly) such that the snaps 108 are elevated with respect to the base 102. The sloped incline of the arms 110 facilitate insertion of the base 102 into a coupling mechanism coupled to the RF coil assembly, as described herein.

FIG. 12 further illustrates the base 102 of the infant support 100 having a notch 124. The notch 124 is shaped to receive a protrusion of a coupling mechanism coupled to the RF coil assembly complementary to the notch, as described herein. Although in the illustrated embodiment the infant support 100 comprises a notch to receive a complementary protrusion of a coupling mechanism, in some embodiments, the infant support 100 comprises a protrusion to be received by a complementary notch of a coupling mechanism coupled to the RF coil assembly.

Figure 13:
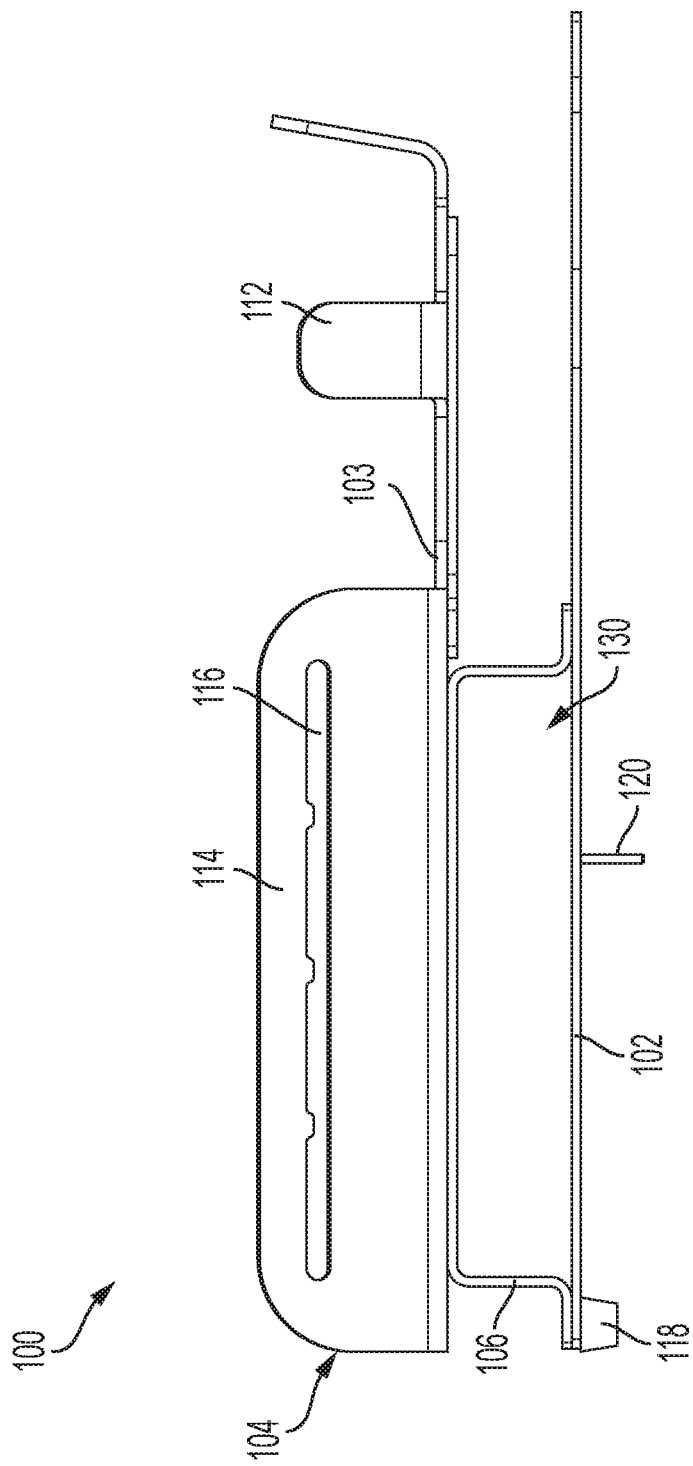
FIG. 13 is a side view of the example infant support of FIG. 11, in accordance with some embodiments of the technology described herein.

FIG. 13 is a side view of the example infant support of FIG. 11, in accordance with some embodiments of the technology described herein. As shown in FIG. 13, the infant support 100 further comprises a pair of feet 118 coupled to and extending downwards from the base 102 of the infant support 100. The feet 118 may level the infant support 100 relative to the RF coil assembly. For example, as described herein, positioning the infant support 100 relative to the RF coil assembly may be facilitated with use of an inclined ramp to slide the infant support 100 into position. The feet 118 are arranged to level the infant support 100 relative to the RF coil assembly such that the infant support 100 is not positioned at an incline during insertion or imaging, which could otherwise increase the risk of the infant changing position or falling out of the tray 104 during imaging. The feet 118 may also have a relatively high coefficient of friction to reduce back sliding of the infant support 100 along the inclined ramp. Although in the illustrated embodiment the infant support comprises a pair of feet, the infant support may have any suitable number of feet disposed at any suitable position.

FIG. 13 further shows infant support 100 having a pair of pins 120 coupled to and extending downward from the base 102 of the infant support 100. The pins 120 may prevent the infant support 100 from being inserted too far into the RF coil assembly. For example, the pins 120 may abut a base of the MRI device when the infant support is fully inserted into the RF coil assembly.

In some embodiments, the pins 120 may also prevent the infant support 100 from being removed from the RF coil assembly inadvertently. For example, in some embodiments, the pins 120 may be received by a recess between a base of the MRI device and another component (e.g., the inclined ramp or support bridge, as described herein), such that the infant support 100 cannot be removed from the RF coil assembly inadvertently. In particular, the pins 120 may be manufactured having a height taller than the height of the feet 118. In some embodiments, the feet 118 have a height of approximately 1 inch and the pins 120 have a height of approximately 1¼ inches. In this way, in order to remove the infant support 100 from the RF coil assembly, the base 102 may be elevated slightly (e.g., at least ¼ inch in the described example) to remove the pins 120 from the recess between the MRI device base and other component. The feet 118 and pins 120 may have any suitable height such that an offset is provided between the feet 118 and the pins 120. However, in some embodiments, the feet 118 and the pins 120 have approximately the same height.

Figure 14:
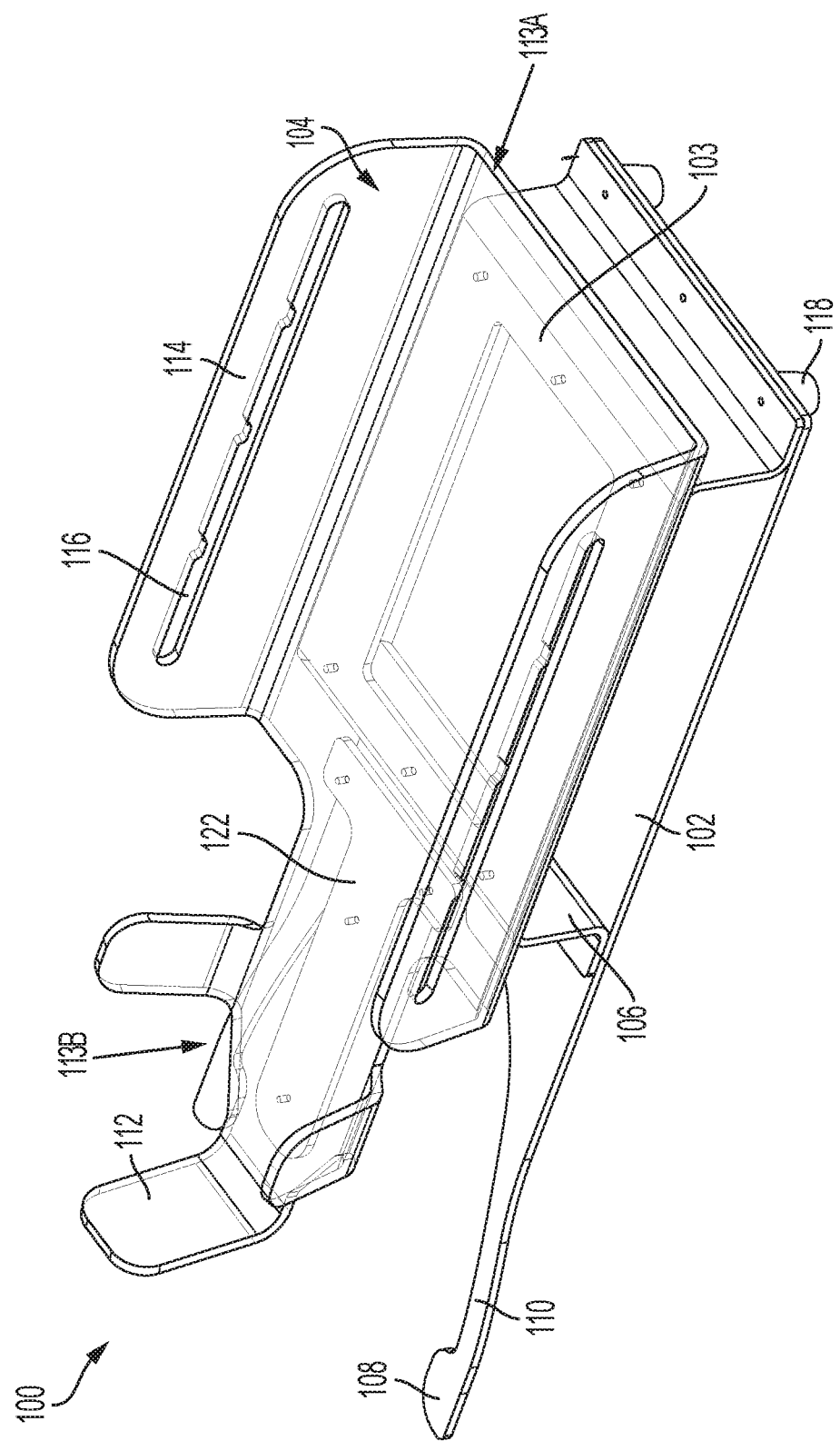
FIG. 14 is a perspective view of the example infant support of FIG. 11 with some portions of the infant support shown transparently, in accordance with some embodiments of the technology described herein.

FIG. 14 is a perspective view of the example infant support of FIG. 11 having some portions of the infant support shown transparently, in accordance with some embodiments of the technology described herein. As shown in FIG. 14, the infant support 100 comprises a surface 103 for supporting the body of the infant. The surface 103 is shaped for receiving the infant, for example, having a tapered shape such that a proximal end 113A of the surface 103 for supporting the lower body of the infant has a width greater than a width of a distal end 113B of the surface 103 for supporting the infant's head. Further, as shown in the illustrated embodiment, the proximal end 113A of the surface 103 is supported by the bridge 106, while the distal end 113B of the surface 103 is cantilevered. When an infant is placed on the tray 104, the cantilevered configuration of the tray 104 may not provide sufficient support for the infant's head as the weight of the infant may put the distal end of 113B of the surface 103 at risk of breaking. As such, a brace 122 is coupled to the distal end 113B of the surface 103 of the tray 104 to provide additional support for the tray 104. The brace 122 may be coupled below and/or above the surface 103.

Figure 15:
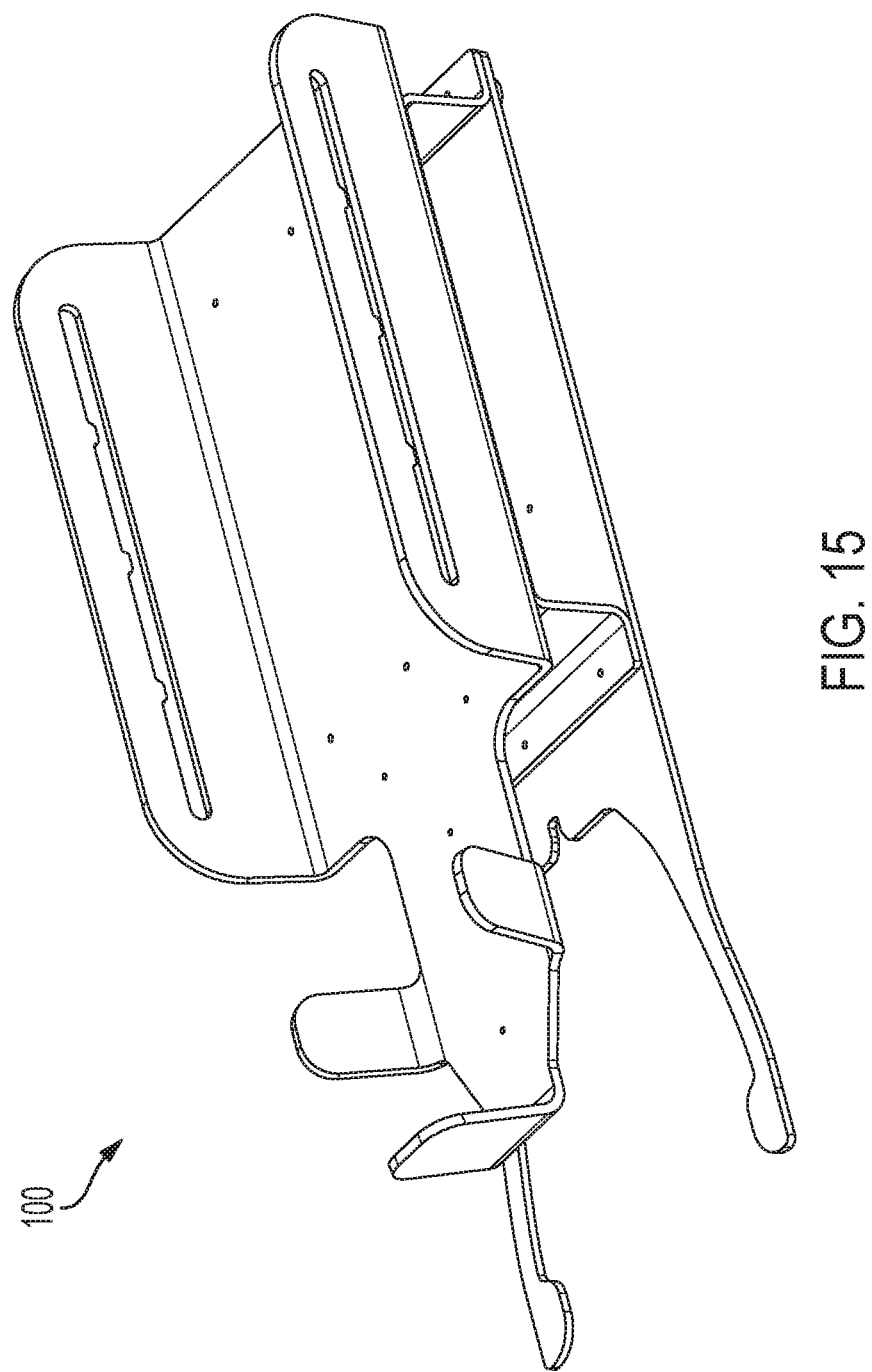
FIG. 15 is another perspective view of the example infant support of FIG. 11, in accordance with some embodiments of the technology described herein.
Figure 16:
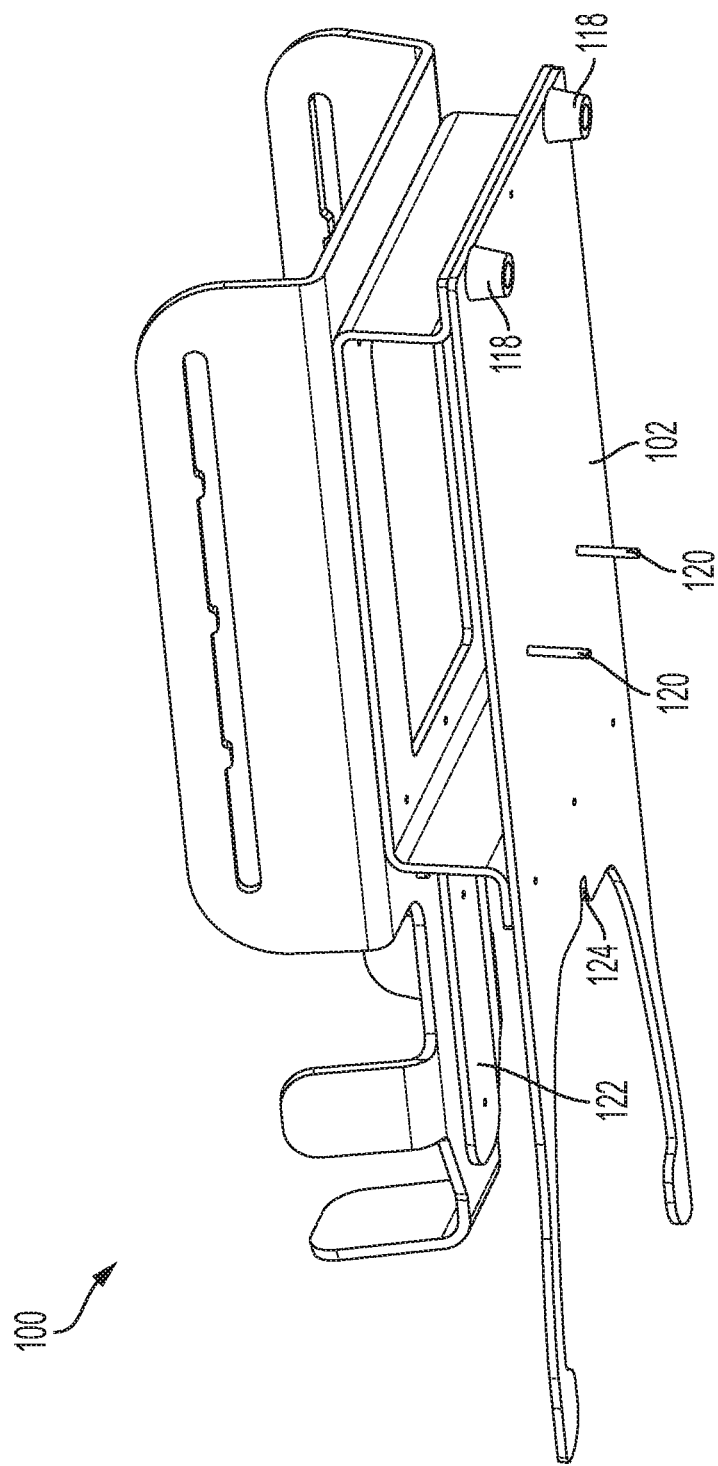
FIG. 16 is a partial bottom view of the example infant support of FIG. 11, in accordance with some embodiments of the technology described herein.

FIGS. 15-16 illustrate additional views of the example infant support 100. FIG. 15 is another perspective view of the example infant support of FIG. 11, in accordance with some embodiments of the technology described herein. FIG. 16 is a partial bottom view of the example infant support of FIG. 11, in accordance with some embodiments of the technology described herein.

Components of the infant support 100 may be manufactured using any suitable material. For example, in some embodiments, components of the infant support 100 (e.g., the base 102, the tray 104, the bridge 106, etc.) comprise plastic, e.g., DELRIN, polyethylene terephthalate glycol (PETG), high-density polyethylene (HDPE), acrylic, etc. In some embodiments, one or more components of the infant support 100 is additionally or alternatively made of one or more other materials, and aspects of the technology described herein are not limited in this respect.

Figure 17:
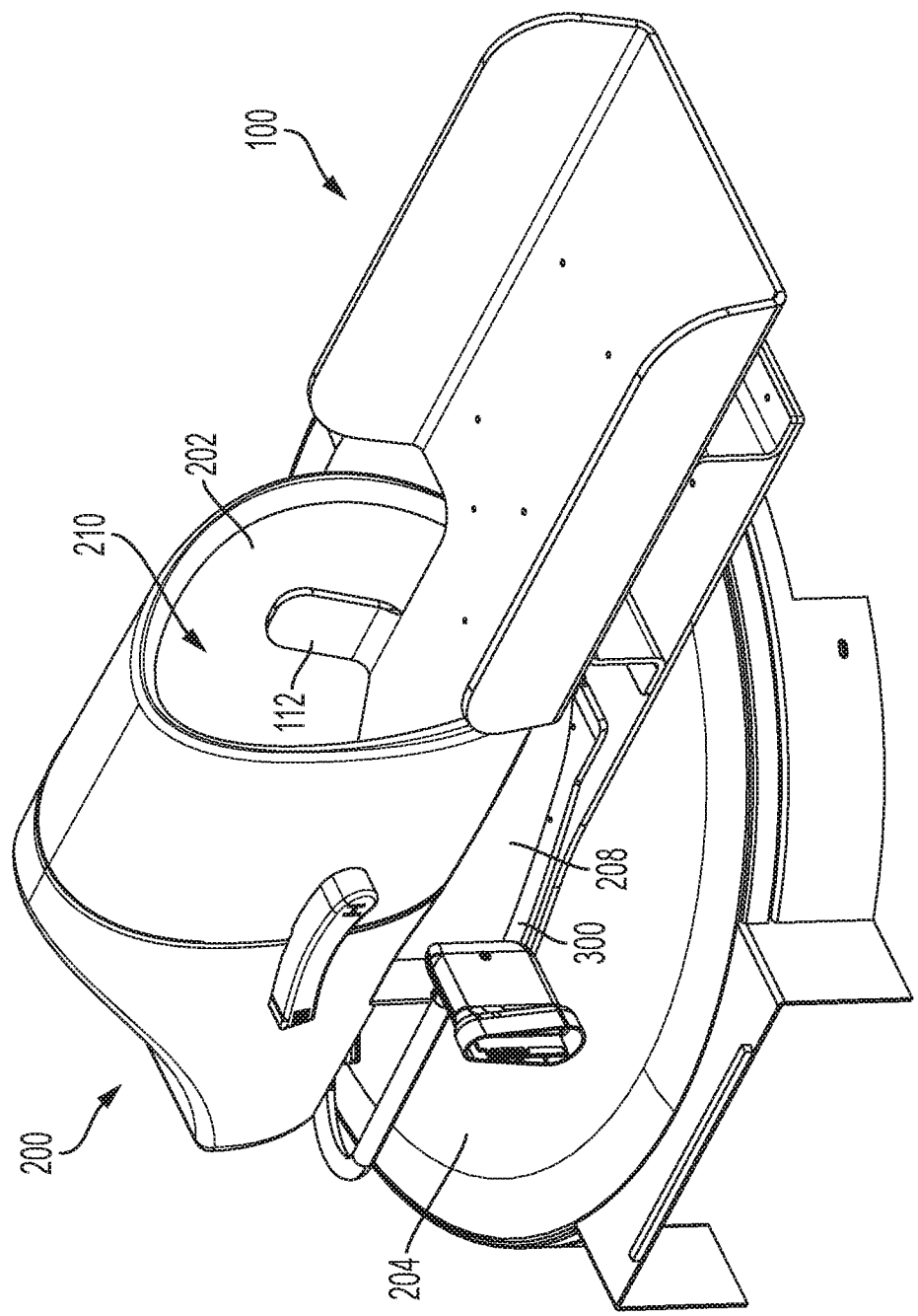
FIG. 17 is a perspective view of an example infant support coupled to an example RF coil assembly, in accordance with some embodiments of the technology described herein.

FIG. 17 is a perspective view of an example infant support coupled to an example RF coil assembly, in accordance with some embodiments of the technology described herein. As described herein, the infant support 100 facilitates positioning of an infant relative to an RF coil assembly, such as RF coil assembly 200 shown in FIG. 17, and/or an MRI device. As shown in FIG. 17, the RF coil assembly 200 comprises a helmet 202 and a helmet support 208. As described herein, the RF coil assembly 200 may have one or more transmit and/or receive coils. In the illustrated embodiment, the helmet supports the one or more transmit and/or receive coils (e.g., by housing the one or more transmit and/or receive coils, for example). In other embodiments, the one or more transmit and/or receive coils may be disposed on or proximate to the helmet 202. The one or more transmit and/or receive coils may facilitate MR imaging of a patient's head, for example, in combination with an MRI device. A helmet support 208 is provided for supporting the helmet 202 relative to the MRI device base 204.

According to an aspect of the technology described herein, a coupling mechanism 300 is provided for coupling the RF coil assembly 200 to an MRI device base 204 and for positioning the infant support 100 relative to the RF coil assembly 200. In particular, the coupling mechanism 300 is coupled to the MRI device base 204. The coupling mechanism 300 may be coupled to the MRI device base 204 by any suitable coupling means (e.g., screws, adhesive, soldering, welding, etc.). As described herein, the MRI device base 204 may comprise a helmet base (not shown) for coupling to the coupling mechanism 300. The helmet 202 is coupled to the coupling mechanism 300 by virtue of the helmet support 208, which may also be coupled to the coupling mechanism 300 by any suitable coupling means. In the illustrated embodiment, the helmet support 208 is coupled to the coupling mechanism 300 and the helmet 202 using screws. The coupling mechanism 300 may receive the infant support 100 (e.g., by receiving arms 110 and snaps 108, as described herein) so as to position the infant support 100 relative to the RF coil assembly 200 and prevent movement of the infant support 100 during imaging.

Figure 18:
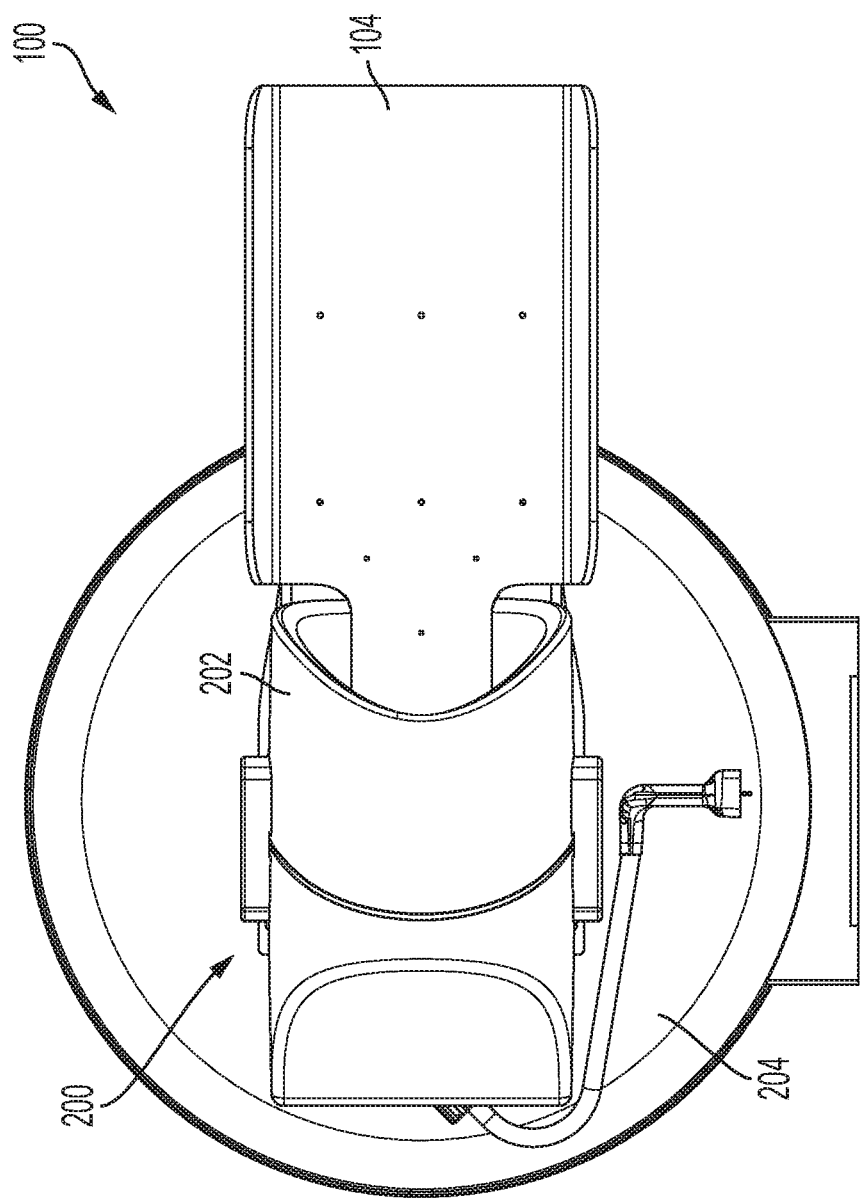
FIG. 18 is a top view of the example infant support and RF coil assembly of FIG. 17, in accordance with some embodiments of the technology described herein.
Figure 19:
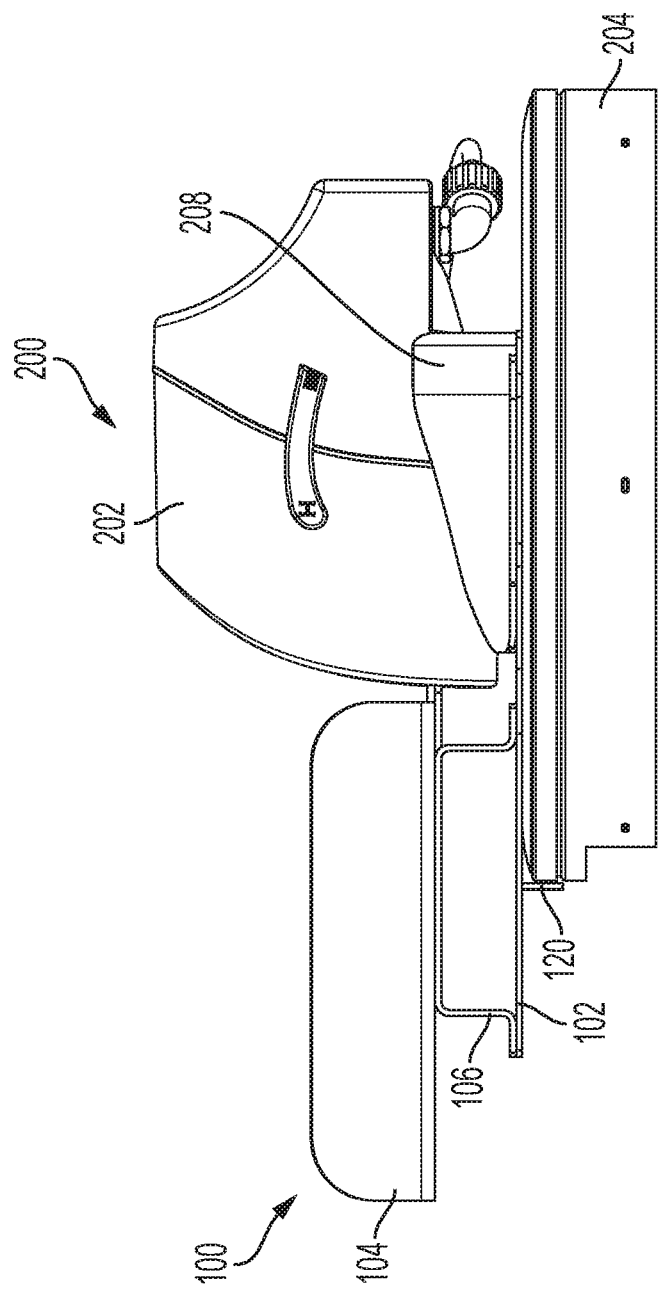
FIG. 19 is a side view of the example infant support and RF coil assembly of FIG. 17, in accordance with some embodiments of the technology described herein.
Figure 20:
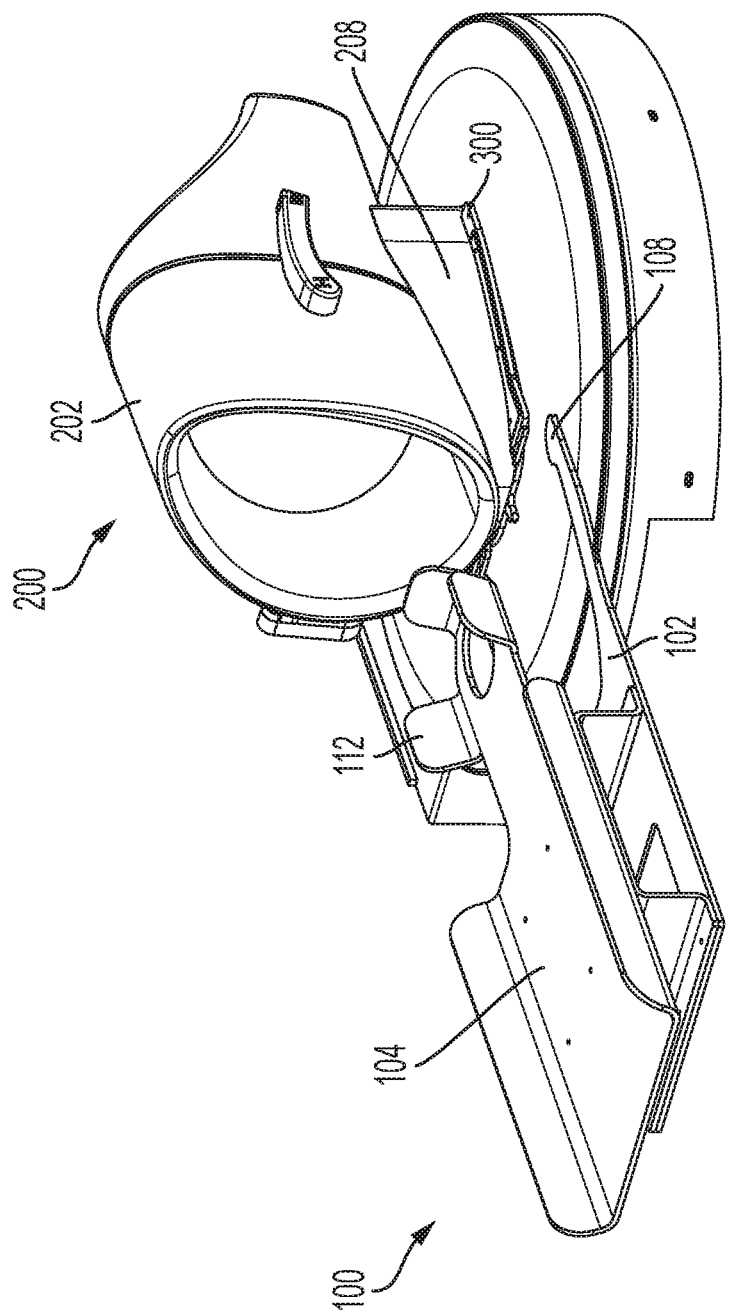
FIG. 20 is a perspective view of an example infant support and RF coil assembly shown during a positioning step for coupling the example infant support to the example RF coil assembly, in accordance with some embodiments of the technology described herein.
Figure 21:
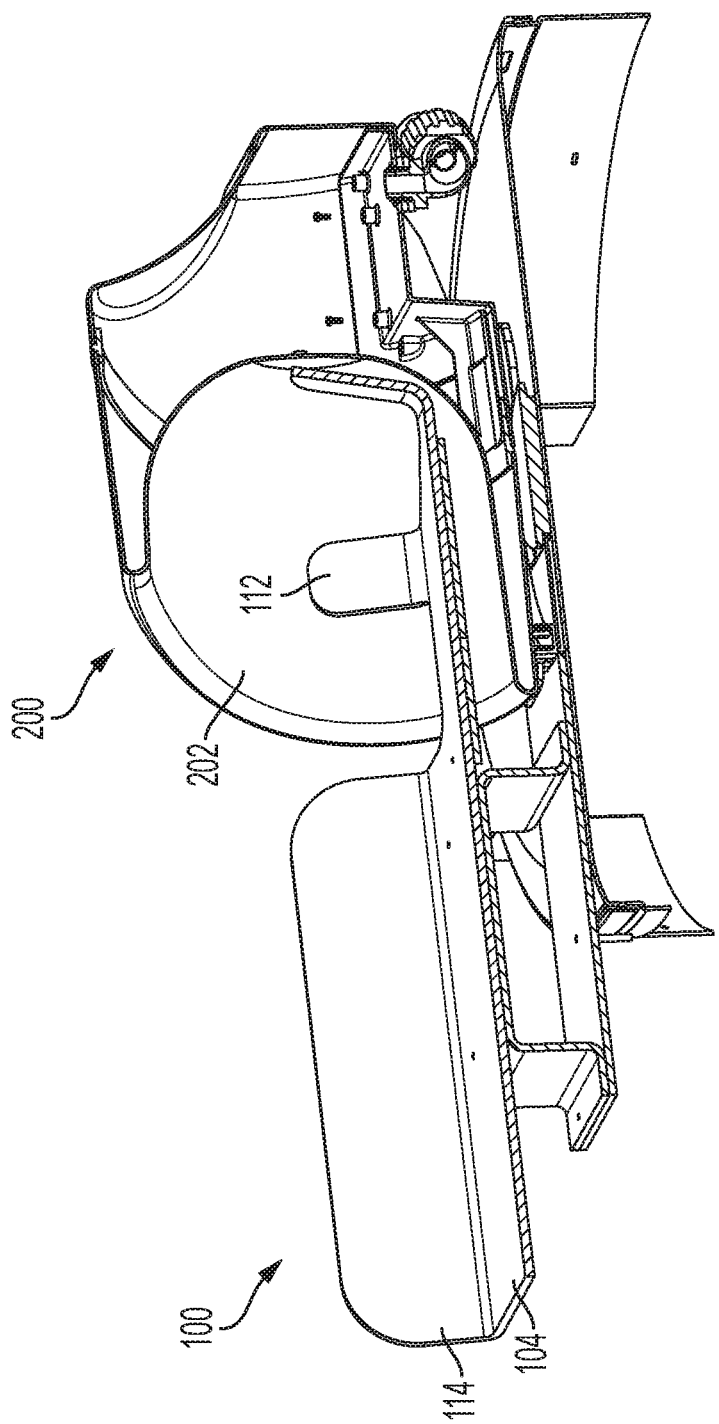
FIG. 21 is a cutaway view of an example infant support coupled to an example RF coil assembly, in accordance with some embodiments of the technology described herein.
Figure 22:
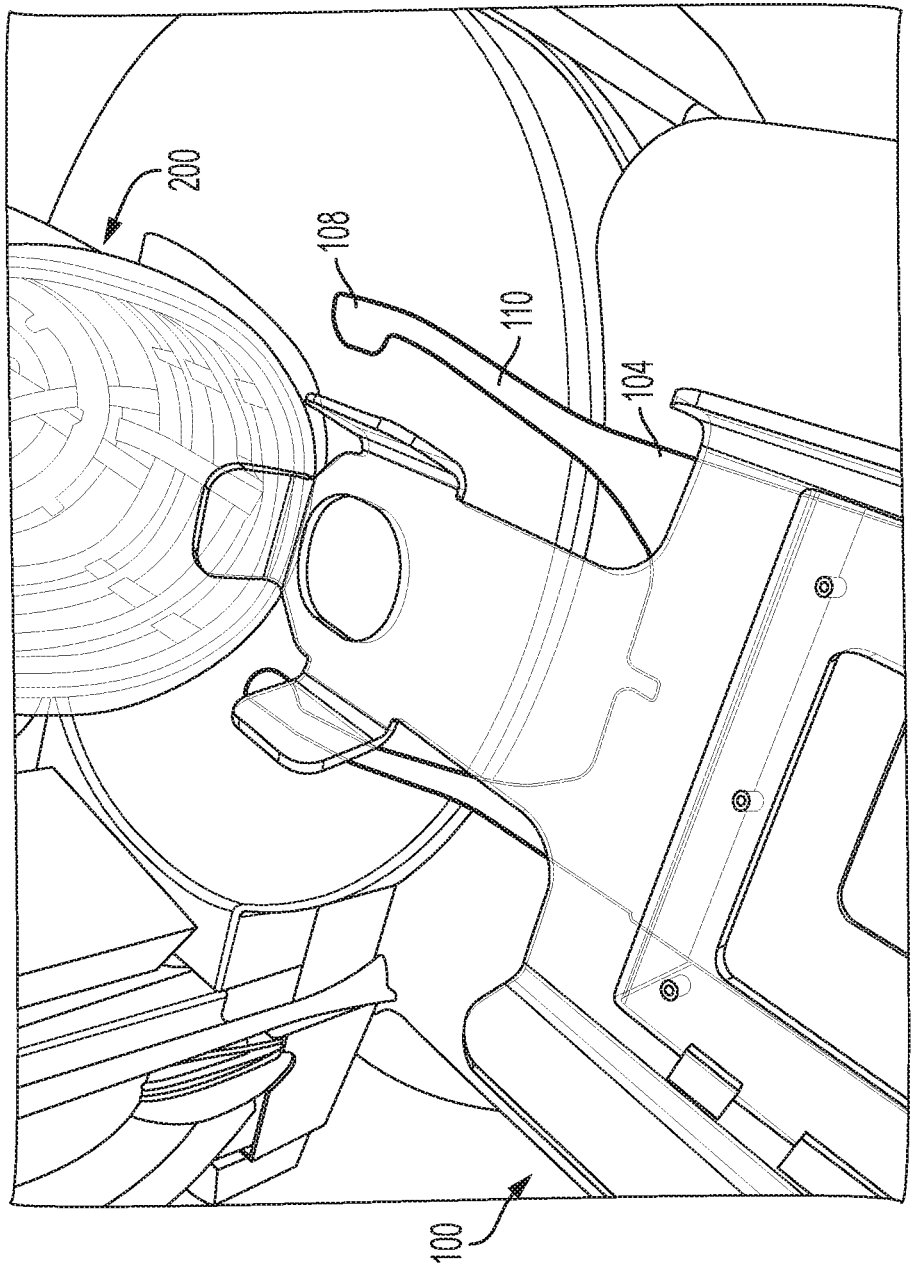
FIG. 22 is a partial top view of an example infant support and RF coil assembly, in accordance with some embodiments of the technology described herein.

FIGS. 18-22 illustrate additional aspects of the infant support 100 and RF coil assembly 200, including insertion of the base 102 of the infant support 100 into the coupling mechanism 300. For example, FIG. 18 is a top view of the example infant support and RF coil assembly of FIG. 17, in accordance with some embodiments of the technology described herein. FIG. 19 is a side view of the example infant support and RF coil assembly of FIG. 17, in accordance with some embodiments of the technology described herein. FIG. 20 is a perspective view of an example infant support and RF coil assembly shown during a positioning step for coupling the example infant support to the example RF coil assembly, in accordance with some embodiments of the technology described herein. FIG. 21 is a cutaway view of an example infant support coupled to an example RF coil assembly, in accordance with some embodiments of the technology described herein. FIG. 22 is a partial top view of an example infant support and RF coil assembly, in accordance with some embodiments of the technology described herein.

Figure 23:
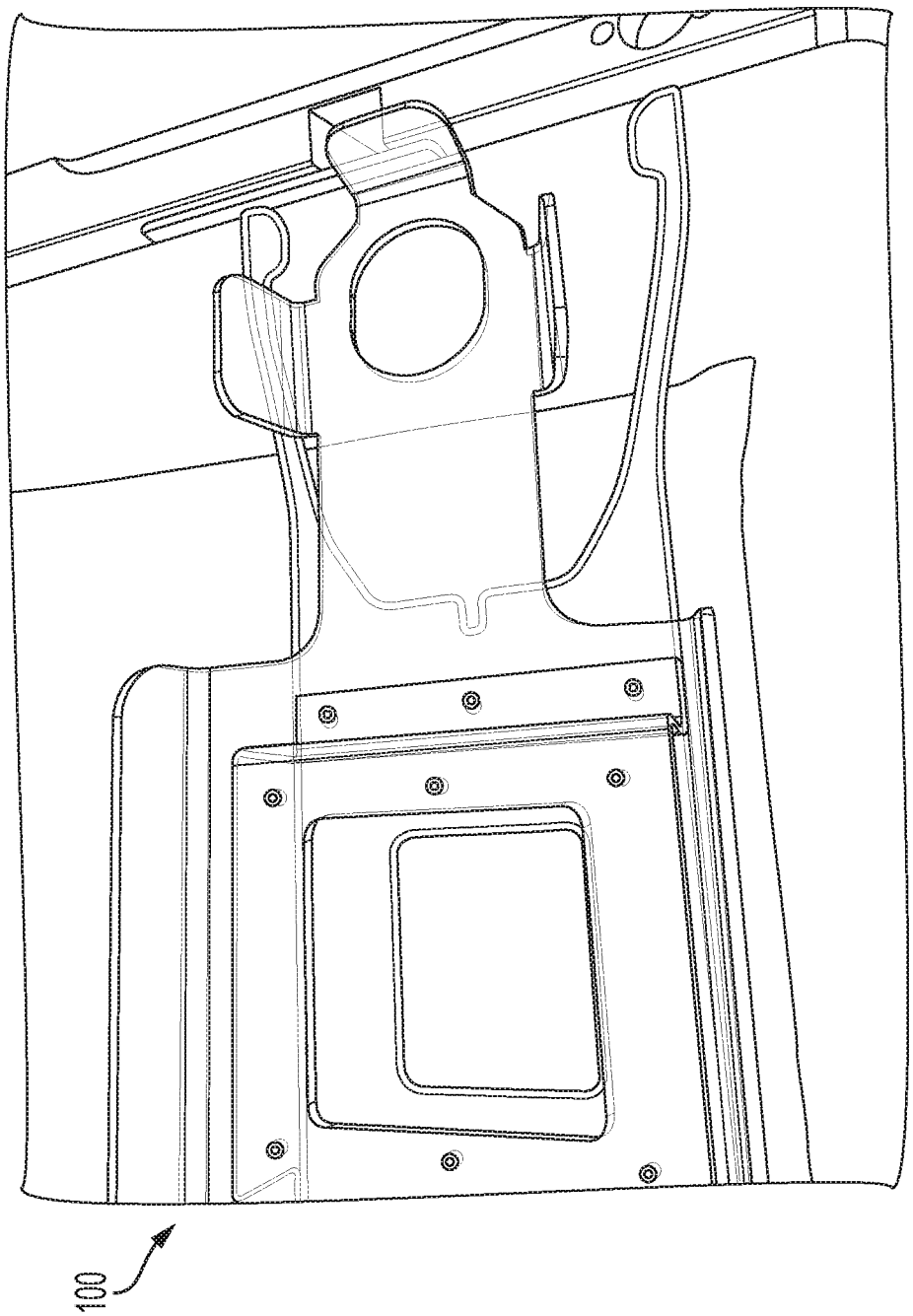
FIG. 23 is a partial top view of the example infant support of FIG. 22, in accordance with some embodiments of the technology described herein.
Figure 24:
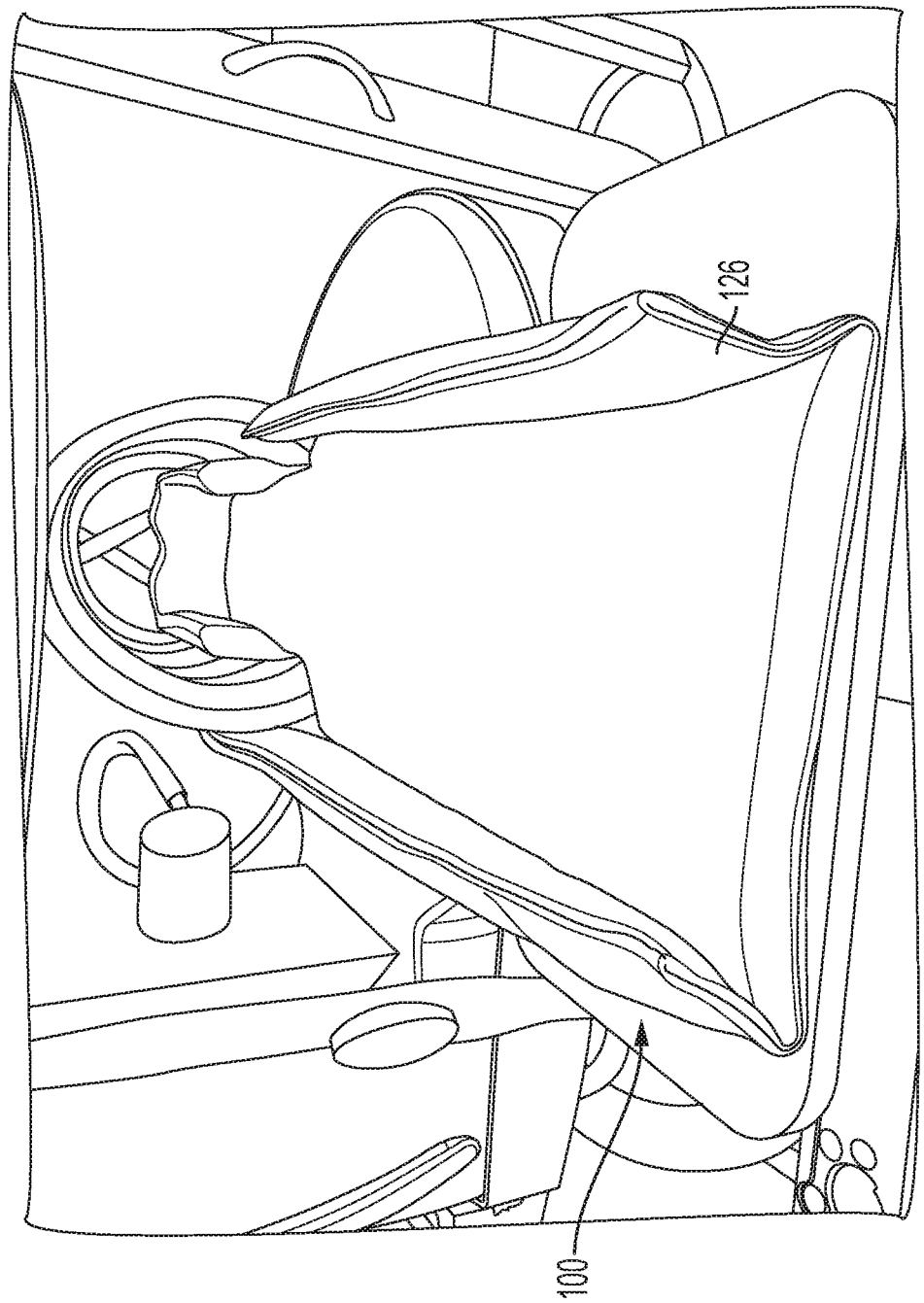
FIG. 24 is a partial front view of an example infant support coupled to an example RF coil assembly, the example infant support having padding, in accordance with some embodiments of the technology described herein.
Figure 25:
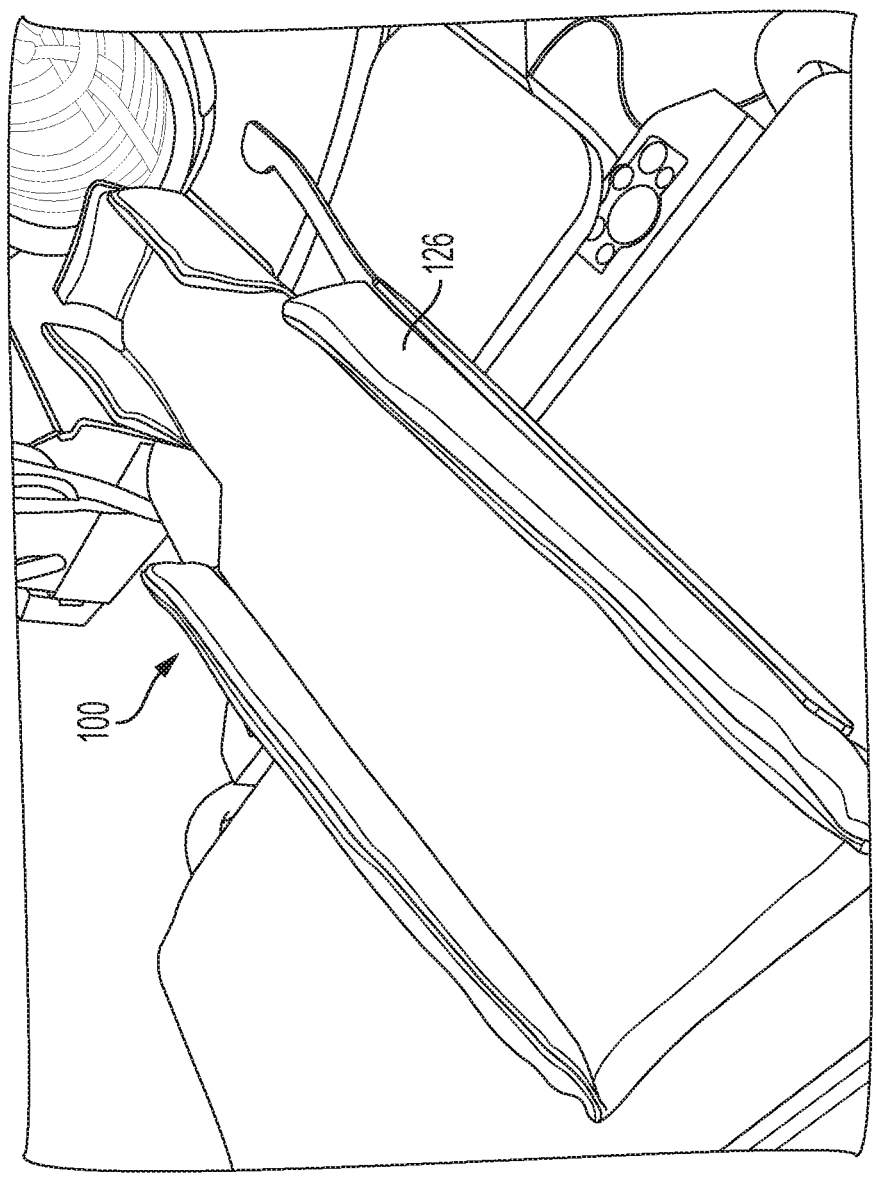
FIG. 25 is a perspective view of the example infant support of FIG. 24, in accordance with some embodiments of the technology described herein.

FIGS. 23-25 illustrate additional views of an infant support. For example, FIG. 23 is a partial top view of the example infant support of FIG. 22, in accordance with some embodiments of the technology described herein. FIG. 24 is a partial front view of an example infant support coupled to an example RF coil assembly, the example infant support having padding, in accordance with some embodiments of the technology described herein. FIG. 25 is a perspective view of the example infant support of FIG. 24, in accordance with some embodiments of the technology described herein.

As shown in FIGS. 24-25, the infant support 100 further comprises padding 126 at least partially covering the tray 104. Padding 126 may increase the comfort of an infant positioned on the tray 104 of the infant support 100 to minimize potential movement of the infant due to discomfort. Padding 126 may comprise any suitable material, for example, a foam material, a water resistant material, and/or a biocompatible material. In some embodiments, padding 126 may be configured such that all or portions of the padding 126 are removable from the tray 104. For example, in some embodiments, it may be desirable to reduce or increase the thickness of the padding 126 depending on the size of the infant. In some embodiments, it may be desirable to dispose of the padding 126 and replace the padding 126 with a new padding, for example, after one or more uses of the padding 126 for MR imaging.

According to an aspect of the technology described herein, the inventors have developed a coupling mechanism 300 and infant support 100 which enables precise positioning of the infant relative to a RF coil assembly and/or an MRI device. The coupling mechanism 300 and infant support 100 may further enable adaptation of an MRI device which may otherwise not be suited for infant imaging, for use with infants. In particular, the inventors have recognized that due to the size and cost of maintaining and operating MRI systems, a facility may not have specialized MRI devices designed for imaging infants. Instead, the facility may only have MRI devices suitable for use with adult patients and/or older children, but given the smaller size of infants, would not be suited for imaging infants, for example due to difficulties in positioning an infant in the adult MRI device, as described herein.

To overcome the issues described herein with respect to conventional MR facilities, the inventors have developed a coupling mechanism, for example, coupling mechanism 300, such that an adult MRI device, such as an MRI device comprising RF coil assembly 200, can be adapted for use with an infant. Further aspects of the coupling mechanism 300 are thus described herein. For example, FIG. 26 is a perspective view of an example coupling mechanism for coupling an infant support to an RF coil assembly, and for coupling an RF coil assembly to a base, in accordance with some embodiments of the technology described herein.

Figure 26:
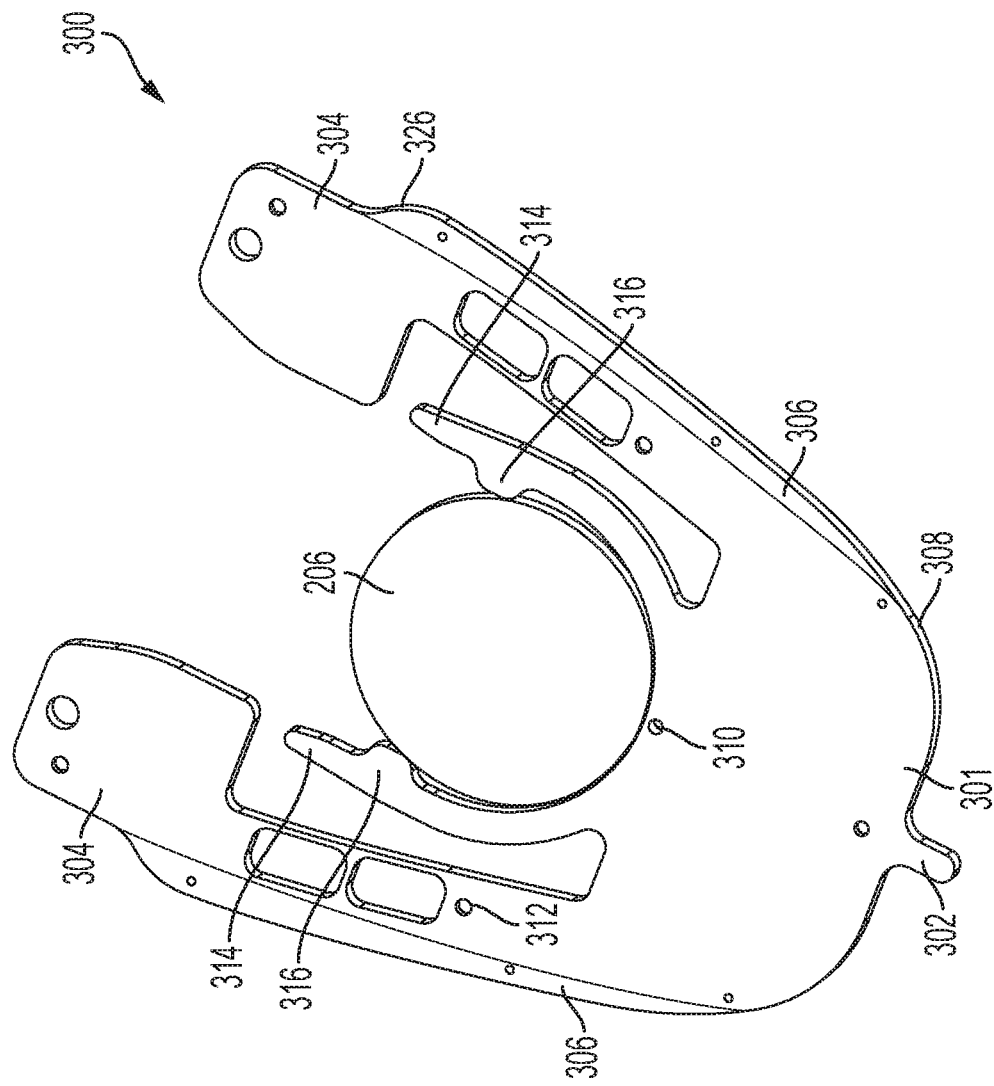
FIG. 26 is a perspective view of an example coupling mechanism for coupling an infant support to an RF coil assembly, and for coupling an RF coil assembly to a base, in accordance with some embodiments of the technology described herein.

As shown in FIG. 26, coupling mechanism 300 comprises a body 301, and outer arms 304 and inner arms 314 coupled to body 301. In the illustrated embodiment, the coupling mechanism 300 includes features that facilitate coupling of an infant support (e.g., infant support 100) to the coupling mechanism 300, features that facilitate coupling of an RF coil assembly (e.g., RF coil assembly 200) to the coupling mechanism, and features that facilitate coupling of an MRI device base (e.g., MRI device base 204) to the coupling mechanism 300. For example, inner arms 314 are coupled to body 301 and are shaped to couple the coupling mechanism 300 to an MRI device base. In particular, inner arms 314 comprise inner arm contacts 316 which extend from inner arms 314 and which may be received in a groove of a helmet base 206 of the MRI device. In addition, one or more holes 310, 312 are provided in the coupling mechanism 300 for receiving one or more fasteners (i.e., a screw, wedge, etc.). The one or more holes 310, 312 and fasteners may facilitate coupling of a helmet support (e.g., helmet support 208) and/or an MRI device base (e.g., MRI device base 204) to the coupling mechanism 300.

As described herein, coupling mechanism 300 may facilitate positioning an infant support relative to an MRI device, e.g., an MRI device comprising a RF coil assembly. For example, outer arms 304 may receive arms 110 of the infant support 100. In particular, outer arms 304 comprise guides 306 on sides of body 301 (e.g., being coupled to outer arms 304). Arms 110 of base 102 may slide along guides 306 when positioning infant support 100 relative the RF coil assembly 200. Curved edges 308 at proximal ends of the guides 306 may facilitate insertion of arms 110 along guides 306. For example, snaps 108 may contact and slide along guides 306 with little resistance at the proximal end of guides 306 having edges 308, while resistance to the insertion of arms 110 may increase as the arms 110 are further inserted. When arms 110 reach distal ends 326 of guides 306 opposite edges 308, snaps 108 abut distal ends 326 such that removal of snaps 108 from the coupling mechanism 300 is opposed. Thus, in some embodiments, the distal ends 326 may receive snaps 108. In some embodiments, the snaps 108 are snap fit into distal ends 326. In some embodiments, the rails 306 may be configured such that arms 110 slide along and above rails 306 when inserted into the coupling mechanism 300.

FIG. 27 is a perspective view of the example coupling mechanism of FIG. 26 having wings for facilitating coupling to an infant support, in accordance with some embodiments of the technology described herein. In particular, as shown in FIG. 27, coupling mechanism 300 comprises a wing 318 on each side of the coupling mechanism, coupled to outer arms 304 and disposed at least partially above guides 306. The wings 318 slope upward substantially along a length of the wings. Thus, in the illustrated embodiment, wings 318 have sloped ends 320 which slope upwards in a direction opposite the direction of insertion of the infant support 100 into the RF coil assembly 200.

Figure 30:
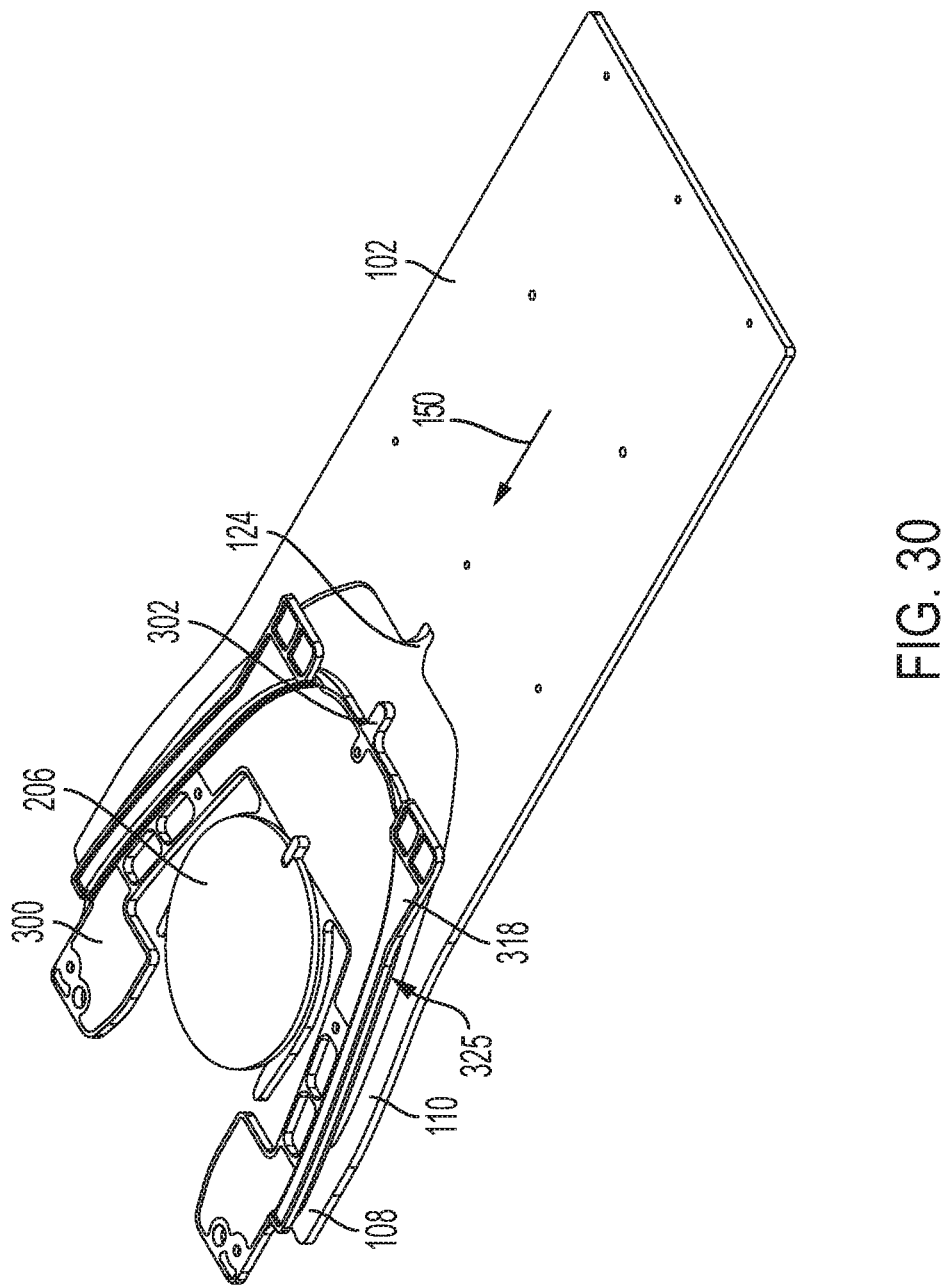
FIG. 30 is a perspective view of an example base of an infant support being coupled to an example coupling mechanism, in accordance with some embodiments of the technology described herein.
Figure 31:
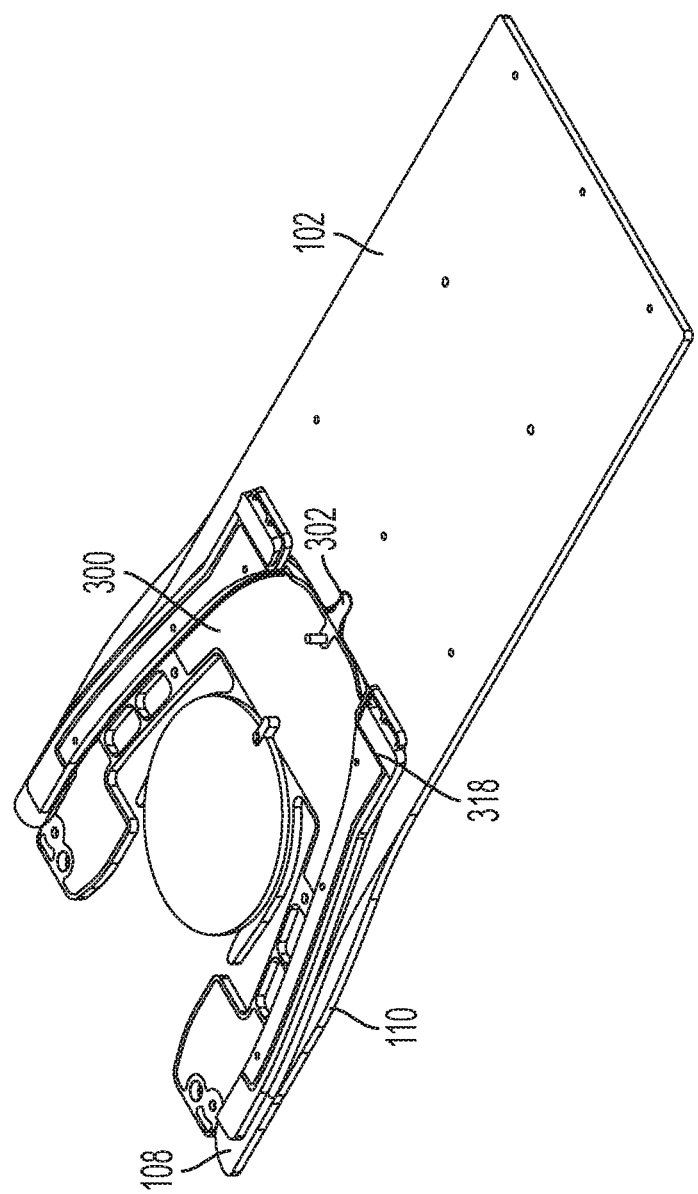
FIG. 31 is a perspective view of the example base of FIG. 30 shown coupled to the example coupling mechanism of FIG. 30, in accordance with some embodiments of the technology described herein.
Figure 32:
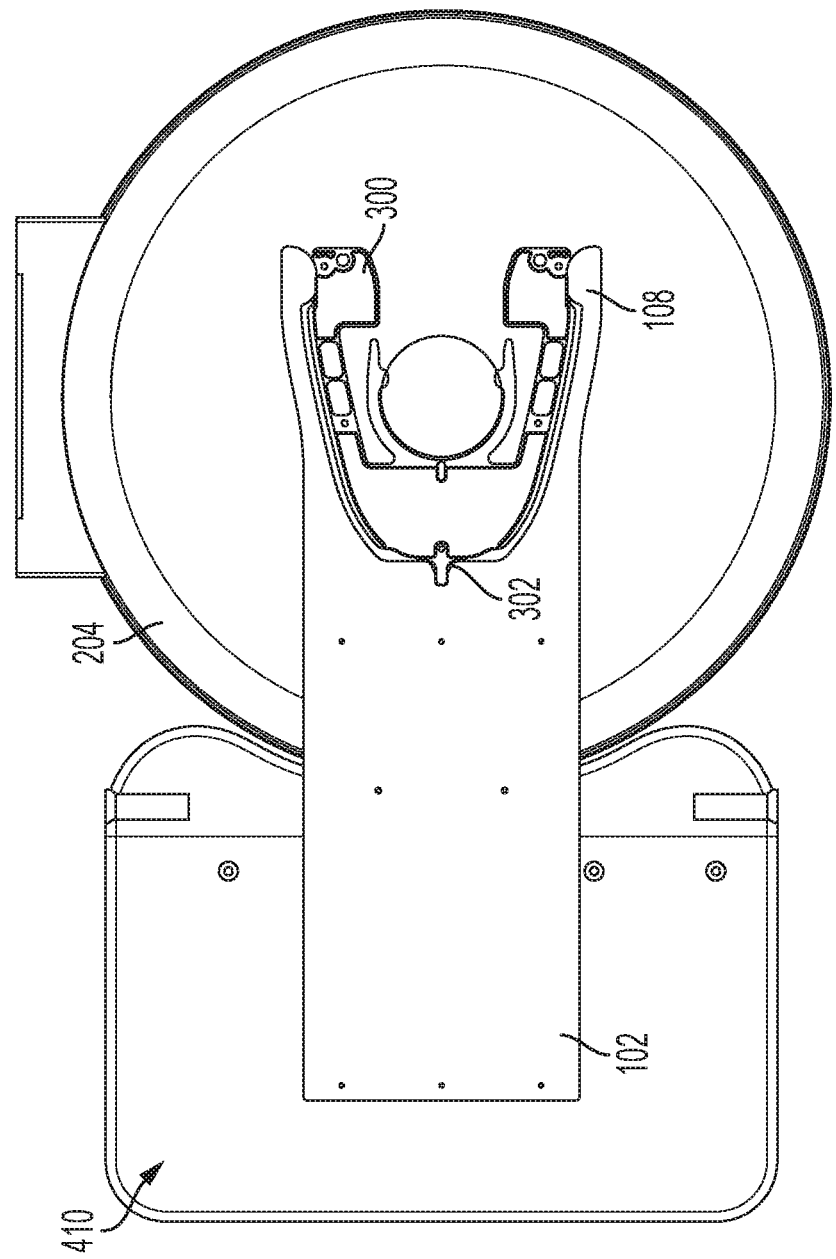
FIG. 32 is a perspective view of an example infant support coupled to an MRI device base by an example coupling mechanism, in accordance with some embodiments of the technology described herein.

The wings 318 and guides 306 together form first and second receiving portions 325 (as shown in FIG. 30, for example) for receiving arms 110 of the infant support 100. The first and second receiving portions 325 may be configured such that the arms 110 of base 102 are received under wings 318 and along (e.g., adjacent to, above, in some embodiments) guides 306. When infant support 100 is fully inserted into the coupling mechanism 300, snaps 108 are positioned under wings 318 and abut distal ends 326 of guides 306, as shown in FIGS. 31-32, for example. As described herein, arms 110 slope upwards in the direction extending outward from the base 102. Wings 318 may press down on snaps 108 as the base 102 is moved towards coupling mechanism 300 to further secure the base 102 to the coupling mechanism 300.

In the illustrated embodiment, coupling mechanism 300 further comprises an alignment feature 302 for facilitating alignment of the infant support 100 relative to the RF coil assembly 200. For example, alignment feature 302 of the coupling mechanism 300 comprises a protrusion to be received by notch 124 of the base 102 when the infant support 100 is inserted into the RF coil assembly 200 to ensure insertion of the infant support is properly performed (e.g., to ensure that the lateral and longitudinal position of the infant support 100 relative to the coupling mechanism 300 and RF coil assembly 200 is correct). In other embodiments, the coupling mechanism 300 may comprise a notch arranged to be received by a protrusion of the infant support 100.

Figure 28A:
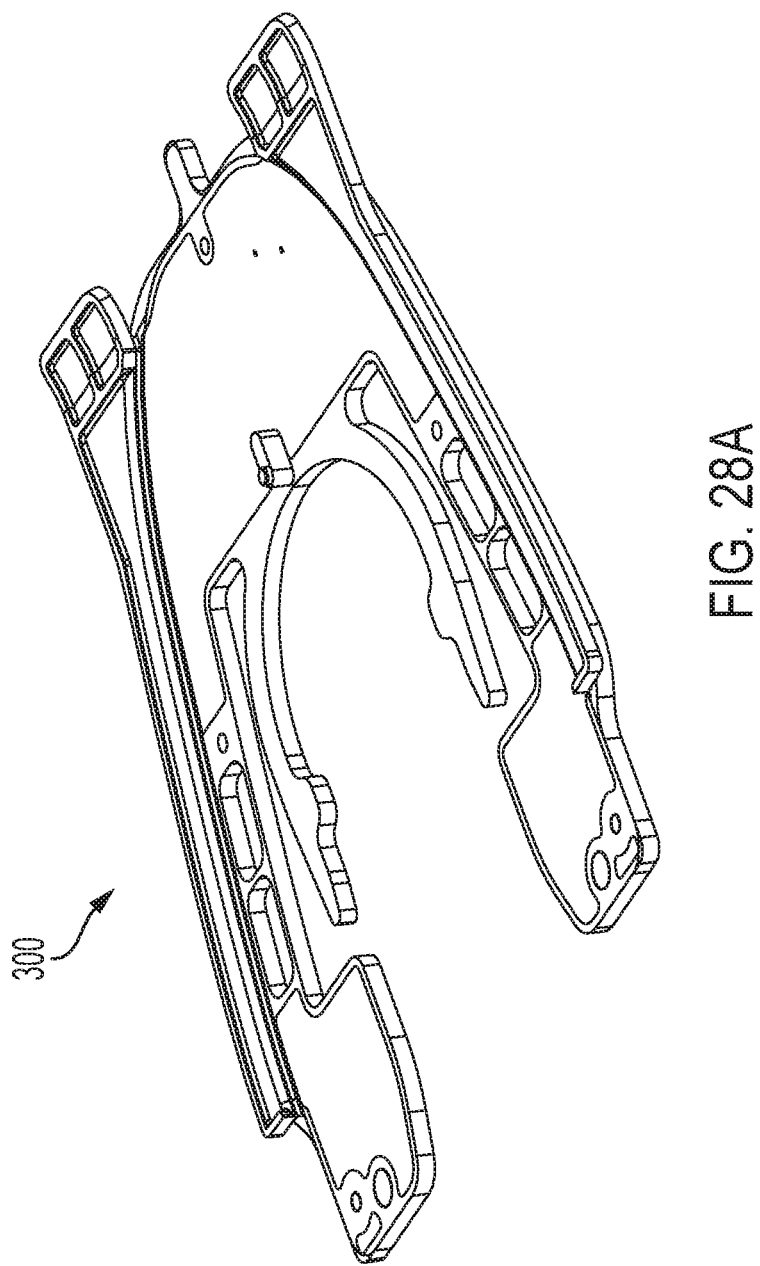
FIG. 28A is a perspective view of an example coupling mechanism configured for coupling an infant support to an RF coil assembly, and for coupling an RF coil assembly to a base, in accordance with some embodiments of the technology described herein.
Figure 28B:
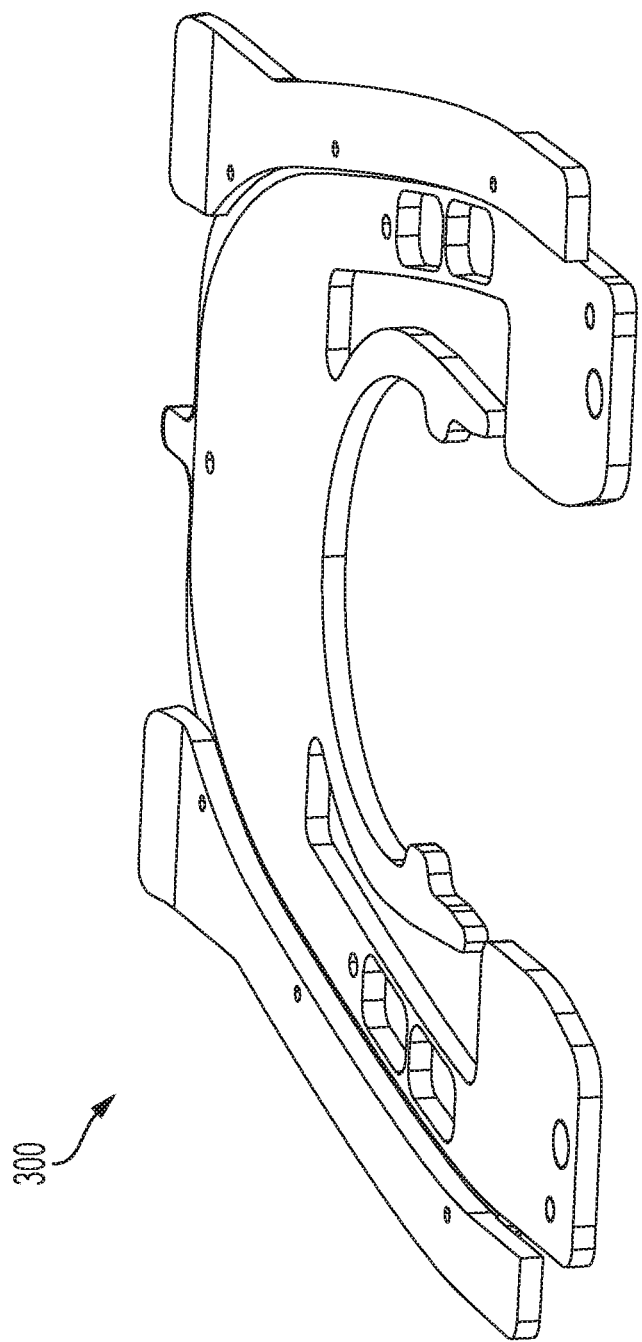
FIG. 28B is a perspective view of another example coupling mechanism configured for coupling an infant support to an RF coil assembly, and for coupling an RF coil assembly to a base, in accordance with some embodiments of the technology described herein.
Figure 28C:
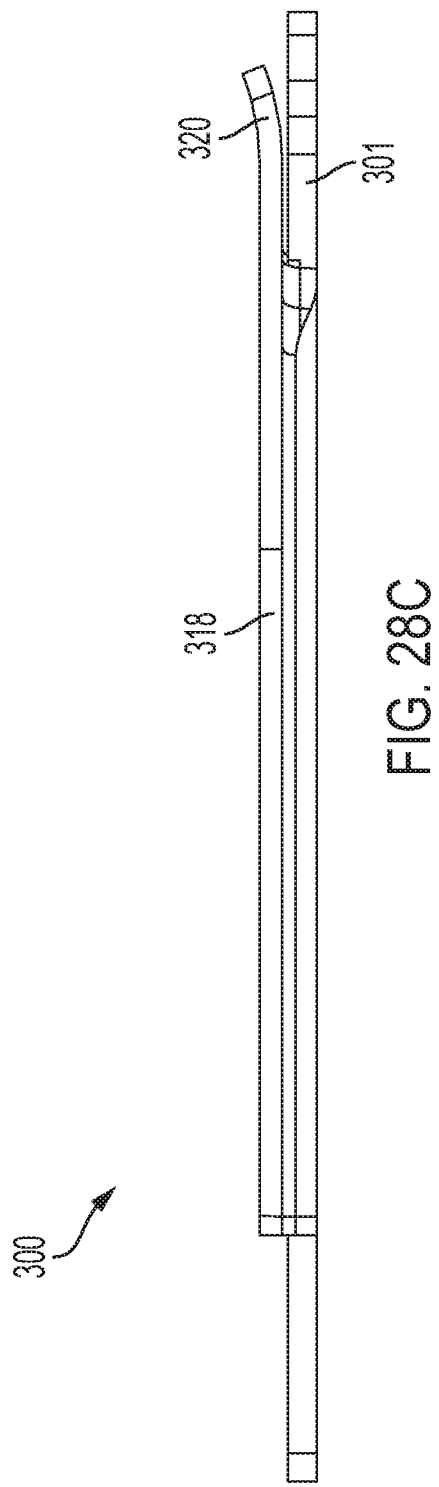
FIG. 28C is a side view of the example coupling mechanism of FIG. 28A, in accordance with some embodiments of the technology described herein.

FIGS. 28A-28C illustrate additional views of the example coupling mechanism 300. For example, FIG. 28A is a perspective view of an example coupling mechanism configured for coupling an infant support to an RF coil assembly, and for coupling an RF coil assembly to a base, in accordance with some embodiments of the technology described herein. FIG. 28B is a perspective view of another example coupling mechanism configured for coupling an infant support to an RF coil assembly, and for coupling an RF coil assembly to a base, in accordance with some embodiments of the technology described herein. Coupling mechanism 300 may be formed in any suitable way using any suitable material, for example, a plastic (e.g., Nylon 12, HDPE, etc.). FIG. 28A illustrates an example of a coupling mechanism 300 manufactured by injection molding. FIG. 28B illustrates an example of a coupling mechanism manufactured by pressure forming.

FIG. 28C is a side view of the example coupling mechanism of FIG. 28A, in accordance with some embodiments of the technology described herein. As shown in FIG. 28C, wings 318 of the coupling mechanism 300 have sloped ends 320 to facilitate coupling the base 102 of infant support 100 to the coupling mechanism 300, as described herein.

Figure 29:
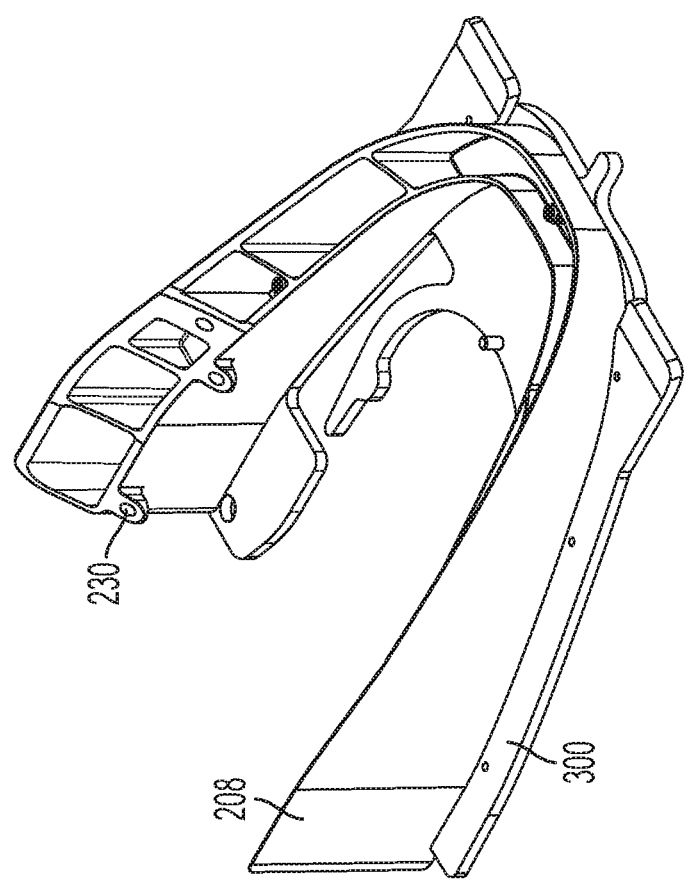
FIG. 29 is a perspective view of the example coupling mechanism of FIG. 27 being coupled to a helmet support of an example RF coil assembly, in accordance with some embodiments of the technology described herein.

FIG. 29 is a perspective view of the example coupling mechanism of FIG. 27 being coupled to a helmet support of an example RF coil assembly, in accordance with some embodiments of the technology described herein. Helmet support 208 may be provided for supporting helmet 202 of RF coil assembly 200, for example, by maintaining helmet 202 at a particular position and orientation. As described herein, helmet support 208 may be coupled to the coupling mechanism 300 via any suitable mechanism, for example, in some embodiments, using one or more fasteners received in holes 312. FIG. 29 further illustrates holes 230 of the helmet support which may receive a fastener to couple helmet 202 to helmet support 208.

FIGS. 30-32 illustrate additional views of an infant support being coupled to a coupling mechanism. For example, FIG. 30 is a perspective view of an example base of an infant support being coupled to an example coupling mechanism, in accordance with some embodiments of the technology described herein. FIG. 31 is a perspective view of the example base of FIG. 30 shown coupled to the example coupling mechanism of FIG. 30, in accordance with some embodiments of the technology described herein. FIG. 32 is a perspective view of an example infant support coupled to an MRI device base by an example coupling mechanism, in accordance with some embodiments of the technology described herein.

As shown in FIG. 32, a support bridge 410 may be provided to support the infant support 100 during positioning and imaging. For example, in some embodiments, support bridge 410 may be coupled to a MRI device. In some embodiments, the support bridge 410 may comprise a fold-out bridge that can be moved from a vertical position for stowing during transport of a portable low-field MRI system or when the MRI system is not in use to a horizontal position to facilitate positioning of a patient for point-of-care MRI. Further aspects of the support bridge 410 are described in U.S. patent application Ser. No. 16/516,760 titled "PATIENT SUPPORT BRIDGE METHODS AND APPARATUS," filed Jul. 19, 2019 which is hereby incorporated by reference in its entirety herein.

Figure 33:
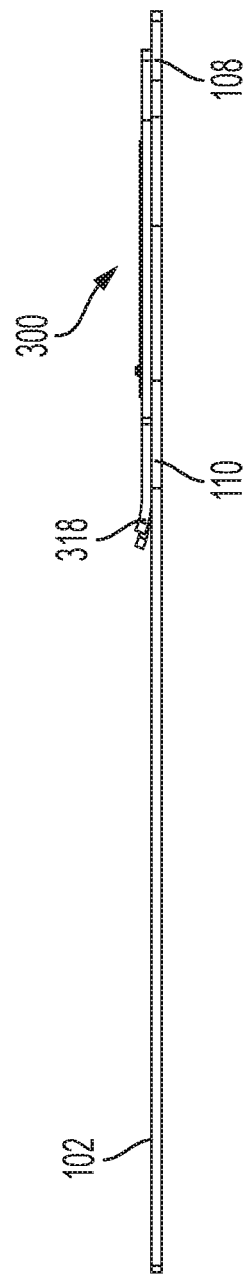
FIG. 33 is a side view of the example base of the infant support of FIG. 30 shown coupled to the example coupling mechanism of FIG. 30, in accordance with some embodiments of the technology described herein.

FIG. 33 is a side view of the example base of the infant support of FIG. 30 shown coupled to the example coupling mechanism of FIG. 30, in accordance with some embodiments of the technology described herein.

Figure 34:
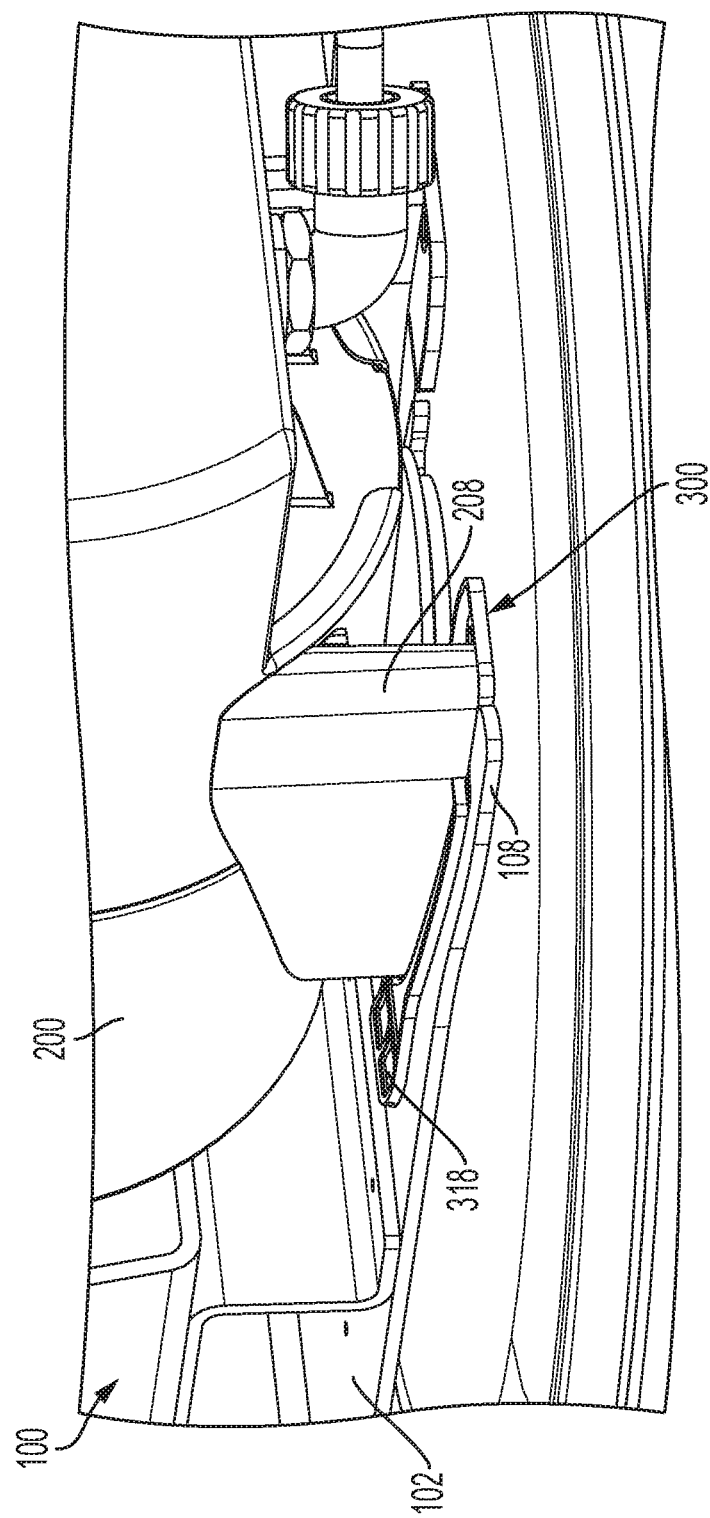
FIG. 34 is a partial rear view of an example infant support being coupled to an example RF coil assembly via a coupling mechanism, in accordance with some embodiments of the technology described herein.

FIG. 34 is a partial rear view of an example infant support being coupled to an example RF coil assembly via a coupling mechanism, in accordance with some embodiments of the technology described herein.

Figure 35:
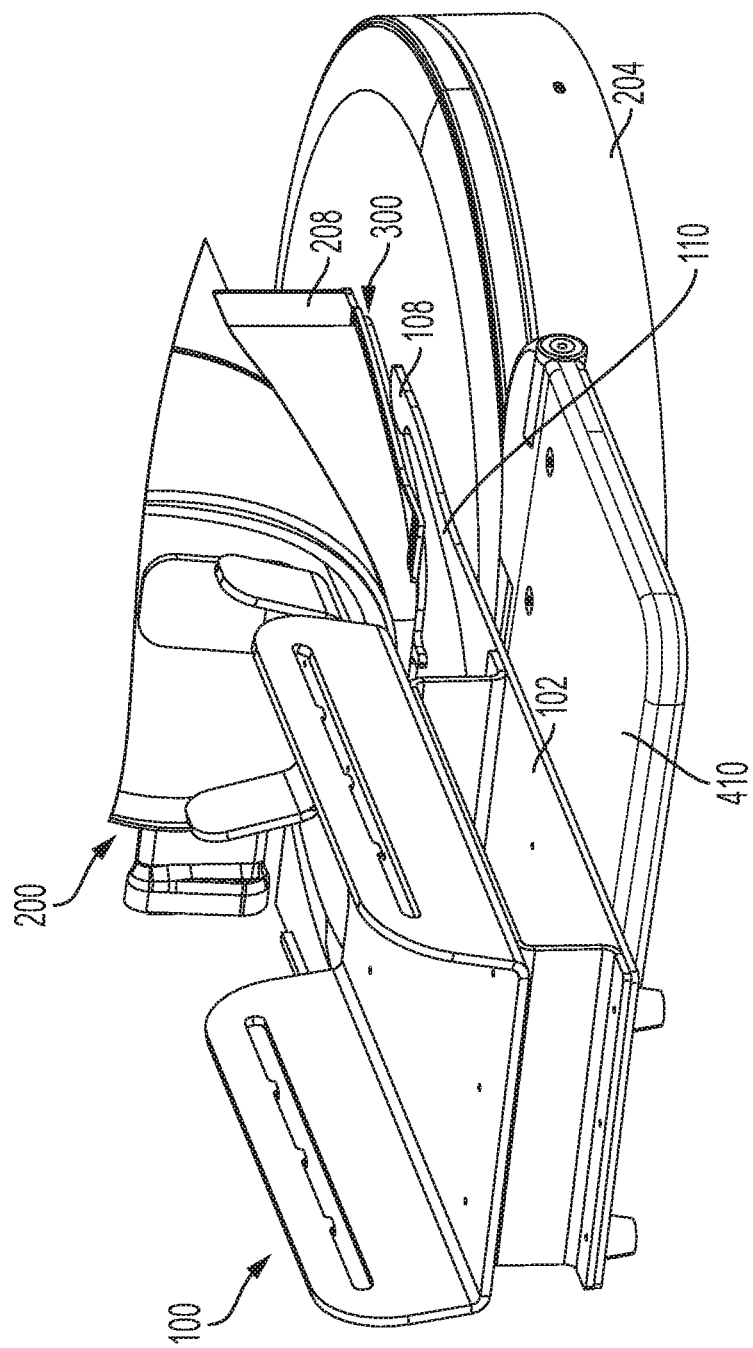
FIG. 35 is a partial perspective view of an example infant support being coupled to an example RF coil assembly via a coupling mechanism, in accordance with some embodiments of the technology described herein.

FIG. 35 is a partial perspective view of an example infant support being coupled to an example RF coil assembly via a coupling mechanism, in accordance with some embodiments of the technology described herein. FIG. 35 illustrates an example of the support bridge 410 being coupled to the MRI device base 204 and positioned under infant support 100 during insertion of the infant support 100 into the RF coil assembly 200.

Figure 36:
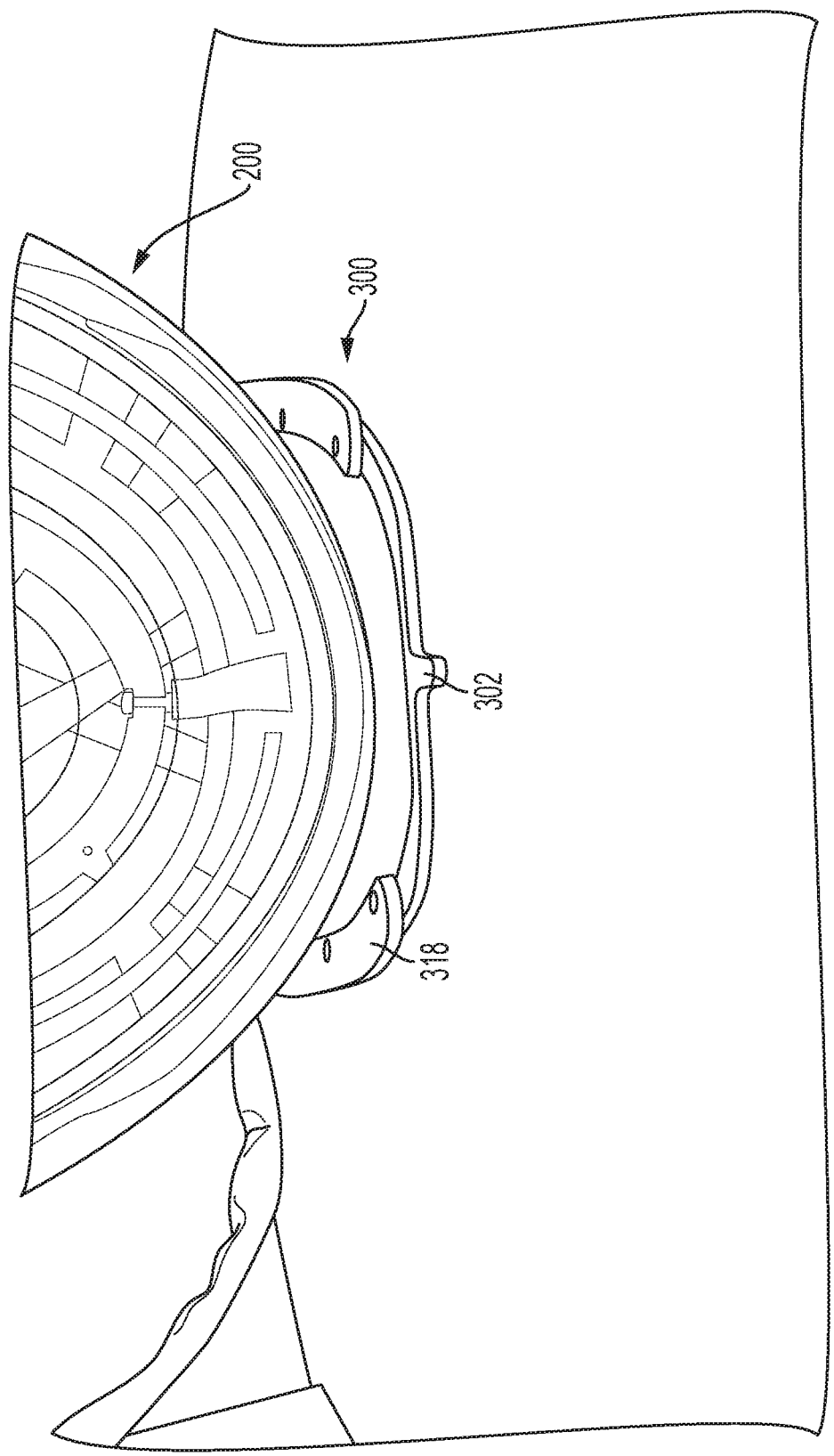
FIG. 36 is a partial perspective view of an example coupling mechanism and RF coil assembly, in accordance with some embodiments of the technology described herein.

FIG. 36 is a partial perspective view of an example coupling mechanism and RF coil assembly, in accordance with some embodiments of the technology described herein.

Figure 37:
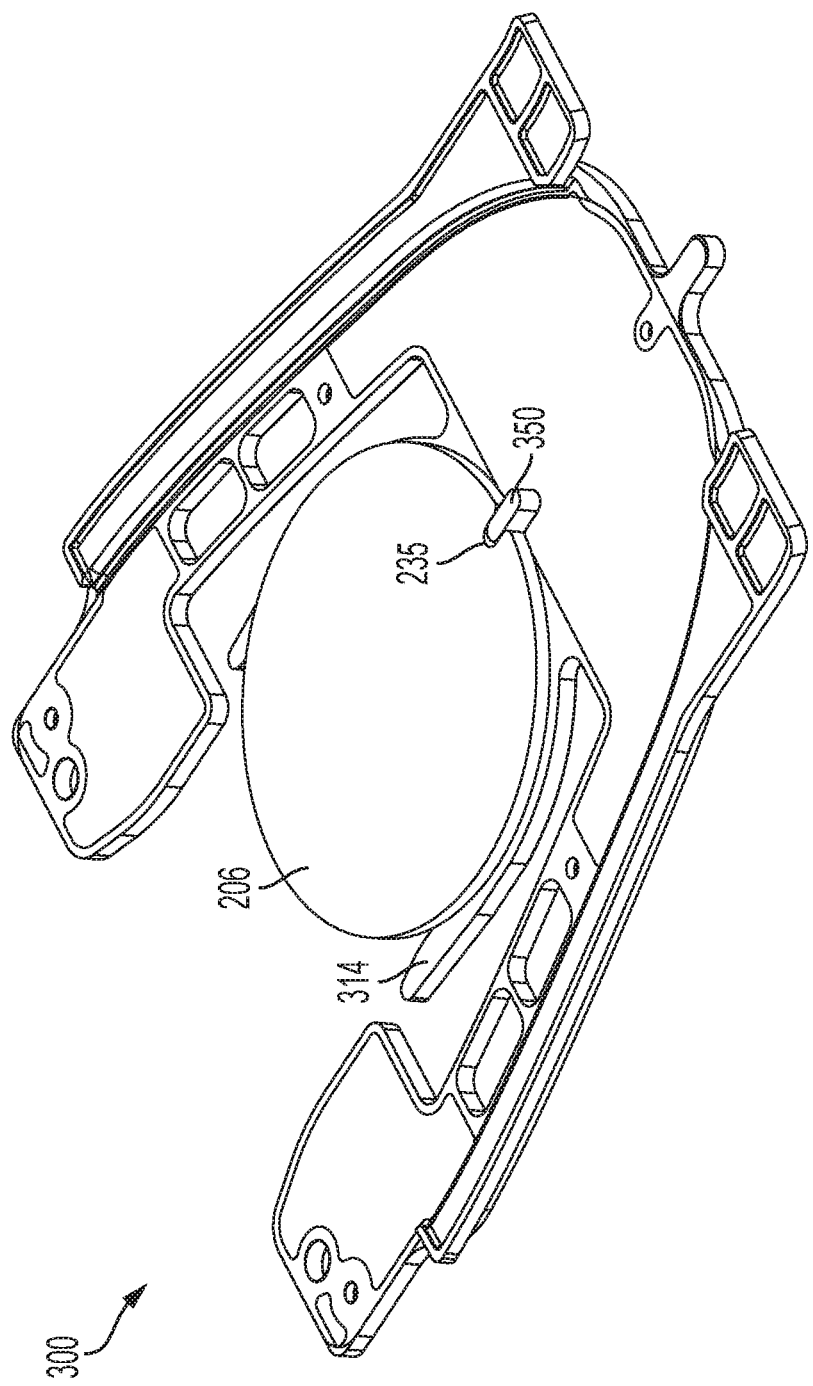
FIG. 37 is a perspective view of an example coupling mechanism, in accordance with some embodiments of the technology described herein.

FIG. 37 is a perspective view of an example coupling mechanism, in accordance with some embodiments of the technology described herein. For example, in FIG. 37, a fastener 350 is shown received in an indent 235 of helmet base 206 which may facilitate positioning of the helmet base 206 relative to the coupling mechanism 300 and MRI device base 204. In particular, fastener 350 ensures that helmet base 206 does not inadvertently rotate, which may cause helmet 202 to rotate, during image acquisition.

Figure 38A:
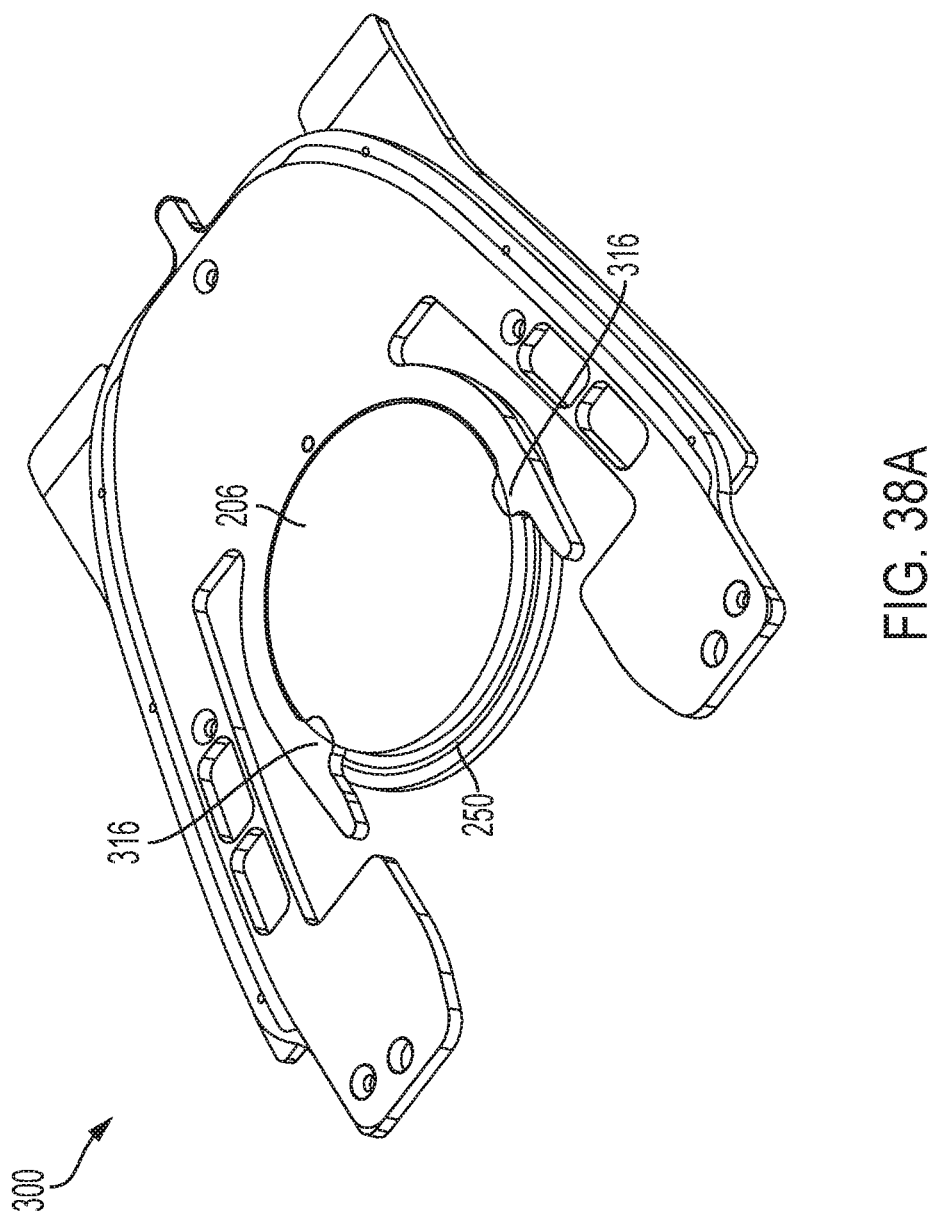
FIGS. 38A-38B are bottom views of the example coupling mechanism of FIG. 37 being coupled to an example base of an RF coil assembly, in accordance with some embodiments of the technology described herein.
Figure 38B:
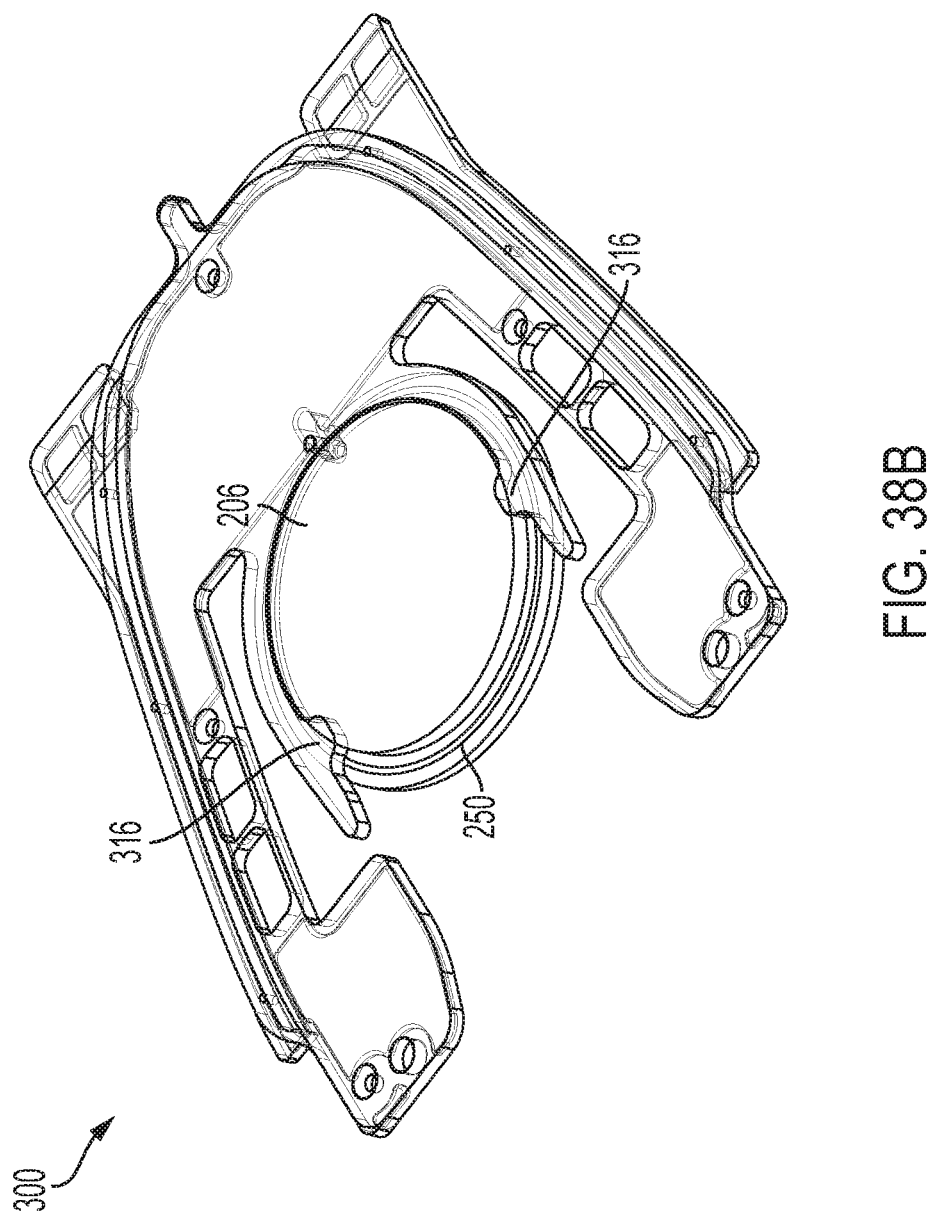

FIGS. 38A-38B are bottom views of the example coupling mechanism of FIG. 37 being coupled to an example base of an RF coil assembly, in accordance with some embodiments of the technology described herein. As shown in FIGS. 38A-38B, helmet base 206 comprises a groove 250, and inner arm contacts 316 are received by groove 250 to secure helmet base 206 to coupling mechanism 300.

Figure 39:
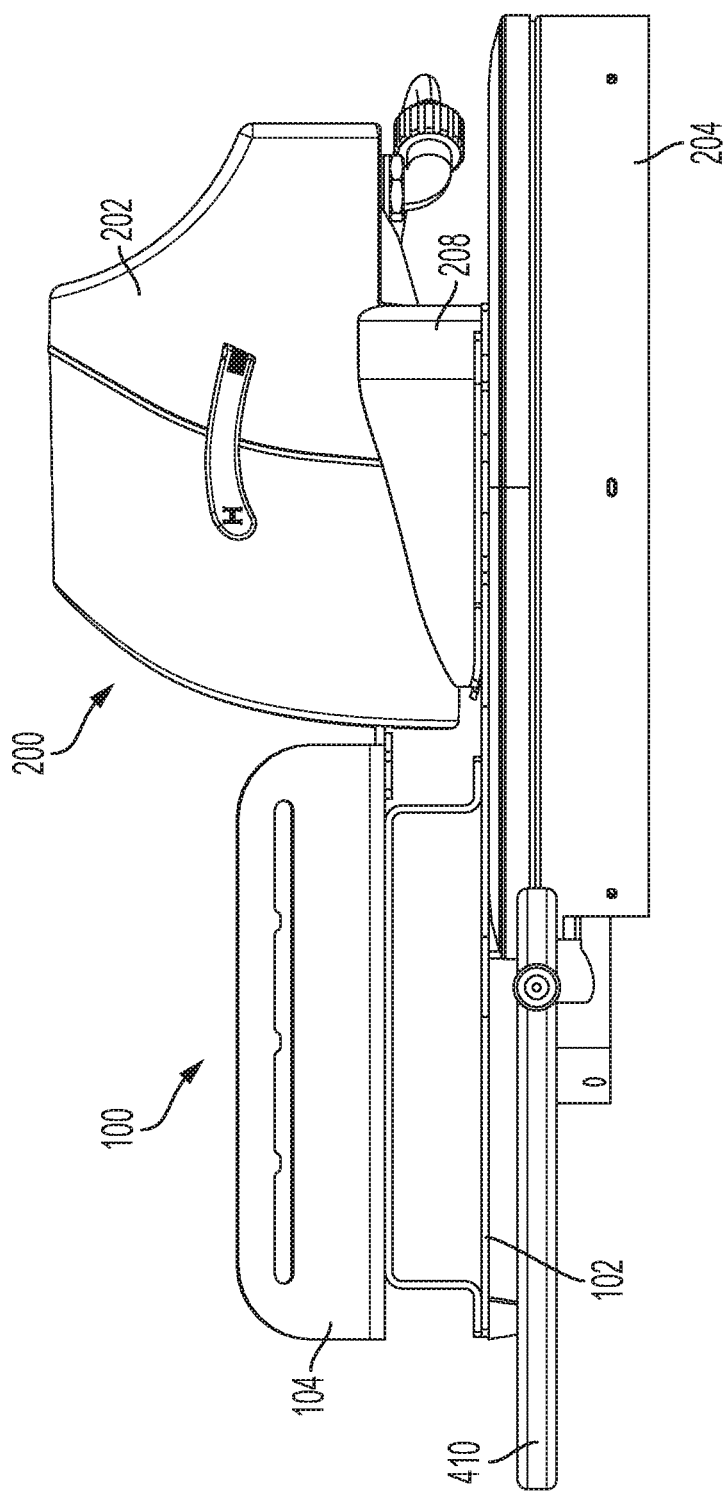
FIG. 39 is a side view of an example infant support being coupled to an example RF coil assembly, in accordance with some embodiments of the technology described herein.
Figure 40:
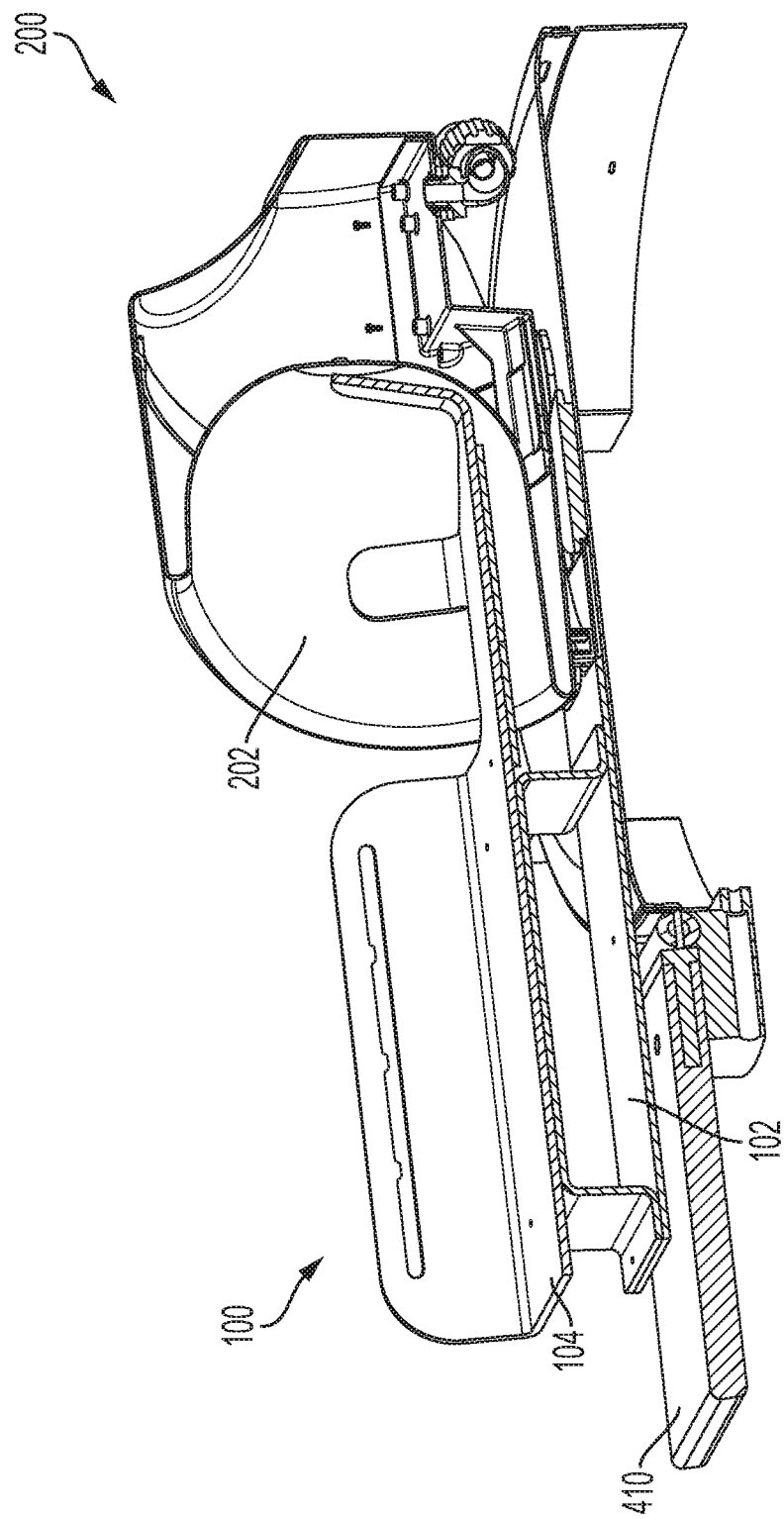
FIG. 40 is a cutaway view of an example infant support being coupled to an example RF coil assembly, in accordance with some embodiments of the technology described herein.

FIGS. 39-40 illustrate additional views of an infant support being coupled to an RF coil assembly. FIG. 39 is a side view of an example infant support being coupled to an example RF coil assembly, in accordance with some embodiments of the technology described herein. FIG. 40 is a cutaway view of an example infant support being coupled to an example RF coil assembly, in accordance with some embodiments of the technology described herein.

Figure 41B:
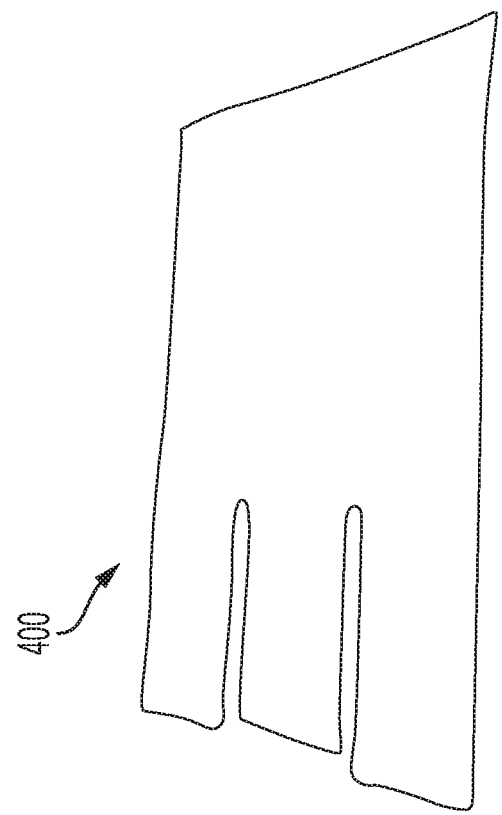
FIGS. 41A-41C are perspective views of example inclined pads for an RF coil assembly, in accordance with some embodiments of the technology described herein.
Figure 41A:
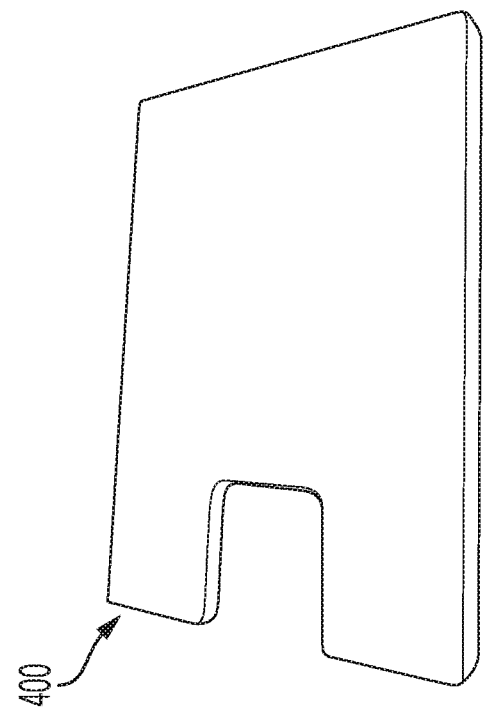
Figure 41C:
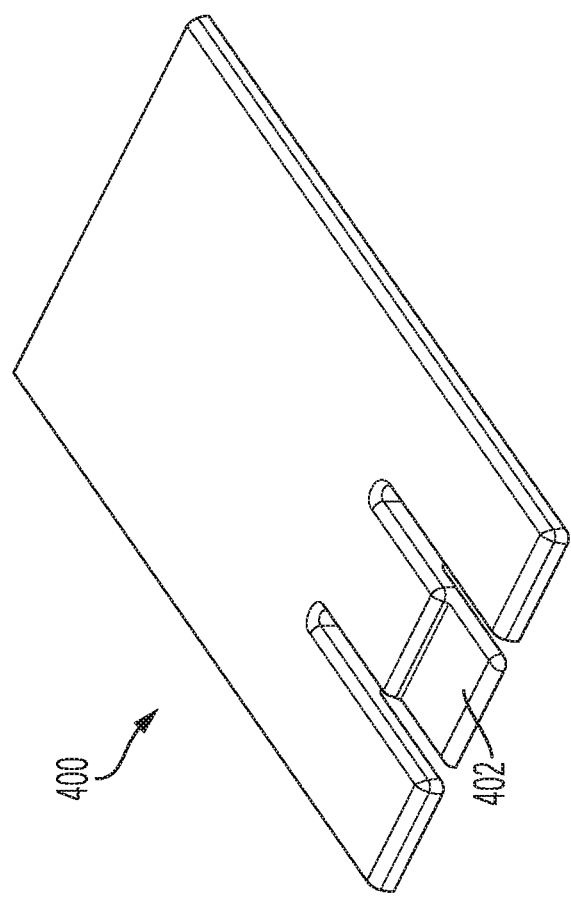

FIGS. 41A-41C are perspective views of example inclined pads for an RF coil assembly, in accordance with some embodiments of the technology described herein. Pad 400 may facilitate movement of the infant support 100 towards the RF coil assembly and/or MRI device. For example, the pad 400 may provide an inclined ramp along which the infant support 100 can be moved along and onto the support bridge 410, as described herein. Pad 400 may have any suitable thickness, for example 1 inch, 1½ inches, etc. In addition, in the illustrated embodiment, pad 400 comprises a ramp-in feature 402 to facilitate insertion of the infant support 100 onto the support bridge 410, as described herein.

Figure 42:
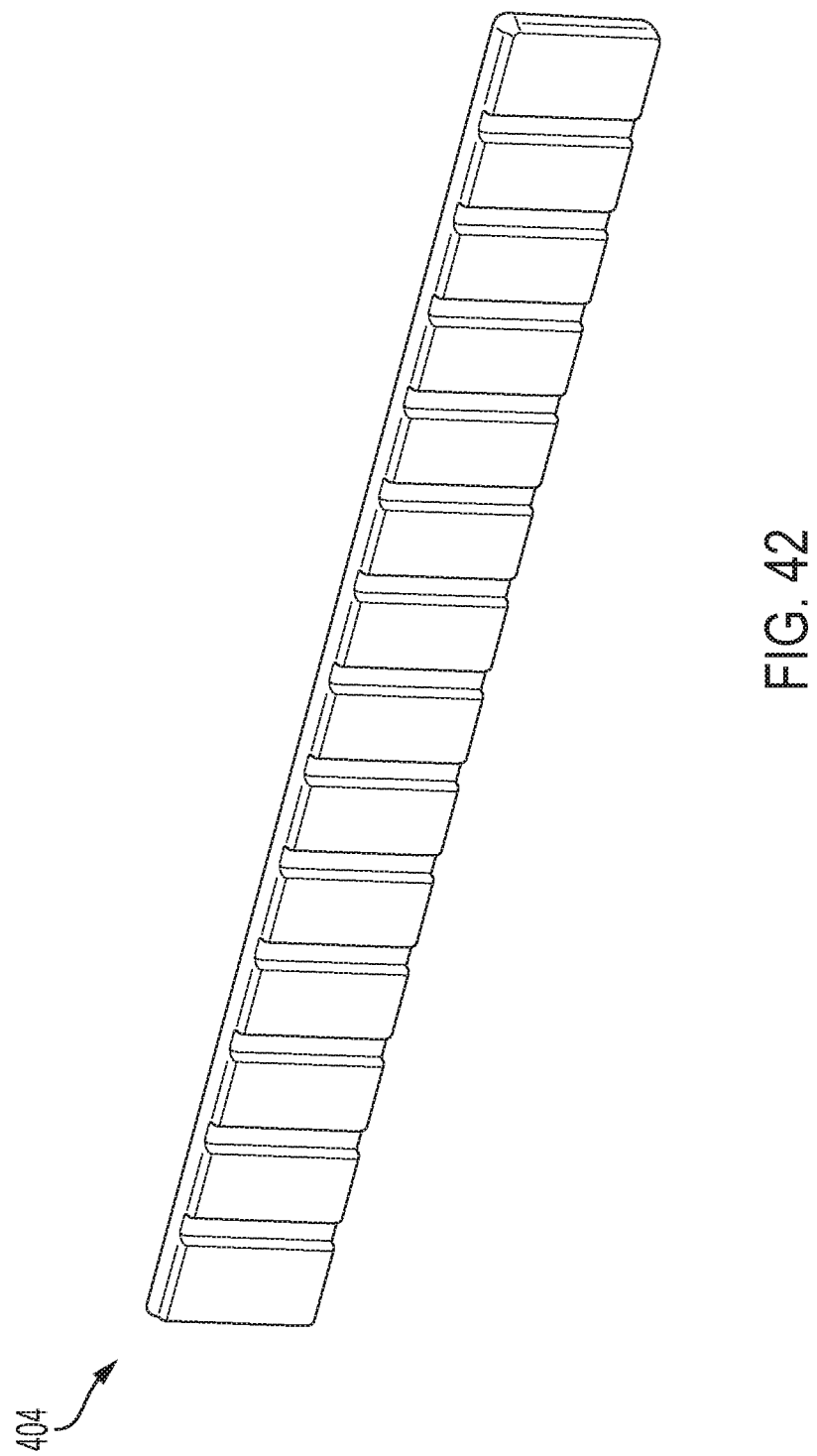
FIG. 42 is a perspective view of an example head restraint for an infant support, in accordance with some embodiments of the technology described herein.
Figure 43:
FIGS. 43-48 are example perspective views of an infant being positioned into an example RF coil assembly via an example infant support, in accordance with some embodiments of the technology described herein.
Figure 44:
Figure 45:
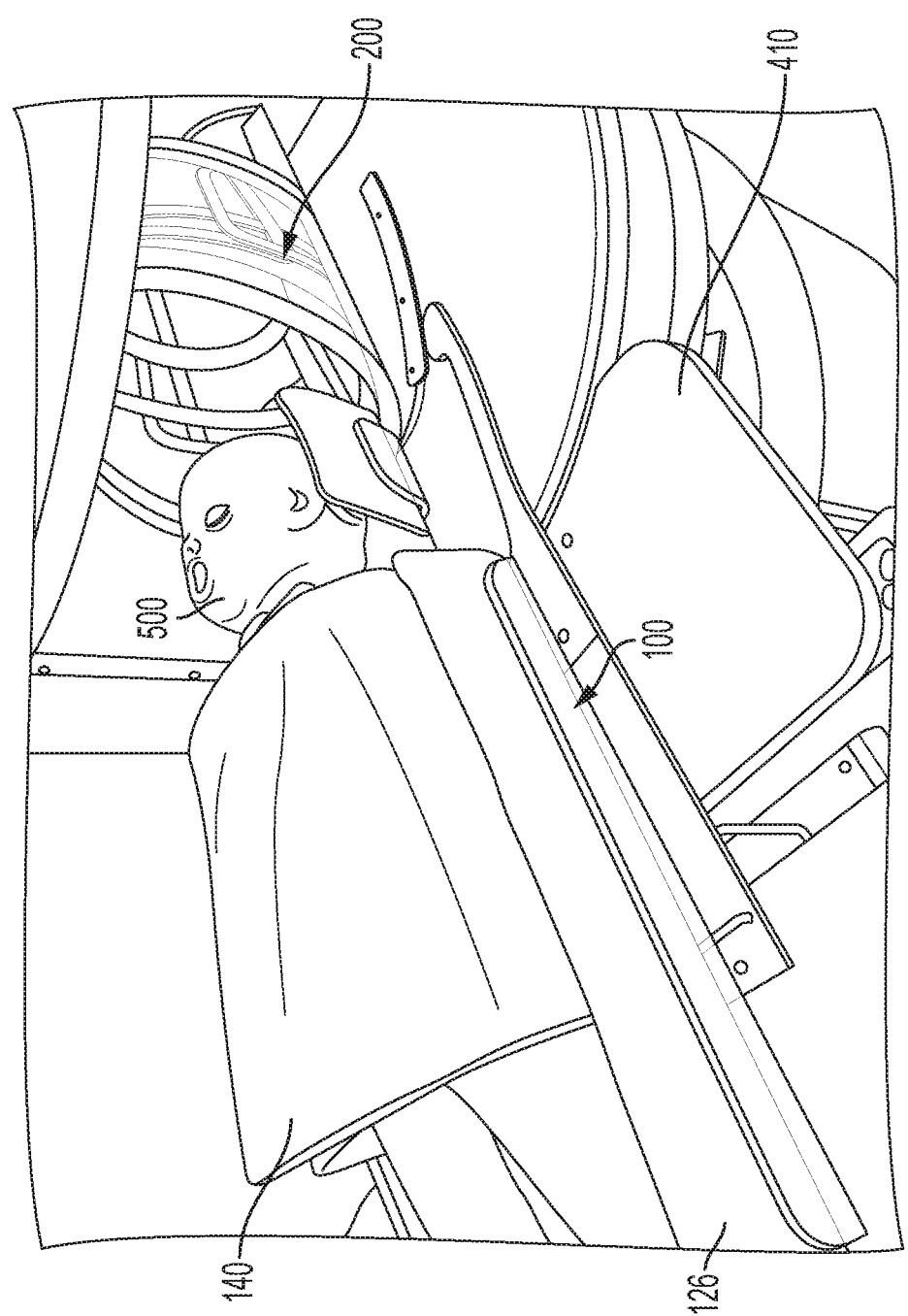
Figure 46:
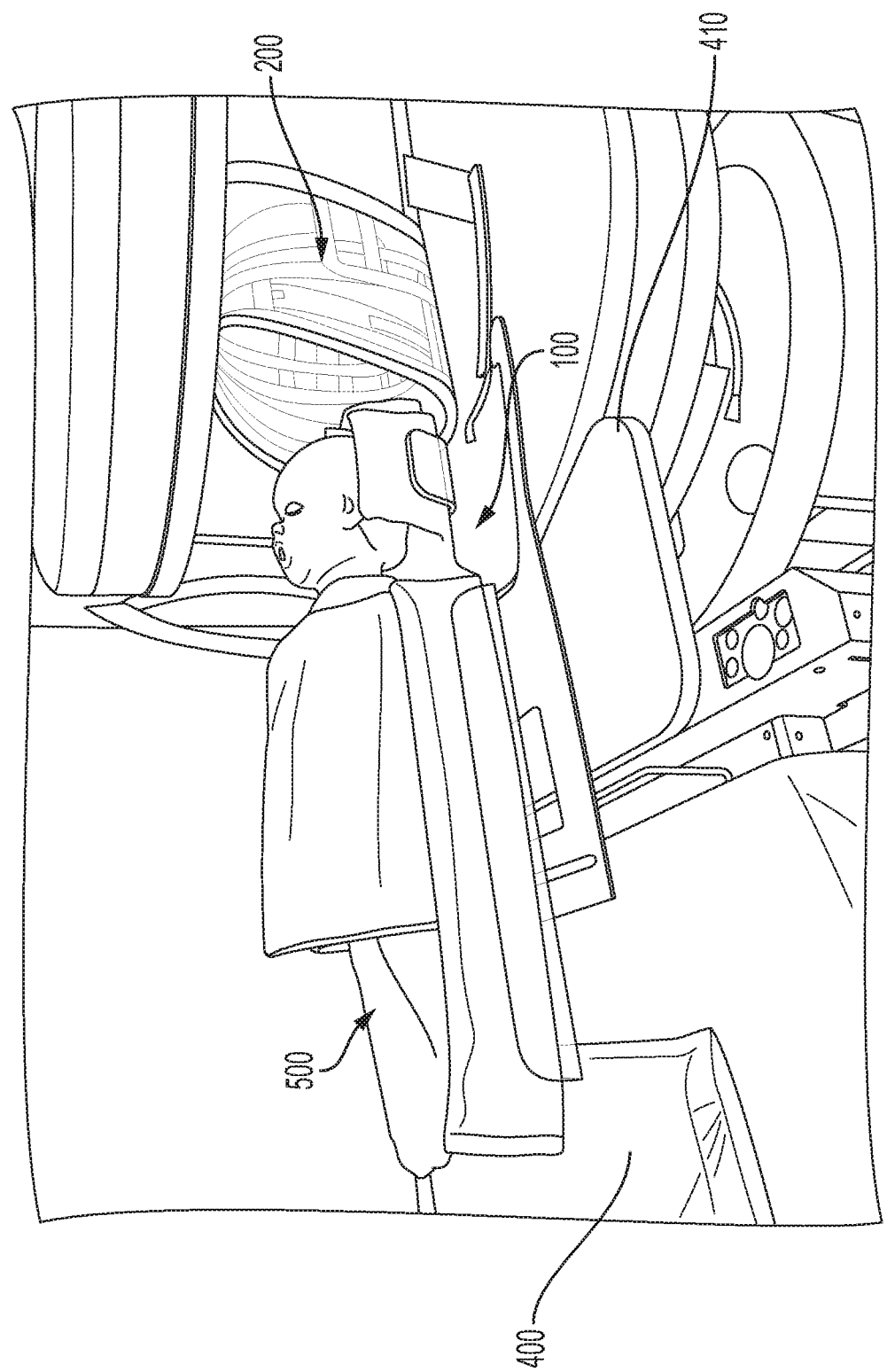
Figure 47:
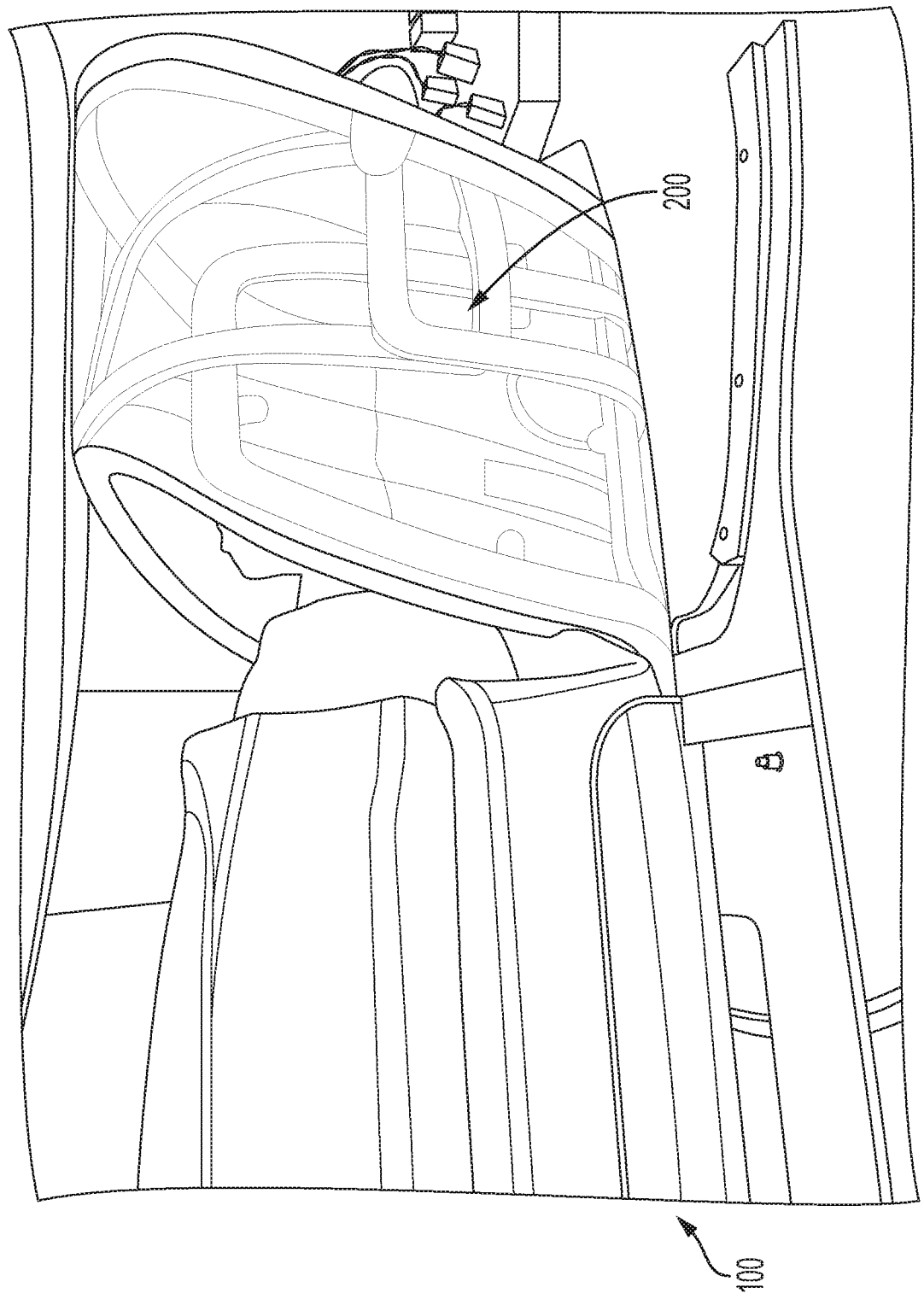
Figure 48:
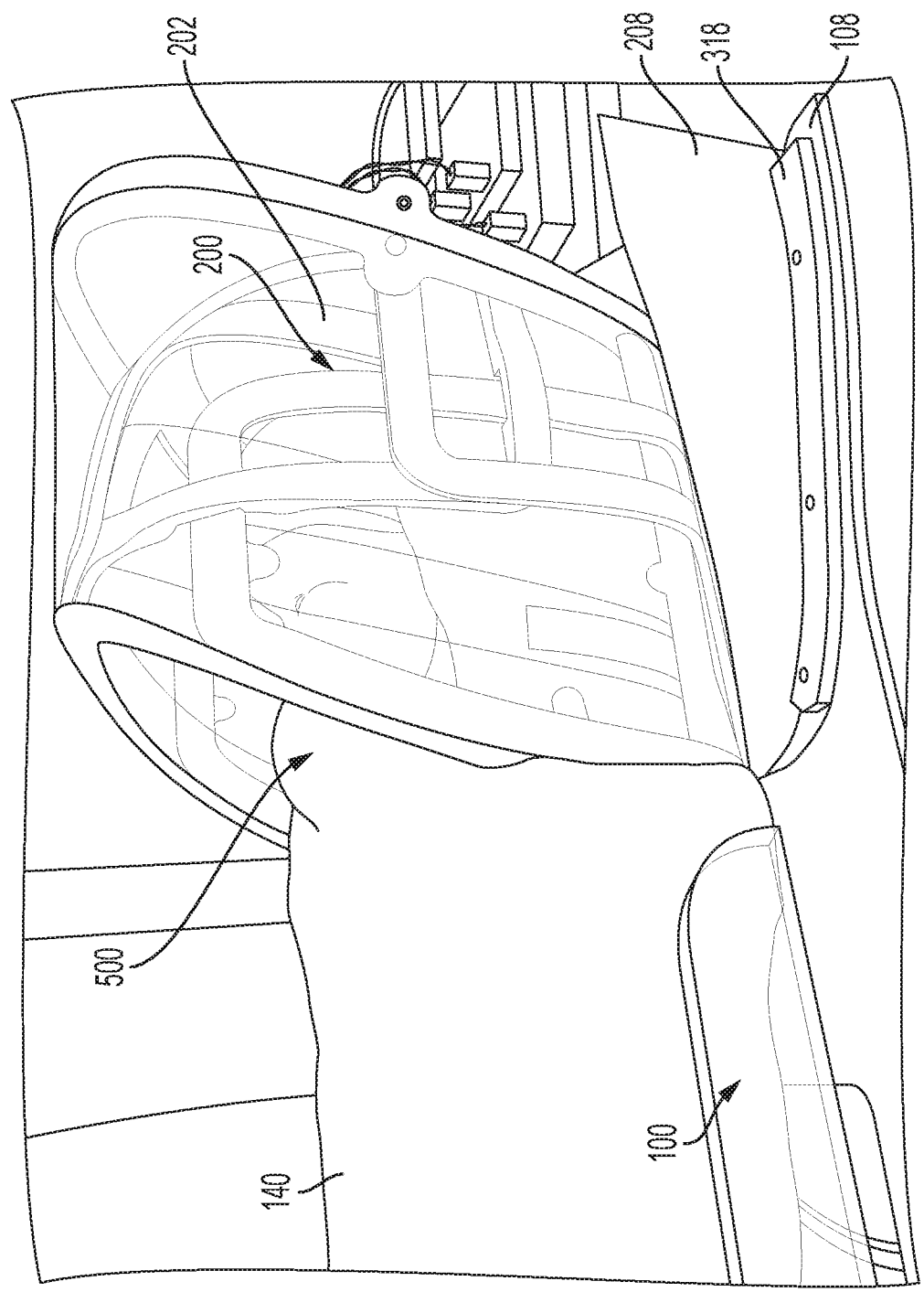

FIG. 42 is a perspective view of an example head restraint for an infant support, in accordance with some embodiments of the technology described herein. As described herein, one or more restraints may be coupled to the infant support 100 to limit movement of an infant positioned in the tray 104. For example, a head bumper 404 may be implemented to limit movement of an infant's head during imaging, as shown, for example, in FIG. 43.

FIGS. 43-48 are example perspective views of an infant being positioned into an example RF coil assembly via an example infant support, in accordance with some embodiments of the technology described herein. As shown in FIGS. 43-48, an infant 500 may be placed on tray 104 of infant support 100 and positioned relative to an RF coil assembly 200. In particular, the infant support 100 is configured such that the infant's head is received within an opening 210 of the helmet 202 so that imaging of the infant's head can be performed. As shown in FIGS. 43-48, a wrap 140 is positioned around the infant 500 to further limit movement of the infant 500 and provide additional comfort for the infant. For example, in some embodiments, the wrap 140 comprises a weighted blanket. Any suitable wrap 140 may be used, and, in some embodiments, the particular type of wrap 140 implemented may depend on a characteristic of the infant 500, for example, the infant's size and/or how restless the infant appears to be. In some embodiments, more than one wrap may be implemented.

Figure 49:
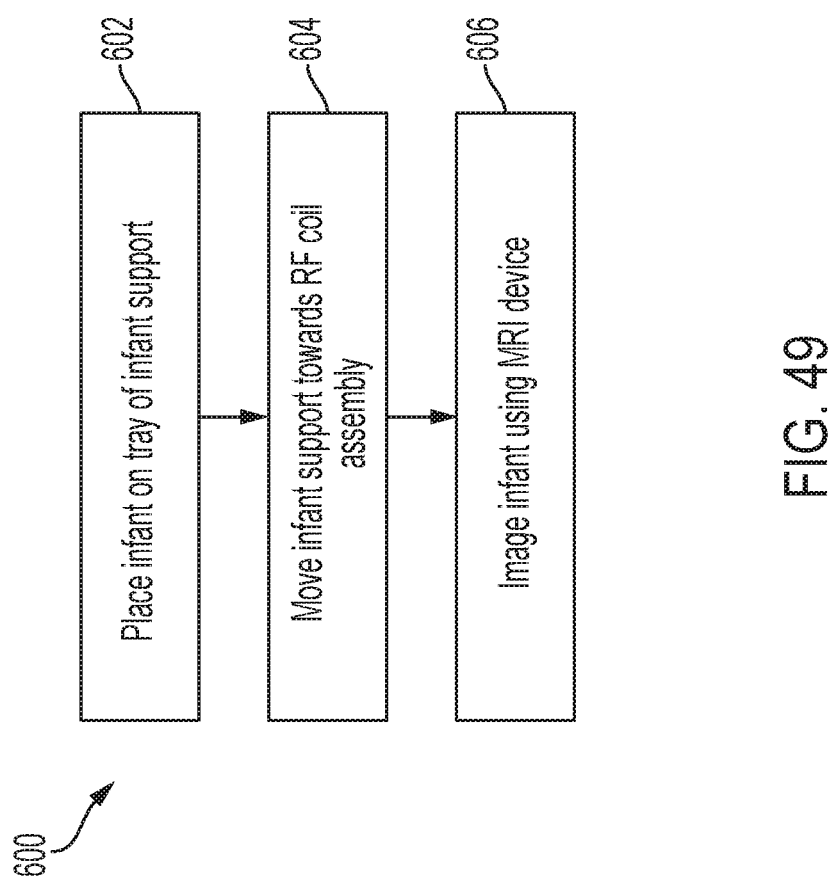
FIG. 49 is an example method for positioning an infant in a field of view of an MRI device, in accordance with some embodiments of the technology described herein.

According to some aspect of the technology described herein, there is provided an example method for positioning an infant relative to an MRI device. For example, FIG. 49 illustrates an example method 600 for positioning an infant in a field of view of an MRI device, in accordance with some embodiments of the technology described herein. The method 600 may be performed by a medical professional, for example.

Method 600 begins at act 602 where the infant is placed on a tray of the infant support along a longitudinal axis of the infant support. For example, the infant may be placed on a surface of the infant support and between sides of the infant support. The infant's head may be positioned such that the infant's head is supported by a distal end of the surface and the infant's body and legs are supported by a proximal end of the surface.

In some embodiments, an appropriate padding (e.g., padding 126) may be placed on the tray before placing the infant on the tray. In some embodiments, the infant may be placed in a wrap (e.g., wrap 140 shown in FIG. 43) before being placed on the tray. In some embodiments, one or more restraints (e.g., straps) may be extended over one or more portions of the infant's body to prevent movement of the infant.

At act 604, the infant support is moved towards the RF coil assembly. For example, the infant support is moved in a direction along the longitudinal axis so that the arms of the infant support are inserted into a coupling mechanism coupled to the RF coil assembly and at least a portion of the infant's head is disposed within an opening of the RF coil assembly.

In some embodiments, the infant support may be moved towards the RF coil assembly at least until either a notch of the infant support receives a protrusion of the coupling mechanism or a protrusion of the infant support is received by a notch of the coupling mechanism. In some embodiments, the infant support may be moved towards the RF coil assembly at least until snaps disposed at distal ends of the arms of the infant support are received by respective distal ends of guides of the coupling mechanism.

At act 606, the infant is imaged using the MRI device. For example, the one or more transmit and/or receive coils of the RF coil assembly may be used alone or in combination with an MRI device to acquire at least one magnetic resonance image of the infant (e.g., at least one magnetic resonance image of at least a portion of the infant's head).

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Although aspects of the technology have been described herein with respect to positioning an infant within an RF coil assembly, it should be appreciated that aspects of the technology may be implemented for positioning a patient relative to any suitable type of MRI device, and aspects of the technology described herein are not limited to RF coil assemblies or MRI devices configured for imaging an infant's head. In addition, aspects of the technology may be implemented in connection with positioning any patient relative to an MRI device, and aspects of the technology described herein are not limited to infant supports alone.

As described herein, the MRI scanner market is overwhelmingly dominated by high-field systems, and particularly for medical or clinical MRI applications. The general trend in medical imaging has been to produce MRI scanners with increasingly greater field strengths, with the vast majority of clinical MRI scanners operating at 1.5 T or 3 T, with higher field strengths of 7 T and 9 T used in research settings. As used herein, "high-field" refers generally to MRI systems presently in use in a clinical setting and, more particularly, to MRI systems operating with a main magnetic field (i.e., a $B_0$ field) at or above 1.5 T, though clinical systems operating between 0.5 T and 1.5 T are often also characterized as "high-field." Field strengths between approximately 0.2 T and 0.5 T have been characterized as "mid-field" and, as field strengths in the high-field regime have continued to increase, field strengths in the range between 0.5 T and 1 T have also been characterized as mid-field. By contrast, "low-field" refers generally to MRI systems operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime. Within the low-field regime, low-field MRI systems operating with a $B_0$ field of less than 0.1 T are referred to herein as "very low-field" and low-field MRI systems operating with a $B_0$ field of less than 10 mT are referred to herein as "ultra-low field."

In some embodiments, an RF coil assembly may be used alone or in combination with an MRI device to perform MR imaging. In some embodiments, the infant support may be coupled to an MRI device (e.g., an MRI device comprising an RF coil assembly or an MRI device alone, as described herein), or an RF coil assembly alone to facilitate MR imaging of an infant, including, for example, MR imaging of at least a portion of the infant's head in some embodiments.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods, for example, as shown in FIG. 49. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "substantially", "approximately", and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A system to facilitate imaging an infant using a magnetic resonance imaging (MRI) device, the MRI device comprising first and second magnets arranged in a bi-planar arrangement having an imaging region therebetween, the system comprising:
    a radio frequency (RF) coil assembly configured to be coupled to a coupling mechanism of the MRI device, the coupling mechanism being disposed within the imaging region of the MRI device and coupled to the first magnet of the MRI device, the RF coil assembly comprising:
        a first RF coil configured to transmit RF signals during MRI and/or be responsive to MR signals generated during MRI; and
        a helmet for supporting at least a portion of the infant's head; and
    an infant support to support at least a portion of the infant's body and configured to be removably coupled to the RF coil assembly and the coupling mechanism of the MRI device, wherein the infant support comprises arms configured to be received by the coupling mechanism of the MRI device such that when the arms of the infant support are received by the coupling mechanism of the MRI device, the infant support is positioned between the first and second magnets of the MRI device at least partially within the imaging region of the MRI device.

2. The system of claim 1, wherein the helmet supports the first RF coil.

3. The system of claim 2, wherein the first RF coil is housed inside the helmet.

4. The system of claim 1, wherein the first RF coil is disposed on or proximate to an exterior surface of the helmet.

5. The system of claim 1, wherein the infant support is configured to be coupled to the helmet.

6. The system of claim 1, wherein the first RF coil is removably coupled to the helmet.

7. The system of claim 1, wherein the RF coil assembly further comprises a second RF coil configured to receive MR signals during MRI, the second RF coil being removably coupled to the helmet.

8. The system of claim 1, wherein the infant support comprises:
    a tray for positioning the infant thereon along a longitudinal axis extending along a length of the tray, the tray having a surface and sides coupled to and extending upwards from the surface; and
    a base coupled to the tray comprising the arms, wherein the arms extend outward from the base in a direction along the longitudinal axis.

9. The system of claim 8, further comprising the coupling mechanism, the coupling mechanism comprising:
first and second receiving portions for receiving the arms of the infant support, wherein the coupling mechanism is coupled to the RF coil assembly.

10. The system of claim 1, wherein a maximum dimension of an interior of the helmet is less than 20 centimeters.

11. An infant support for supporting an infant during imaging by a magnetic resonance imaging (MRI) device, the MRI device comprising first and second magnets arranged in a bi-planar arrangement having an imaging region therebetween, the apparatus comprising:
a tray for positioning the infant thereon along a longitudinal axis extending along a length of the tray, the tray having a surface and sides coupled to and extending upwards from the surface; and
a base coupled to the tray and configured to be removably coupled to a coupling mechanism of the MRI device, the coupling mechanism disposed within the imaging region of the MRI device and coupled to the first magnet of the MRI device, the base comprising arms extending outward from the base in a direction along the longitudinal axis, wherein the arms are configured to be received by respective receiving portions of the coupling mechanism of the MRI device, such that, when the arms of the infant support are received by the coupling mechanism of the MRI device, the infant support is positioned between the first and second magnets of the MRI device at least partially within the imaging region of the MRI device.

12. The infant support of claim 11, wherein each of the arms comprise a respective snap at a distal end of the arm, the snap configured to be received by the coupling mechanism.

13. The infant support of claim 11, further comprising a bridge supporting the tray on the base and providing a gap between the base and the tray.

14. The infant support of claim 11, wherein the base further comprises a notch disposed between the arms, the notch complementary to a protrusion of the coupling mechanism coupled to the MRI device.

15. The infant support of claim 11, wherein the base further comprises a protrusion disposed between the arms, the protrusion complementary to a notch of the coupling mechanism coupled to the MRI device.

16. The infant support of claim 11, wherein the surface is tapered such that a proximal end of the surface has a width that is greater than a width of a distal end of the surface.

17. A method for positioning at least a portion of an infant in an imaging region of a magnetic resonance imaging (MRI) device between first and second magnets of the MRI device arranged in a bi-planar configuration, using an infant support configured to support the infant during imaging, the infant support comprising a base, a tray supported by the base, and arms coupled to the base, the method comprising:
placing the infant on the tray along a longitudinal axis of the infant support;
moving the infant support towards an RF coil assembly of the MRI device in a direction along the longitudinal axis so that the arms are removably inserted into a coupling mechanism of the MRI device, the coupling mechanism being disposed within the imaging region and coupled to the RF coil assembly and a first magnet of the MRI device, and at least a portion of the infant's head is disposed within an opening of the RF coil assembly, wherein when the arms of the infant support are coupled to the coupling mechanism of the MRI device, the at least a portion of the infant is positioned within the imaging region of the MRI device and between the first and second magnets of the MRI device; and
imaging the infant using the MRI device.

18. The method of claim 17, wherein the moving comprises moving the infant support until either a notch of the infant support receives a protrusion of the coupling mechanism or a protrusion of the infant support is received by a notch of the coupling mechanism.

19. The method of claim 17, wherein the moving comprises moving the infant support until snaps disposed at distal ends of the arms are received by respective distal ends of guides of the coupling mechanism.

* * * * *